United States Patent [19]

Bender et al.

[11] Patent Number: 5,242,903
[45] Date of Patent: Sep. 7, 1993

[54] RENIN INHIBITORS

[75] Inventors: Wolfgang Bender; Günther Kinast, both of Wuppertal; Andreas Knorr, Erkrath; Johannes-Peter Stasch, Wuppertal, all of Fed. Rep. of Germany

[73] Assignee: Bayer Aktiengesellschaft, Leverkusen, Fed. Rep. of Germany

[21] Appl. No.: 771,077

[22] Filed: Oct. 2, 1991

Related U.S. Application Data

[62] Division of Ser. No. 553,493, Jul. 13, 1990, Pat. No. 5,095,006.

[30] Foreign Application Priority Data

Aug. 5, 1989 [DE] Fed. Rep. of Germany ....... 3926021
Feb. 16, 1990 [DE] Fed. Rep. of Germany ....... 4004820

[51] Int. Cl.$^5$ .................. A61K 31/195; A61K 37/02; C07K 5/02; C07K 5/06
[52] U.S. Cl. ........................ 514/18; 514/19; 530/323; 530/330; 530/331; 548/314.7; 548/338.1; 548/312.1; 548/315.1; 548/312.4; 562/445
[58] Field of Search ................... 514/18, 19; 530/323, 530/330, 331; 548/344; 562/445

[56] References Cited

U.S. PATENT DOCUMENTS 4,560,505  12/1985  Pinuri et al. .......................... 530/328
4,585,586   4/1986  Ditrapani et al. ..................... 514/17

OTHER PUBLICATIONS

Johnson, Rodney L., *J. Med. Chem.*, (1983), 26, pp. 1457-1462.
Johnson, Rodney L. and Verschoor, Karen, *J. Med. Chem.*, (1980), 23, pp. 666-669.
Bolis et al., *J. Med. Chem.*, 30: pp. 1729-1737 (1987).
Haber et al. *J. Cardiovasc. Pharmac.* 10 (Supp. 7) pp. 554-558.
Plattner et al., *J. Med. Chem.* 31: 2277-2288, (1988).
Denkewalter et al., *Progress in Drug Research*, 10: 511-512 (1966).
A. Burger, editor., *Medicinal Chemistry, 2nd edition, pp. 565-571, 578-581, 600-601 (1960).*

Primary Examiner—Ronald W. Griffin
Attorney, Agent, or Firm—Sprung Horn Kramer & Woods

[57] ABSTRACT

Renin-inhibiting peptides of the formula

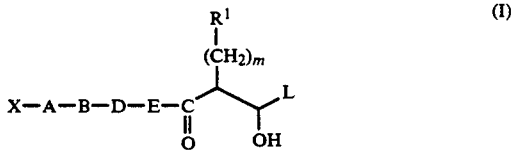

in which
X represents a group of the formula

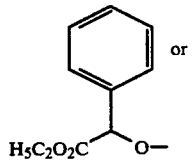

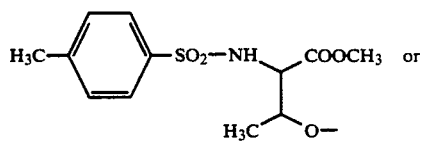

represents hydroxyl, alkoxy having up to 8 carbon atoms, benzyloxy or a group of the formula $-NR^4R^5$,
A, B, D and E are identical or different and in each case
represent a direct bond,
represent a radical of the formula

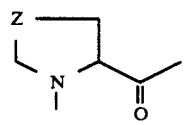

in which
Z denotes oxygen, sulphur or the methylene group
represents a grouping of the formula

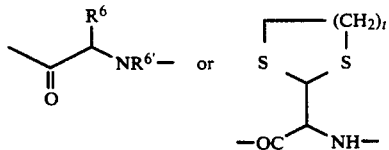

m represents a number 0, 1 or 2, and
L represents a group of the formula $-CH_2-NR^2R^3$ and physiologically acceptable salts thereof.

1 Claim, No Drawings

RENIN INHIBITORS

This is a division of application Ser. No. 07/553,493, filed Jul. 13, 1990, U.S. Pat. Pat. No. 5,095,006.

The invention relates to new renin-inhibiting peptides, to processes for their preparation and to their use in medicaments, in particular in circulation-influencing medicaments.

Renin is a proteolytic enzyme which is predominantly produced by the kidneys and secreted into the plasma. It is known that renin eliminates the decapeptide angiotensin I from angiotensinogen in vivo. Angiotensin I is in turn degraded in the lungs, the kidneys or other tissues to give the octapeptide angiotensin II, which has an effect on blood pressure. The different effects of angiotensin II such as vasoconstriction, Na+ retention in the kidneys, aldosterone release in the adrenal gland and increase in tone of the sympathetic nervous system act synergistically in the sense of an increase in blood pressure.

The activity of the renin-angiotensin system can be manipulated pharmacologically by the inhibition of the activity of renin or the angiotensin converting enzyme (ACE) and also be blockade of angiotensin II receptors. The development of orally administrable ACE inhibitors has thus led to new antihypertensives (cf. DOS 3,628,650, Am. J. Med. 77, 690, 1984).

A relatively new approach is to intervene in the renin-angiotensin cascade at an earlier point in time, namely by inhibiting the highly specific peptidase renin.

Different types of renin inhibitors have hitherto been developed: renin-specific antibodies, phospholipids peptides having the N-terminal sequence of prorenin, synthetic peptides as substrate analogues and modified peptides.

The amino acid (3S, 4S)-4-amino-3-hydroxy-6-methyl-heptanecarboxylic acid (statin) is additionally known [cf. D.H. Rich, J. Med. Chem. 28, 263–73 (1985), Boger, J.; Lohr, N.S.; Ulm, E.W., Pe, M.; Blaine, E.H.; Fanelli, G.M.; Lin, T.-Y; Payne, L.S.; Schorn, T.W.; LaMont, B.I.; Vassil, T.C.; Stabilito, I.I.; Veber, D.F.; Rick, D.H.; Boparai, A.S. Nature (London) 1983, 303, 81].

New renin inhibitors having a retrostatin or retrostatin-analogous middle section have now been found, in which the acid C terminus is situated in the N-terminal position and the acid N-terminus in the C-terminal position and the accompanying amino acid sequences are also reversed. These renin inhibitors surprisingly show a high selectivity for human renin.

The invention relates to renin inhibitors of the general formula (I)

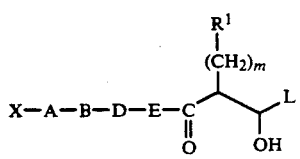

in which

X represents a group of the formula

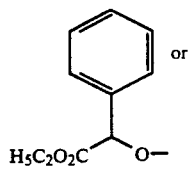

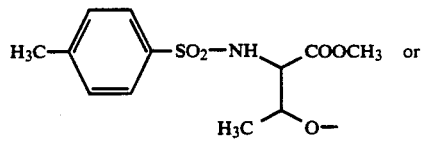

represents hydroxyl, alkoxy having up to 8 carbon atoms, benzyloxy or a group of the formula $-NR^4R^5$, in which $R^4$ and $R^5$ are identical or different and in each case denote hydrogen, straight-chain or branched alkyl having up to 8 carbon atoms, which is optionally substituted by phenyl, or cycloalkyl having 3 to 8 carbon atoms, or aryl having 6 to 10 carbon atoms which, in turn, may be substituted by halogen, or $R^4$ and $R^5$, together with the nitrogen atom, form a 5 to 7-membered heterocycle having up to 3 heteroatoms from the series comprising nitrogen, sulphur or oxygen, A, B, D and E are identical or different and in each case represent a direct bond, represent a radical of the formula

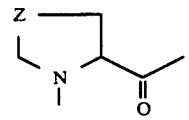

in which

Z denotes oxygen, sulphur or the methylene group represents a grouping of the formula

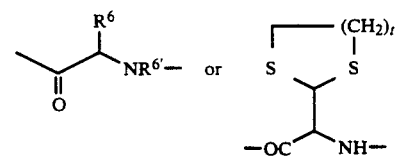

in which t denotes the number 1 or 2, $R^6$ denotes hydrogen or phenyl or denotes straight-chain or branched alkyl having up to 8 carbon atoms, which is optionally substituted by carboxyl, hydroxyl, halogen or by alkoxy or alkoxycarbonyl in each case having up to 6 carbon atoms, which, in turn, may be substituted by phenyl, or is substituted by a group of the formula $-NR^7R^8$ or $-CONR^7R^8$ in which $R^7$ and $R^8$ are identical or different and in each case denote an amino protecting group, hydrogen, acetoxy, aryl having 6 to 10 carbon atoms or straight-chain or branched alkyl having up to 6 carbon atoms, which, in turn, may be substituted by amino, or is substituted by aryl having 6 to 10 carbon atoms, which is optionally monosubstituted to trisubstituted by identical or different substituents from the series comprising halogen, nitro, hydroxyl or alkoxy having up to 6 carbon atoms, or is substituted by indolyl, imidazolyl, pyridyl, triazolyl or pyrazolyl which, in turn, may be substituted by $R^8$, in which $R^8$ has the abovementioned meaning, $R^{6'}$ denotes hydrogen, benzyl or straight-chain or branched alkyl having up to 6 carbon atoms, in their D-form, L-form or as the D, L-isomer mixture, m represents a number 0, 1 or 2, $R^1$ represents a straight-chain or branched alkyl having up to 8 carbon atoms, represents cycloalkyol having 3 to 8 carbon atoms, represents aryl having 6 to 10 carbon atoms, which may optionally be substituted by nitro, cyano, halogen or by straight-chain or branched alkyl having up to 6 carbon atoms, represents a group of the formula $-CH_2-NR_2R_3$ or

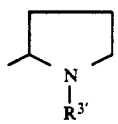

in which $R^2$ and $R^3$ are identical or different and in each case represent hydrogen, phenyl or represent straight-chain or branched alkyl having up to 8 carbon atoms, which is optionally substituted by aryl having 6 to 10 carbon atoms or pyridyl, represent a group of the formula $-COR^9$, in which $R^9$ denotes straight-chain or branched alkyl or alkoxy having up to 8 carbon atoms or aryl having 6 to 10 carbon atoms, which, in turn, may be substituted by carboxyl, alkoxycarbonyl having up to 8 carbon atoms or by a group of the formula $-CONR^4R^5$ or $-CO-NR^{10}R^{11}$, in which $R^4$ and $R^5$ have the abovementioned meanings and $R^{10}$ and $R^{11}$ are identical or different and in each case denote hydrogen or straight-chain or branched alkyl having up to 8 carbon atoms, which, in turn, may be substituted by phenyl or pyridyl, or $R^2$ or $R^3$ represents an amino protecting group or $R^2$ and $R^3$ together represent phthalimido or morpholino or represent a group of the formula

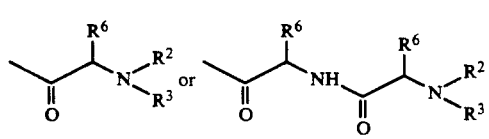

in which $R^2$, $R^3$ and $R^6$ have the abovementioned meanings, $R^{3'}$ has the abovementioned meaning of $R^2$ and is identical to or different therefrom, and their physiologically acceptable salts.

Amino protecting group in the context of the invention represents the customary amino protecting groups used in peptide chemistry.

These preferably include: benzyloxycarbonyl, 4-bromobenzyloxycarbonyl, 2-chlorobenzyloxycarbonyl, 3-chlorobenzyloxycarbonyl, dichlorobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobezyloxycarbonyl, 2-nitro-4,5-dimethoxybenzyloxycarbonyl, 3,4,5-trimethoxybenzyloxycarbonyl, methoxycarbonyl, ethoxycarbonyl, propoxycarbonyl, isopropoxycarbonyl, butoxycarbonyl, isobutoxycarbonyl, tert-butoxycarbonyl, pentoxycarbonyl, isopentoxycarbonyl, hexoxycarbonyl, cyclohexoxycarbonyl, octoxycarbonyl, 2-ethylhexoxycarbonyl, 2-iodohexoxycarbonyl, 2-bromoethoxycarbonyl, 2-chloroethoxycarbonyl, 2,2,2-tricloroethoxycarbonyl, 2,2,2-trichloro-tert-butoxycarbonyl, benzohydroyloxycarbonyl, bis(4-methoxyphenyl)methoxycarbonyl, phenacyloxycarbonyl, 2-trimethylsilylethoxycarbonyl, 2-(di-n-butyl-methylsily)ethoxycarbonyl, 2-triphenylsilylethoxycarbonyl, 2-(dimethyl-tert-butylsilyl)ethoxycarbonyl, menthyloxycarbonyl, vinyloxycarbonyl, allyloxycarbonyl, phenoxycarbonyl, tolyloxycarbonyl, 2,4-dinitrophenoxycarbonyl, 4-nitrophenoxycarbonyl, 2,4,5-trichlorophenoxycarbonyl, naphthyloxycarbonyl, fluorenyl-9-methoxycarbonyl, ethylthiocarbonyl, methylthiocarbonyl, butylthiocarbonyl, tert.-butylthiocarbonyl, phenylthiocarbonyl, benzylthiocarbonyl, methylaminocarbonyl, ethylaminocarbonyl, methylthiocarbonyl, butylthiocarbonyl, tert-butylthiocarbonyl, phenylthiocarbonyl, benzylthiocarbonyl, methylaminocarbonyl, ethylaminocarbonyl, propylaminocarbonyl, iso-propylaminocarbonyl, formyl, acetyl, propionyl, pivaloyl, 2-chloroacetyl, 2-bromoacetyl, 2-iodoacetyl, 2,2,2-trifluoracetyl, 2,2,2-trichloroacetyl, benzoyl, 4-chlorobenzoyl, 4-methoxybenzoyl, 4-nitrobenzyl, 4-nitrobenzoyl, naphthylcarbonyl, phenoxyacetyl, adamantylcarbonyl, dicyclohexylphosphoryl, diphenylphosphoryl, dibenzylphosphoryl, di-(4-nitrobenzyl)phosphoryl, phenoxyphenylphosphoryl, diethylphosphinyl, diphenylphosphinyl, phthaloyl or phthalimido.

Particularly preferred amino protecting groups are benzyloxycarbonyl, 3,4-dimethoxybenzyloxycarbonyl, 3,5-dimethoxybenzyloxycarbonyl, 4-methoxybenzyloxycarbonyl, 4-nitrobenzyloxycarbonyl, 2-nitrobenzyloxycarbonyl, 3,4,5-trimethoxybenzyloxycarbonyl, methoxycarbonyl, ethoxycarbonyl, propoxycarbonyl, isopropoxycarbonyl, butoxycarbonyl, isobutoxycarbonyl, tert-butoxycarbonyl, cyclohexoxycarbonyl, hexoxycarbonyl, octoxycarbonyl, 2-bromoethoxycarbonyl, 2-chloroethoxycarbonyl, phenoxyacetyl, naphthylcarbonyl, adamantylcarbonyl, phthaloyl, 2,2,2-trichloroethoxycarbonyl, 2,2,2-trichloro-tert-butoxycarbonyl, menthyloxycarbonyl, vinyloxycarbonyl, allyloxycarbonyl, phenoxycarbonyl, 4-nitrophenoxycarbonyl, fluorenyl-9-methoxycarbonyl, formyl, acetyl, propionyl, pivaloyl, 2-chloroacetyl, 2-bromoacetyl, 2,2,2-trifluoroacetyl, 2,2,2-trichloroacetyl, benzoyl, 4-chlorobenzoyl, 4-bromobenzoyl, 4-nitrobenzoyl, phthaloimido or isovaleroyl.

The compounds of the general formula (I) according to the invention have several asymmetric carbon atoms. They may be present independently of one another in the D- or the L-form. The invention includes the optical antipodes as well as the isomer mixtures or racemates.

Preferably, the groups A, B, D, E and $R^3$ are present independently of one another in the optically pure form, preferably the D-form.

The group of the formula

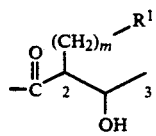

has 2 asymmetric carbon atoms which can be present independently of one another in the R- or S-configuration, for example in the 2S,3S, 2R,3R, 2S,3R or 2R,3S configuration.

The grouping is also employed as an isomer mixture.

The compounds according to the invention exist in stereoisomeric forms which behave either as image and mirror image (enantiomers) or which do not behave as image and mirror image (diastereomers). The invention relates both to the antipodes and to the racemix modifications and the diastereomer mixtures. The racemic modifications, like the diastereomers, can be separated into the stereoisomerically uniform constituents in a known manner (cf. E. L. Eliel, Stereochemistry of Carbon Compounds, McGraw Hill, 1962).

The compounds of the general formula (I) according to the invention can be present in the form of their salts. These may be salts of compounds according to the invention with inorganic or organic acids or bases. The acid addition products preferably include salts with hydrochloric acid, hydrobromic acid, hydroiodic acid, sulphuric acid, phosphoric acid or with carboxylic acids such as acetic acid, propionic acid, oxalic acid, glycolic acid, succinic acid, maleic acid, hydroxymaleic acid, methylmaleic acid, fumaric acid, adipic acid, malic acid, tartaric acid, citric acid, benzoic acid, cinnamic acid, lactic acid, ascorbic acid, salicylic acid, 2-acetoxybenzoic acid, nicotinic acid, isonicotinic acid, or sulphonic acids such as methanesulphonic acid, ethanesulphonic acid, benzenesulphonic acid, toluenesulphonic acid, naphthalene-2-sulphonic acid or naphthalene-disulphonic acid.

Preferred compounds of the general formula (I) are those in which

X represents a group of the formula

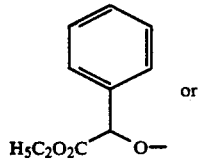

or

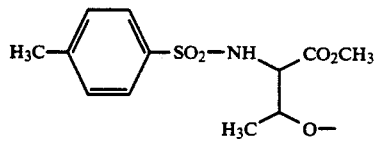

represents hydroxyl, alkoxy having up to 6 carbon atoms, benzyloxy or a group of the formula $-NR^4R^5$, in which $R^4$ and $R^5$ are identical or different and in each case denote hydrogen, straight-chain or branched alkyl having up to 6 carbon atoms, which is optionally substituted by phenyl, or denote cyclopropyl, cyclopentyl, cyclohexyl or phenyl which, in turn, is substituted by fluorine or chlorine, or $R^4$ and $R^5$, together with the nitrogen atom, form a morpholine ring, A, B, D and E are identical or different and in each case represent a direct bond or represent a radical of the formula

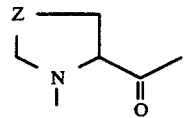

in which

Z denotes oxygen, sulphur or the methylene group, or represents a radical of the formula

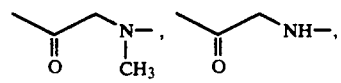

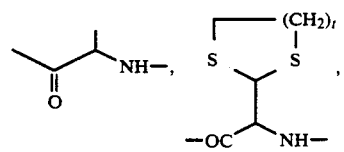

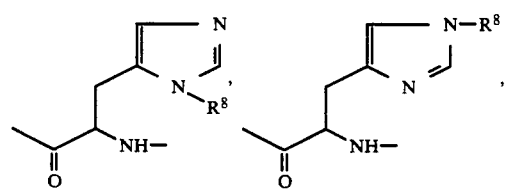

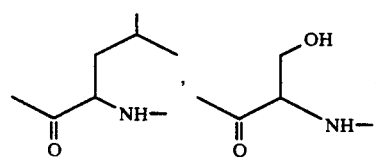

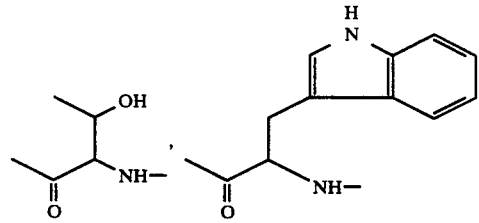

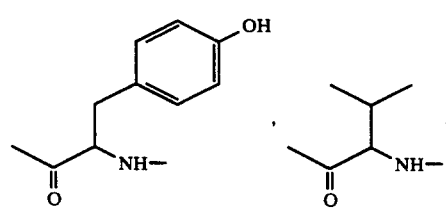

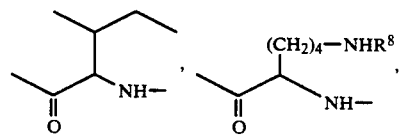

-continued

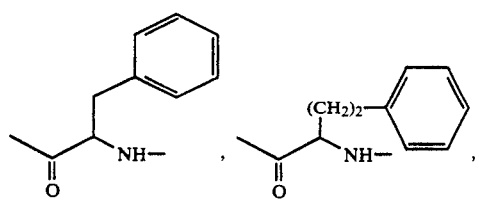

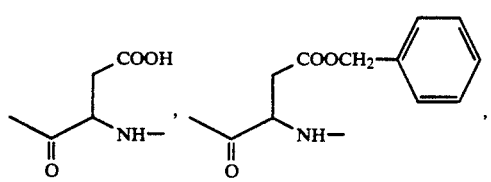

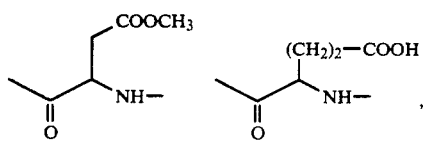

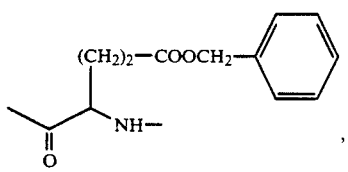

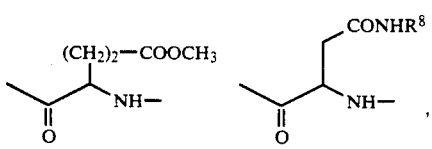

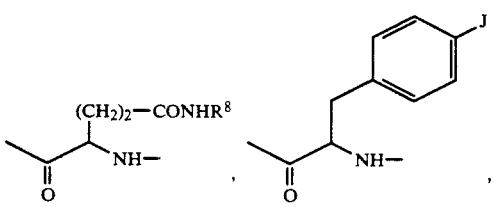

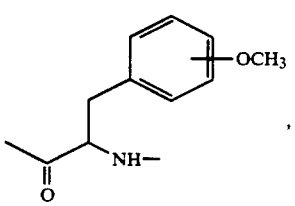

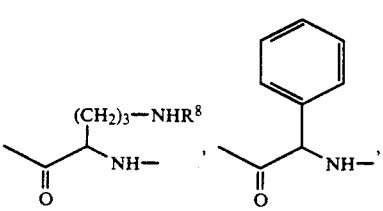

-continued

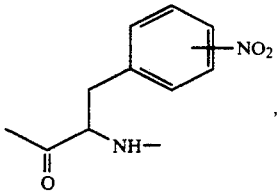

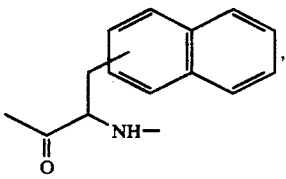

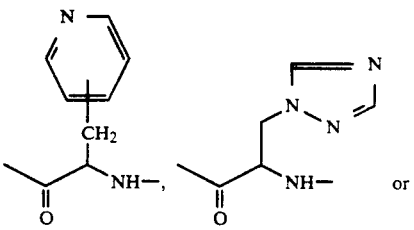

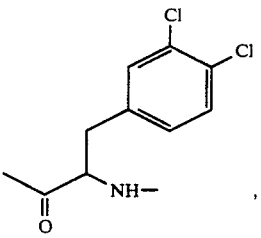

in which
t denotes the number 1 or 2,
$R^8$ denotes hydrogen, straight-chain or branched alkyl having up to 4 carbon atoms or an amino protecting group,
in their D-form, L-form or as the D, L-isomer mixture,
m represents a number 0, 1 or 2,
$R^1$ represents a straight-chain or branched alkyl having up to 6 carbon atoms,
represents cyclopropyl, cyclopentyl or cyclohexyl,
represents phenyl which is optionally substituted by nitro, cyano, fluorine or chlorine.
represents a group of the formula —CH$_2$—NR$_2$R$^3$ or

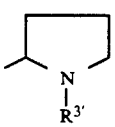

in which
$R^2$ and $R^3$ are identical or different and in each case represent hydrogen, phenyl or
represent straight-chain or branched alkyl having up to 6 carbon atoms, which is optionally substituted by phenyl or pyridyl,
represent a group of the formula —COR$^9$, in which
$R^9$ denotes straight-chain or branched alkyl or alkoxy having up to 6 carbon atoms, or phenyl which, in turn, may be substituted by carboxyl, alkoxycarbonyl having up to 6 carbon atoms or by a group of the formula —CONR$^4$R$^5$ or —CO—NR$^{10}$R$^{11}$,
in which R$^4$ and R$^5$ have the abovementioned meanings, R$^{10}$ and R$^{11}$ are identical or different and in each case denote hydrogen or straight-chain or branched alkyl having up to 6 carbon atoms, which, in turn, may be substituted by phenyl or pyridyl, or R$^2$ or R$^3$ represents an amino protecting group or R$^2$ and R$^3$ together represent phthalimido or morpholino or R$^2$ or R$^3$ represents the group of the formula

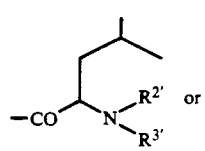

or

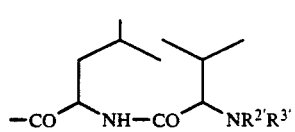

in which

R$^{2'}$ and R$^{3'}$ have the abovementioned meanings, and their physiologically acceptable salts.

Particularly preferred compounds of the general formula (I) are those
in which

X represents a group of the formula

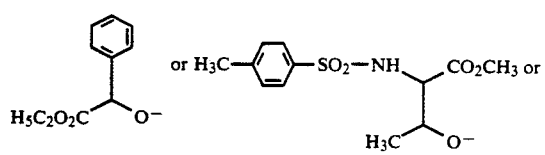

represents hydroxyl, alkoxy having up to 4 carbon atoms, benzyloxy or a group of the formula —NR$^4$R$^5$,
in which R$^4$ and R$^5$ are identical or different and in each case denote hydrogen, straight-chain or branched alkyl having up to 4 carbon atoms, which is optionally substituted by phenyl, or cyclopentyl, or phenyl which, in turn, may be substituted by chlorine, or R$^4$ and R$^5$, together with the nitrogen atom, form a morpholine ring, A, B, D and E are identical or different and in each case represent a direct bond or represent glycyl (Gly), alanyl (Ala), arginyl (Arg), histidyl (His), leucyl (Leu), isoleucyl (Ile), seryl (Ser), threonyl (Thr), trypotophyl (Trp), tyrosyl (Tyr), valvyl (Val), lysyl (Lys), aspartyl (Asp), asparaginyl (Asn), glutamyl (Glu) or phenylalanyl (Phe) or prolyl (Pro) or represent a group of the formula

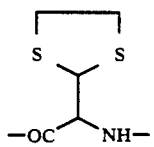

if appropriate having an amino protecting group, in their L-form or D-form, m represents the number 1, R$^1$ represents straight-chain or branched alkyl having up to 4 carbon atoms, cyclohexyl or phenyl, L represents a group of the formula —CH$_2$—NR$^2$R$^3$ or

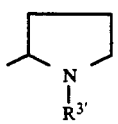

in which

R$^2$ and R$^3$ are identical or different and in each case represent hydrogen, phenyl or represent straight-chain or branched alkyl having up to 4 carbon atoms, which is optionally substituted by phenyl or pyridyl, represent a group of the formula —COR$^9$, in which R$^9$ denotes straight-chain or branched alkyl or alkoxy having up to 4 carbon atoms, or phenyl which, in turn, may be substituted by carboxyl, alkoxycarbonyl having up to 4 carbon atoms or by a group of the formula —CONR$^4$R$^5$ or —CONR$^{10}$R$^{11}$, R$^4$ and R$^5$ have the abovementioned meanings, R$^{10}$ and R$^{11}$ are identical or different and in each case denote hydrogen or straight-chain or branched alkyl having up to 4 carbon atoms, which, in turn, may be substituted by phenyl or pyridyl, or R$^2$ or R$^3$ represents an amino protecting group or R$^2$ and R$^3$ together represent phthalimido or morpholino or R$^2$ or R$^3$ represent the group of the formula

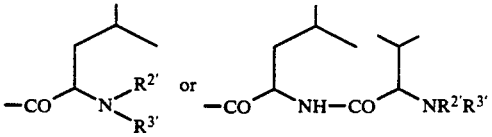

in which

R$^{2'}$ and R$^{3'}$ have the abovementioned meanings, and their physiologically acceptable salts, The compounds of the general formula (I) according to the invention.

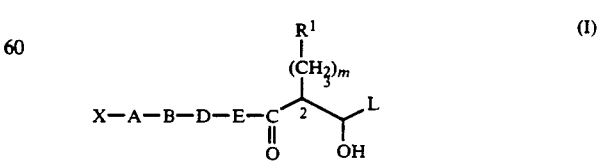

in which

X, A, B, D, E, R$^1$, m, and L have the abovementioned meanings, are obtained by a process in which

[A] either compounds of the general formula (II)

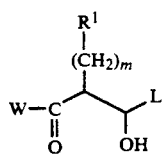

in which

R[1], L and m have the abovementioned meanings, and

W represents a typical carboxyl protecting group, such as, for example, benzyloxy or alkoxy having up to 6 carbon atoms, which are optionally substituted by alkoxycarbonyl having up to 6 carbon atoms, or stereoselective compounds of the general formula (III)

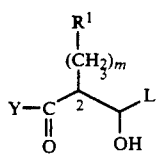

in which

R[1], L, and m have the abovementioned meanings, and

Y represents an N-bonded oxazolidin-2-one ring, which is optionally disubstituted by alkyl having up to 4 carbon atoms, benzyl or phenyl, are first converted into the corresponding acids by elimination of the protecting groups according to a customary method and in a second step are reacted with compounds of the general formula (IV)

$$X'-A-B-D-E-NH_2 \qquad (IV)$$

in which

A, B, D and E have the abovementioned meanings and

X' represents a carboxyl protecting group, in inert solvents, if appropriate in the presence of an auxiliary and the protecting group X' is eliminated by a customary method and the radicals X and L are introduced by a known method, for example by amination, esterificaton or hydrolysis, to include the abovementioned scope of meaning, or by a process in which

[B] compounds of the general formulae (II) and (III) are prepared by reaction of an appropriate fragment, consisting of one or more amino acid groupings, containing a free carboxyl group, if appropriate in activated form, with a complementary fragment, consisting of one or more amino acid groupings, containing an amino group, if appropriate in activated form, and this procedure is optionally repeated with appropriate fragments until the desired peptides of the general formula (I) have been prepared, protecting groups are subsequently optionally removed, replaced by other protecting groups and the radicals L and X are optionally derivatized according to the methods mentioned under process [A], it being possible for additional reactive groups, such as, for example, amino or hydroxyl groups, to be protected in the side chains of the fragments, if appropriate, by customary protecting groups.

The processes can be illustrated by the following scheme:

[A]

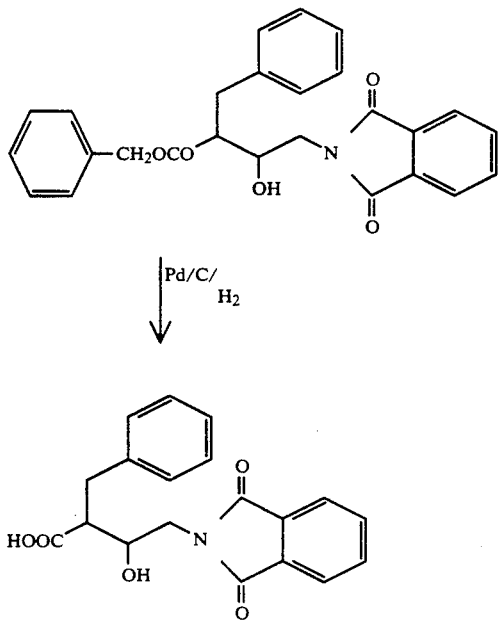

-continued
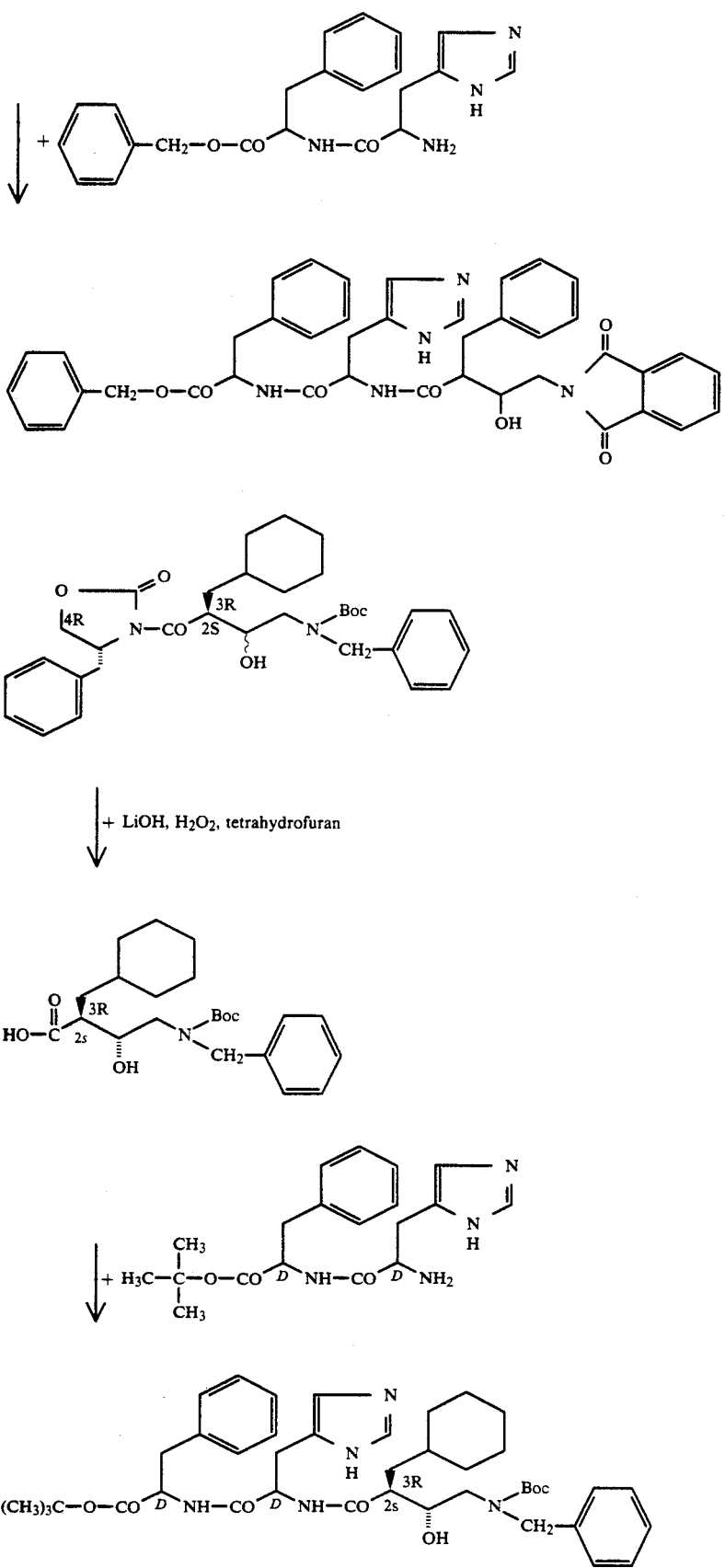

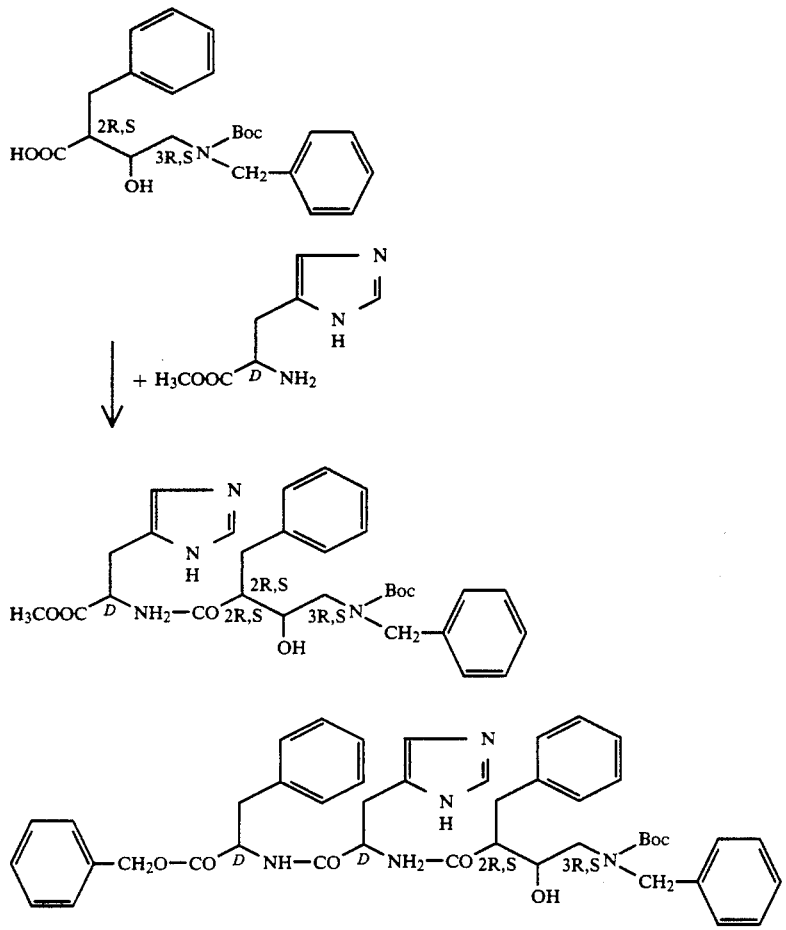

As auxiliaries, condensing agents are preferably employed which can also be bases, in particular if the carboxyl group is activated as the anhydride. Preferably, the customary condensing agents such as carbodiimides, for example N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride, or carbonyl compounds such as carbonyldiimidazole, or 1,2-oxazolium compounds such as 2-ethyl-5-phenyl-1,2-oxazolium-3-sulphonate or 2-tert-butyl-5-methyl-oxazolium perchlorate, or acylamino compounds such as 2-ethoxy-1-ethoxycarbonyl-1,2-dihydroquinoline, or propanephosphonic anhydride, or isobutyl chloroformate, or benzotriazolyloxy-tris(dimethylamino)phosphonium hexafluorophosphate, or, as bases, alkali metal carbonates, for example sodium carbonate or hydrogen carbonate or potassium carbonate or hydrogen carbonate, or organic bases such as trialkylamines, for example triethylamine, N-ethylmorpholine or N-methylpiperidine are employed here.

Suitable solvents are the customary inert solvents which do not change under the reaction conditions selected in each case, in particular the activation methods selected in each case. These preferably include water or organic solvents such as methanol, ethanol, propanol, isopropanol, or ethers such as diethyl ether, glycol monomethyl ether or glycol dimethyl ether, dioxane or tetrahydrofuran, or hydrocarbons such as benzene, toluene, xylene, cyclohexane or mineral oil fractions, or halogenated hydrocarbons such as methylene chloride, chloroform, carbon tetrachloride, or acetone, dimethyl sulphoxide, dimethylformamide, hexamethylphosphoramide, ethyl acetate, pyridine, triethylamine or picoline. It is also possible to use mixtures of the solvents mentioned.

Examples of activated carboxyl groups are: carboxylic acid azides (obtainable, for example, by reaction of protected or unprotected carboxylic acid hydrazides with nitrous acid, its salts or alkyl nitrites (for example isoamyl nitrite), or unsaturated esters, in particular vinyl esters, (obtainable, for example, by reaction of a corresponding ester with vinyl acetate), carbamoylvinyl esters (obtainable, for example, by reaction of a corresponding acid with an isoxazolium reagent), alkoxyvinyl esters (obtainable, for example, by reaction of the corresponding acids with alkoxyacetylenes, preferably ethoxyacetylene), or amidino esters, for example, N,N'- or N,N-disubstituted amidino esters (obtainable, for example, by reaction of the corresponding acid with an N,N'-disubstituted carbodiimide (preferably dicyclohexylcarbodiimide, diisopropylcarbodiimide or N-(3-dimethylaminopropyl)-N'-ethylcarbodiimide hydrochloride) or with an N,N-disubstituted cyanamide, or aryl esters, in particular by phenyl esters substituted with electron-withdrawing substituents, for example 4-nitrophenyl, 4-methylsulphonylphenyl, 2,4,5-trichlorophenyl, 2,3,4,5,6-pentachlorophenyl or 4-phenyldiazophenyl esters (obtainable, for example, by reaction of the corresponding acid with an appropriately substituted phenol, if appropriate in the presence of a condensing agent such as, for example, N,N'-dicyclohexylcarbodiimide, diisopropylcarbodiimide, N-(3-dimethylaminopropyl)-N'-ethylcarbodiimide hydrochloride, isobutyl chloroformate, propanephosphonic anhydride) or benzotriazolyloxytris(dimethylamino)phosphonium hexafluorophosphate, or cyanomethyl esters (obtainable, for example, by reaction of the corresponding acid with chloroacetonitrile in the presence of a base), or thioesters, in particular nitrophenylthioesters (obtainable, for example, by reaction of the corresponding acid with nitrothiophenols, if appropriate in the presence of condensing agents such as N,N'-dicyclohexylcarbodiimide, diisopropylcarbodiimide, N-(3-dimethylaminopropyl)-N'-ethylcarbodiimide hydrochloride, isobutyl chloroformate, propanephosphonic anhydride or benzotriazolyloxytris(dimethylamino)phosphonium hexafluorophosphate), or amino or amido esters (obtainable, for example, by reaction of the corresponding acid with an N-hydroxyamino or N-hydroxyamido compound, in particular N-hydroxysuccinimide, N-hydroxypiperidine, N-hydroxyphthalimide, N-hydroxy-5-norbornene-2,3-dicarboxiide or 1-hydroxybenzotriazole, if appropriate in the presence of condensing agents such as N,N'-dicyclohexylcarbodiimide, diisopropylcarbodiimide or N-(3-dimethylaminopropyl)-N'-ethylcarbodiimide hydrochloride, isobutyl chloroformate or propanephosphonic anhydride), or anhydrides of acids, preferably symmetrical or unsymmetrical anhydrides of the corresponding acids, in particular anhydrides with inorganic acids, (obtainable, for example, by reaction of the corresponding acid with thionyl chloride, phosphorus pentoxide or oxalyl chloride), or anhydrides with carbonic acid half derivatives, for example, carbonic acid lower alkyl half esters (obtainable, for example, by reaction of the corresponding acid with halogenoformic acid lower alkyl esters, for example methyl chloroformate, ethyl chloroformate, propyl chloroformate, isopropyl chloroformate, butyl chloroformate or isobutyl chloroformate or with 1-lower alkoxycarbonyl-2-lower alkoxy-1,2-dihydroquinoline, for example 1-methoxycarbonyl-2-ethoxy-1,2-dihydroquinoline), or anhydrides with dihalogenophosphoric acids (obtainable, for example, by reaction of the corresponding acid with phosphorus oxychloride), or anhydrides with phosphoric acid derivatives or phosphorous acid derivatives, (for example propanephosphonic anhydride, H. Wissmann and H.J. Kleiner, Angew. Chem. Int. Ed. 19, 133 (1980))

or anhydrides with organic carboxylic acids (obtainable, for example, by reaction of the corresponding acids with an optionally substituted lower alkane- or phenylalkane-carbonyl halide, in particular phenylacetyl, pivaloyl or trifluoroacetyl chloride), or anhydrides with organic sulphonic acids (obtainable, for example, by reaction of an alkali metal salt of a corresponding acid with a sulphonyl halide, in particular methane-, ethane-, benzene- or toluenesulphonyl chloride), or symmetrical anhydrides (obtainable, for example, by condensation of corresponding acids, if appropriate in the presence of condensing agents such as N,N'-dicyclohexylcarbodiimide, diisopropylcarbodiimide, N-(3-dimethylaminopropyl)-N'-ethylcarbodiimide hydrochloride, isobutyl chloroformate, propanephosphonic anhydride or benzotriazolyloxy-tris(dimethylamino)-phosphonium hexafluorophosphate.

Reactive cyclic amides are, in particular, amides with five-membered heterocycles having 2 nitrogen atoms and optionally aromatic character, preferably amides with imidazoles or pyrazoles (obtainable, for example, by reaction of the corresponding acids with N,N'-carbonyldiimidazole or—if appropriate in the presence of condensing agents such as, for example, N,N'-dicyclohexylcarbodiimide, N,N'-diisopropylcarbodiimide, N-(3-dimethylaminopropyl)-N'-ethylcarbodiimide hydrochloride, isobutyl chloroformate, propanephosphonic anhydride, benzotriazolyloxy-tris(dimethylamino)phosphonium hexafluorophosphate—with, for example, 3,5-dimethylpyrazole, 1,2,4-triazole or tetrazole.

A complementary fragment having a free amino group is ammonia, a primary or secondary amine, or an amino acid or a peptide radical, which has been prepared separately according to the method A or B described.

The amino group participating in the reaction in a complementary fragment of a compound according to the invention is preferably present in free form, in particular if the carboxyl group brought to reaction with it is employed in activated form. However, it can also be activated. A reactive form of this type is, for example, an isocyanate or a carbamoyl halide.

If the complementary fragment having a free amino group is ammonia, a mono- or a disubstituted amine, then a reactive form of this amine can also be a corresponding urea.

The process according to the invention is carried out in a manner known per se, the reaction conditions being selected corresponding to the type of carboxyl group activation. Customarily, the process is carried out in the presence of suitable solvents or diluents, if appropriate in the presence of an auxiliary, in a temperature range of $-80°$ C. to $300°$ C., preferably $-30°$ C. to $200°$ C., at normal pressure. It is also possible to work at elevated or reduced pressure.

The preparation of the compound according to the invention has also been carried out by other customary variants of the process described (cf., for example, Houben-Weyls "Methoden der organischen Chemie" (Methods of Organic Chemistry) XV/1 and 2; M. Bodanszky, A. Bodanszky in "The Practice of Peptide Synthesis", Springer Verlag, Berlin, 1984; George R. Pettit in "Synthetic Peptides", Volume 4, Elsevier Scientific Publishing Company, Amsterdam-Oxford-New York, 1976; E. Gross and J. Meienhofer (Editors) in "The Peptides", Vol. 1-3, Academic Press, New York-London-Toronto-Sydney-San Francisco, 1981; M. Bodanszky in "Principles of Peptide Synthesis", Spinger Verlag, Berlin-Heidelberg-New York-Tokyo, 1984; R. Uhmann and K. Radscheit, Laid-Open Application, DE 3,411,244 Al) or also by the "Solid-Phase Method" as is described, for example, by M. Bodanszky, A. Bodanszky in "The Practice of Peptide Synthesis", Springer-Verlag, Berlin, 1984, or G. Barany, R.B. Merrifield in "Solid-Phase Peptide Synthesis" from "The Peptides", Vol. 2, pp. 3-254, edited by E. Gross, J. Meienhofer, Academic Press, New York-London-Toronto-Sydney-San Francisco (1980).

The hydrolysis of the carboxylic acid esters is carried out by customary methods, by treating the esters with customary bases in inert solvents, it being possible to convert the salts initially formed into the free carboxylic acids by treating with acid.

Suitable bases for the hydrolysis are the customary inorganic bases. These preferably include alkali metal hydroxides or alkaline earth metal hydroxides such as, for example, sodium hydroxide, potassium hydroxide or barium hydroxide or alkali metal carbonates such as sodium carbonate or hydrogen carbonate or potassium carbonate or hydrogen carbonate, or alkali metal alkoxides such as sodium methoxide, sodium ethoxide, potassium methoxide, potassium ethoxide or potassium tert.-butoxide. Sodium hydroxide or potassium hydroxide are particularly preferably employed.

Suitable solvents for the hydrolysis are water or the organic solvents customary for a hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to employ mixtures of the solvents mentioned.

The hydrolysis is in general carried out in a temperature range from 0° C. to +100° C., preferably from +20° C. to +80° C.

In general, the hydrolysis is carried out at normal pressure. However, it is also possible to work at reduced pressure or at elevated pressure (for example from 0.5 to 5 bar).

When carrying out the hydrolysis, the base is in general employed in an amount of 1 to 3 moles, preferably 1 to 1.5 moles, relative to 1 mole of the ester or the lactone. Molar amounts of the reactants are particularly preferably used.

The cleavage of the ester can additionally be carried out by customary methods using acids, such as, for example, hydrochloric acid or trifluoroacetic acid in the case of the tert.-butyl ester or by hydrogenolysis in the presence of catalysts such as, for example, Pd-carbon or Pt-carbon in the case of the benzyl ester.

The cleavage of the substituted oxazolidin-2-one ring (group Y) from the compounds of the general formula (III) is carried out in one of the abovementioned inert solvents or water, preferably in mixtures of ethers with water, for example tetrahydrofuran/water with hydrogen peroxide and alkali metal hydroxides, preferably with lithium hydroxide, by a known method, (cf. D.A. Evans, T.C. Britton, J.R. Ellman, THL., Vol. 28, No. 49, pp. 6141–6144, 1987).

The compounds of the general formula (II) are new and can be prepared by a process in which compounds of the general formula (V)

in which
$R^1$, W and m have the abovementioned meanings, are condensed with compounds of the general formula (VI)

in which
L has the abovementioned meaning,
in one of the abovementioned inert solvents, if appropriate in the presence of a base.

The reaction can be illustrated by the following equation.

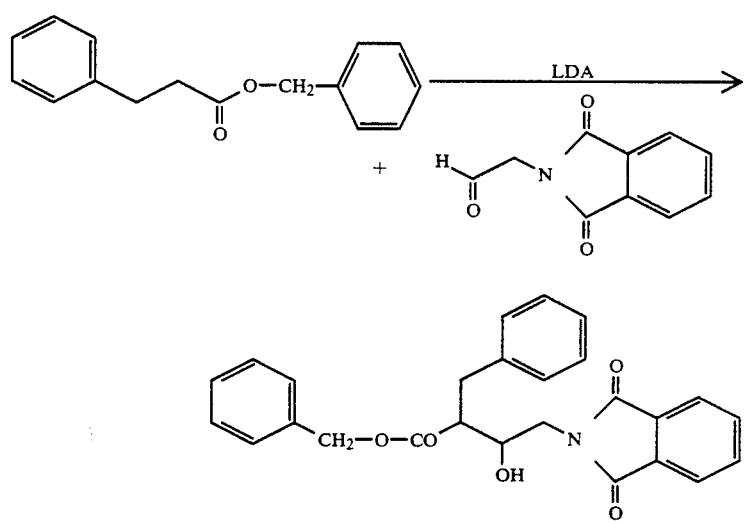

Suitable solvents for the condensation are the abovementioned inert solvents; ethers such as diethyl ether, dioxane or tetrahydrofuran are preferred.

Suitable bases for the condensation are alkali metal hydroxides, boron alkyls, alkali metal amides or organometallic compounds, such as, for example, lithium diisopropylamide, dibutylborane triflate, sodium bis(trimethylsily)amide or sodium hydride.

The condensation may optionally take place via chiral enolates according to a known method (cf. D.A. Evans, T.C. Britten, J. Am. Chem. Soc. 1987, 109, 6881–6883, J. Am. Chem. Soc. 1981, 103, 2172–2129).

The reaction takes place in a temperature range of −80° C. to +30° C., preferably at −70° C. to 0° C., at normal pressure.

The compounds of the general formula (V) are known per se or can be prepared by a customary method (cf. Beilstein 21, 481, Beilstein 9, 511 and J. March, Advanced Organic Chemistry, Second Edition 1977)).

The compounds of the general formula (VI) are in some cases known or are new.

They are new in the cases in which $R^2$ represents the benzyl group or the tert.-butyl group and $R^3$ represents the abovementioned radical $-COR^9$, in which $R^9$ has the meaning indicated there.

They can be prepared either by reacting the corresponding alcohols with the customary oxidizing agents, preferably pyridinium chlorochromate, or reducing the corresponding esters in one of the abovementioned solvents at room temperature using the customary reducing agents, for example diisobutylaluminum hydride, according to a known method.

The compounds of the general formula (III) are also new and can be prepared by reacting compounds of the general formula (VII)

in which

Y, $R^1$ and m have the abovementioned meanings, with compounds of the general formula (VI) by the abovementioned method.

The group Y in the compounds of the general formula (IV) functions as a chiral auxiliary reagent, i.e. the prescribed configuration in the respective oxazolidin-2-one ring stereoselectively induces the corresponding configuration in the abovementioned stereocenters 2 and 3 in the compounds of the general formula (III) and thus also in the compounds of the general formula (I) according to the invention.

Additionally, it is possible to separate steroisomer mixtures, in particular diastereomer mixtures, into the individual isomers in a manner known per se, for example by fractional crystallization, chromatography or Craig partition (compare "Partition Methods in the Laboratory", E. Hecker, Verlag Chemie GmbH, Weinheim, Bergstr. (1955)).

Racemates can be resolved in a manner known per se, for example by converting the optical antipodes into diastereomers.

The compounds of the general formula (VII) are known per se or can be prepared by a customary method (compare J.J. Plattner et al; J. Med. Chem. 1988, 31, (12), 2277-2288).

The amino acids employed as starting materials in the definition of A, B, D and E and thus also the compounds of the general formula (IV) are known per se or can be prepared by a known method or are natural amino acids [Houben-Weyl; "Methoden der organischen Chemie" (Methods of Organic Chemistry), Volume XVI 1 and 2].

Salts of the compounds according to the invention with salt-forming groups can be prepared in a manner known per se, for example by reacting the compounds according to the invention which contain acidic groups with corresponding acids, in each case preferably with the previously mentioned bases or acids.

The compounds according to the invention, in particular those containing D-amino acids, surprisingly have a circulation-influencing effect. They can therefore be employed in medicaments for the treatment of high blood pressure and cardiac insufficiency.

In vitro test

The inhibitory potency of the peptides according to the invention against endogenous renin from human plasma is determined in vitro. Pooled human plasma is obtained with the addition of ethylenediaminetetraacetic acid (EDTA) as anticoagulant and stored at $-20°$ C. The plasma renin activity (PRA) is determined by incubation at 37° C. as the rate of formation of angiotensin I from endogenous angiotensinogen and renin. The reaction solution contains 150 μl of plasma, 3 μl of 6.6% strength 8-hydroxyquinoline sulphate solution, 3 μl of 10% strength dimercaprol solution and 144 μl of sodium phosphate buffer (0.2M; 0.1% EDTA; pH 5.6) with or without the substances according to the invention in various concentrations. The angiotensin I formed per unit of time is determined by radioimmunoassay (Sorin Biomedica, Italy).

The percentage inhibition of the plasma renin activity is calculated by comparison of the instant novel substances. The concentration range in which the novel substances show a 50% inhibition of the plasma renin activity are between $10^{-4}$ and $10^{-9}$M.

| Example No. | Inhibition at 0.05 mg/ml [%] |
|---|---|
| 70 | 100 |
| 71 | 92 |
| 72 | 100 |
| 74 | 93 |
| 75 | 65 |
| 76 | 78 |
| 77 | 100 |
| 78 | 100 |
| 82 | 100 |
| 83 | 100 |
| 85 | 60 |
| 86 | 80 |
| 88 | 100 |
| 89 | 100 |
| 90 | 63 |
| 92 | 100 |
| 93 | 100 |
| 95 | 100 |
| 103 | 88 |
| 105 | 100 |
| 108 | 100 |
| 107* | 100 |

The IC$_{50}$ value of Example 107 was determined as $4.3 \cdot 10^{-8}$M.

The IC$_{50}$ value of Example 169 was determined as $9.6 \cdot 10^{-9}$M.

The new active compounds can be converted in a customary manner into the customary formulations, such as tablets, coated tablets, pills, granules, aerosols, syrups, emulsions, suspensions and solutions, using inert, non-toxic, pharmaceutically suitable excipients or solvents. In this connection, the therapeutically active compound should in each case be present in a concentration of from about 0.5 to 90% by weight of the total mixture, i.e. in amounts which are sufficient in order to achieve the dosage range indicated.

The formulations are prepared, for example, by extending the active compounds with solvents and/or excipients, optionally using emulsifiers and/or dispersants, it being possible, for example, in the case of the use of water as diluent, to use, if appropriate, organic solvents as auxiliary solvents.

Examples of auxiliary solvents which may be mentioned are: water, non-toxic organic solvents, such as paraffins (for example mineral oil fractions), vegetable oils (for example groundnut/sesame oil), alcohols (for example: ethyl alcohol, glycerol), excipients, such as, for example, ground natural minerals (for example kaoline, aluminas, talc, chalk), ground synthetic minerals (for example highly disperse silica, silicates), sugars (for example sucrose, lactose and dextrose), emulsifiers (for example polyoxyethylene fatty acid esters), polyoxyethylene fatty alcohol ethers (for example ligninsulphite waste liquors, methyl cellulose, starch and polyvinylpyrrolidone) and lubricants (for example magnesium stearate, talc, stearic acid and sodium sulphate).

Administration is carried out in a customary manner; preferably orally or parenterally, in particular perlingually or intravenously. In the case of oral administration, in addition to the excipients mentioned, tablets may of course also contain additions, such as sodium citrate, calcium carbonate and dicalcium phosphate together with various additives, such as starch, preferably potato starch, gelatine and the like. Furthermore, lubricants, such as magnesium stearate, sodium lauryl sulphate and talc may additionally be used for tabletting. In the case of aqueous suspensions, various flavor enhancers or colorants may be added to the active compounds in addition to the abovementioned auxiliaries.

In the case of parenteral administration, solutions of the active compounds using suitable liquid excipient materials may be employed.

In general, it has proved advantageous on intravenous administration to administer amounts of about 0.001 to 1 mg/kg, preferably about 0.01 to 0.5 mg/kg of body weight to attain effective results, and on oral administration the dosage is about 0.01 to 20 mg/kg, preferably 0.1 to 10 mg/kg of body weight.

In spite of this, it may sometimes be necessary to deviate from the amounts mentioned, in particular depending on the body weight of the experimental animal or the type of administration, but also on the basis of the animal species and its individual behavior towards the medicament or the nature of its formulation and the point in time or interval at which administration takes place. Thus, in some cases it may be sufficient to manage with less than the minimum amount previously mentioned, while in other cases the upper limits mentioned must be exceeded. In the case of the administration of relatively large amounts, it may be advisable to divide these into a number of individual doses over the day. For administration in human medicine, the same dosage range is intended. Accordingly, the above embodiments also apply in this case.

Explanations for the experimental section:
TLC systems
Stationary phase
Merck prepared TLC plates silica gel 60 F-254, 5×10 cm, layer thickness 0.25 mm, article No. 5719.

| Mobile phases (as "TLC system" in the test) |
|---|
| I: $CH_2Cl_2$/MeOH 9:1 |
| II: $CH_2Cl_2$/MeOH 95:5 |
| III: $NH_3$/$CH_2Cl_2$/MeOH 0.2:9:1 |
| IV: acetic acid/$CH_2Cl_2$/MeOH 0.2:9:1 |
| V: glacial acetic acid/n-butanol/$H_2O$ 1:3:1 |
| VI: EtOAc/n-hexane 2:1 |
| VII: EtOAc/n-hexane 1:3 |

| -continued |
|---|
| Mobile phases (as "TLC system" in the test) |
| VIII: Et-OAc/n-hexane 1:1 |
| IX: $CH_2Cl_2$/MeOH 98:2 |
| X: $CH_2Cl_2$/MeOH 7:3 |
| XI: $CH_2Cl_2$ |
| XII: toluene/EtOAc 4:1 |
| XIII: $CH_2Cl_2$/n-hexane 4:1 |
| XIV: $CH_2CO_2$/n-hexane 9:1 |
| XV: EtOAc/n-hexane 1:5 |
| XVI: EtOH/$H_2O$ 3:1 |

HPLC systems:
HPLC system I; Merck column, Lichrosorb [R]. RP-8, 250-4, 10 μm, Cat. No. 50318.
HPLC system II: Merck column, Lichrosorb [R]. RP-18, 250-4, 10 μm, Cat. No. 50334.
Eluents for system I and II
A: pH 7.00 phosphate buffer, Merck, article No. 9439/$H_2O$ 1:50.
B: acetonitrile.
A/B as 1/1, flow rate: 2 ml/min, isocratic.
Detection: 254 nm.
HPLC system III: Nucleosil 120-5 C 18 column, 5 μm, 125×4 mm eluents;
A=0.01M $H_3PO_4$, B=acetonitrile.
Eluent program:
0-1 min: 10% B.
1-9 min: gradient of 10% B/min.
9-13 min: 90% B.
flow rate: 2 ml/min, room temperature.
5 μl, sample quantity about 1 mg/ml.
detection: UV diode array at 210 nm.
HPLC system IV: Chiral AG P column. manufacturer: Chrome-Tech AB/Stockholm mobile phase: 0.02M phosphate pH=6.5 and 8% acetonitrile, room temperature, pressure 42 bar, flow rate 0.5 ml/min, DET 225 nm.
HPLC system V: Nucleosil 120-5 $C_{18}$ column mobile phase, phosphate buffer, acetonitrile 45:55, isocratically mixed, temp. 35° C. flow rate 2 ml/min.
HPLC system VI: Lichrosorb RP 8 column, 5 μm; phosphate pH 7, 1:10 dilution; acetonitrile 45:55.
HPLC system VII (chiral): Column: as for HPL system IV; mobile phase: eluent A=1.2 g $NaH_2PO_4$ and 0.2 g $Na_2HPO_4$/1 1 $H_2O$; eluent B=acetonitrile; A:B=96:4; all other parameters as under IV.
GC system I (chiral): Column 264=25M cyclohexylglycine t-butylamide, oven: 80°-200° C.; 4° C./min. 0.4 bar hydrogen, split inj.: 230° C., FID det: 280° C., GC: 4*10. injection: microliters of solution.

List of abbreviations used
1. General analytical methods
TLC: thin-layer chromatography
PTLC: preparative thick-layer chromatography
GC: gas chromatography
HPLC: high pressure liquid chromatography
CC: column chromatography
NMR: nuclear spin resonance spectroscopy (protons)
MS: mass spectrometry (electron impact ionization)
(+)FAB-MS: fast atom bombardment mass spectrometry, positive ions, matrix substance: m-nitrobenzyl alcohol
MS-DCL: mass spectrometry, chemical ionization
2. Amino acids
In general, the configuration is indicated by placing an L or D in front of the amino acid abbreviation, and in the case of the racemate a D,L-, where, for simplification, with L-amino acids the configuration notation can be omitted and then explicit notation only occurs in the case of the D-form or the D,L-mixture.

a) Naturally occurring amino acids
Ala: L-alanine
Arg: L-arginine
Asn: L-asparagine
Asp: L-aspartic acid
Cys: L-cysteine
Glyn: L-glutanmine
Glu: L-glutamic acid
Gly: L-glycine
His: L-histidine
Ile: L-isoleucine
Leu: L-leucine
Lys: L-lysine
Met: L-methionine
Orn: L-ornithine
Phe: L-phenylalanine
Ser: L-serine
Sar: L-sarcosine (N-methylglycine)
Thr: L-threonine
Trp: L-trypotophan
Tyr: L-tyrosine
Val: L-valine b) Non-naturally occurring amino acids
D- or L-Nal(1): β-(1-naphthyl)-D- or -L-alanine
D- or L-Nal(2): β-(2-naphthyl)-D- or -L-alanine
D- or L-Phg: D- or L-phenylglycine
D- or L-Pyr(2): β-(2-pyridyl)-D- or -L-alanine
D- or L-Pyr(3): β-(3-pyridyl)-D- or -L-alanine
D- or L-Pyr(4): β-(4-pyridyl)-D- or -L-analine
D- or L-Trz(1): β-(1-triazolyl)-D- or -L-alanaline
D- or L-Phe(4I): β-(4-iodophenyl)-D- or -L-alanine
D- or L-Phe(4OCH3): β-(4-methoxyphenyl)-D- or -L-alanine 3. Activating groups
HOBT: 1-hydroxybenzotriazole
HOSU: N-hydroxysuccinimide 4. Coupling reagents
DCC: dicyclohexylcarbodiimide
DPPA: diphenylphosphoryl azide
PPA: n-propanephosphonic anhydride
BOP: benzotriazolyloxy tris(dimethylamino)phosphonium hexafluorophosphate
WSC: N-(3-dimethylaminopropyl)-N'-ethylcarbodiimide hydrochloride 5. Reagents
NEM: N-ethylmorpholine
NMM: N-methylmorpholine
DIPEA: diisopropylethylamine
TEA: triethylamine
TFA: trifluoroacetic acid 6. Solvents
HOAc: acetic acid
DMF: dimethylformamide
EtOAc: ethyl acetate
MeOH: methanol
EtOH: ethanol
THF: tetrahydrofuran
DMSO: dimethyl sulphoxide
HMPA: hexamethylphosphoramide 7. Protecting groups
Boc: tert-butoxycarbonyl
Z: benzyloxycarbonyl
DNP: dinitrophenyl
Fmoc: 9-fluorenylmethoxycarbonyl
OEt: ethyl ester
OMe: methyl ester 8. Others
DCU: N,N'-dicyclohexylurea

EXAMPLE I

Benzyl 3-phenylpropionate

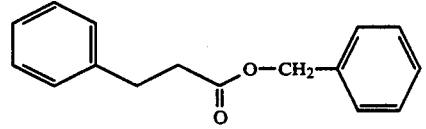

485 g (3.23 mol) of 3-phenylpropionic acid and 440 ml (4.25 mol) of benzyl alcohol are dissolved in 4 l of dichloromethane. After adding 4 g (0.0323 mol) of dimethylaminopyridine, the mixture is cooled to 5° C. and a solution of 732 g (3.55 mol) of dicyclohexylcarbodiimide is added dropwise with stirring at this temperature.

The suspension is allowed to come to room temperature overnight. The precipitated dicyclohexylurea is filtered off with suction and 75 g (1 mol) of glycine are added to the filtrate. After stirring at room temperature for 3 hours, the residue is filtered off and the organic solvent is stripped off in vacuo. The residue is distilled in a high vacuum.

Yield: 476 g of yellow oil (61% of theory).
m.p.: 145°–148° C. at 1 mbar.
MS-EI: 240 ($M^{30}$).

EXAMPLE II

N-tert.-Butoxycarbonyl-N-benzyl-glycine ethyl ester

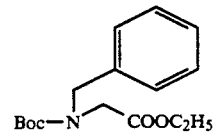

300 g (1.552 mol) of N-benzylglycine ethyl ester (Aldrich) and 236 ml (1.707 mol) of triethylamine are dissolved in 1200 ml of tetrahydrofuran. A solution of 338.3 g (1.552 mol) of di-tert.-butyl dicarbonate (Fluka) in 300 ml of dichloromethane is added dropwise to the stirred mixture with ice cooling. The mixture is subsequently stirred overnight and the mixture is allowed to come to room temperature in the course of this.

The mixture is adjusted to pH 3 with half-concentrated hydrochloric acid and is freed form organic solvent in a rotary evaporator at a bath temperature of 30° C. The residue is made up with water and then extracted three times with 1 l of ethyl acetate each time. The purified organic phases are washed with saturated sodium chloride solution, dried over sodium sulphate, filtered and concentrated on a rotary evaporator.

The residue is dissolved several times using dichloromethane to remove residual amounts of ethyl acetate, the solutions are concentrated in a rotary evaporated and the residue is dried in a high vacuum.

Yield: 464 g (100% of theory).
TLC system II: Rf=0.94.
HPLC system II: Rt=10.54 min.

EXAMPLE III

N-tert.-Butoxycarbonyl-N-benzyl-ethanolamine

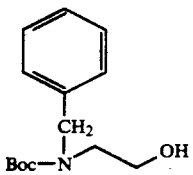

189 g (0.644 mol) of the compound from Example II are initially introduced in 1.8 l of dry tetrahydrofuran. 97.4 g (2.58 mol) of sodium borohydride are added in portions with stirring.

At a gentle reflux (bath temperature 50° C.), 900 ml of methanol p.A. are cautiously added dropwise to the mixture in the course of 1 hour. The mixture is heated overnight to reflux, cooled and adjusted to pH 6 with half-concentrated hydrochloric acid. The organic solvents are evaporated in a rotary evaporated. The residue is made up with water and extracted three times using 1 l of diethyl ether each time. The combined organic phases are washed with hydrochloric acid of pH 3, saturated bicarbonate solution and saturated sodium chloride solution, dried over sodium sulphate, filtered and concentrated.

Yield: 144.4 g (89.2% of theory).
TLC system: Rf=0.49.
TLC system: VIII: Rf=0.53.
(+)FAB-MS: m/e 252 (M+H).

EXAMPLE IV

N-tert.-Butoxycarbonyl-N-benzyl-glycine aldehyde

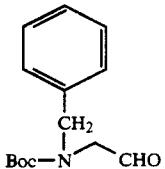

Variant A 14.65 g (58.3 mmol) of the compound from Example III and 37.3 g (175 mmol) of pyridinium chlorochromate (Aldrich) are added to 500 ml of dichloromethane and the mixture is stirred at room temperature for 2 hours.

The mixture is concentrated in a rotary evaporator and quickly filtered through a frit using 600 g of silica gel 60 (Merck) and a step gradient of 1 l of dichloromethane, 1 l of dichloromethane/methanol 98/2 and 1.5 l of dichlormethane/methanol 95:5. 500 ml fractions were taken, and the product-containing eluates were combined, dried over sodium sulphate and concentrated in a rotary evaporator.

Yield: 4 g 27.5% of theory).

Variant B 270 g (0.92 mmol) of the compound from Example II are dissolved in 2 l of dry tetrahydrofuran and 1.84 l of 1N diisobutylaluminum hydride solution in hexane (Aldrich) are added dropwise under nitrogen and with stirring at −60° C. The mixture is subsequently stirred at this temperature for 35 minutes and then hydrolyzed using 5 l of 1M aqueous potassium sodium tartrate solution, strong foaming initially occurring The mixture is subsequently stirred at room temperature for 1 hour, 1 l of diethyl ether is added and the organic phase is separated off. The aqueous phase is extracted twice with 1 l of diethyl ether each time. The combined organic phases are washed with saturated sodium chloride solution, dried over sodium sulphate, filtered and concentrated to dryness.

The crude product (234 g) is chromatographed on 3.8 kg of silica gel 60 (Merck, article No. 9385), 0.040–0.063 mm (230–400 mesh) and a step gradient of 20 l of dichloromethane/methanol 99:1, 2 l of dichloromethane/methanol 98.5:1.5, 2 l of dichloromethane/methanol 97/3, 5 l of dichloromethane/methanol 9:1 and 4 l of dichloromethane/methanol 8:2. After combining and concentrating the product-containing fraction, the aldehyde is dried in a high vacuum.

Yield: 88.7 g (38.7% of theory).
TLC system IX: Rf=0.55
TLC system XI: Rf=0.50.
TLC system XIII: Rf=0.19.
TLC system XIV: Rf=0.40.
(+)FAB-MS: m/e 250 (M+H).

EXAMPLE V

N-Methyloxycarbonyl-D-valinol

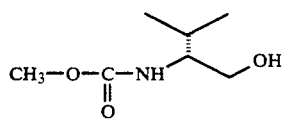

39.7 g (0.385 mol) of D-valinol (Aldrich) are dissolved under nitrogen in 500 ml of dry THF. 58.7 ml (0.424 mol) of triethylamine are added, the mixture is cooled to −20° C. and 32.8 ml (0.424 mol) of methyl chloroformate (Aldrich) are added dropwise to the mixture with stirring. The mixture is subsequently stirred at this temperature for 30 minutes and then brought to room temperature. 60 g (0.078 mol) of glycine are added and the mixture is stirred once more for 15 minutes. The precipitate is filtered off with suction, the filtrate is concentrated and the residue is taken up in diethyl ether. The organic phase is washed with 1N HCl, saturated NaHCO₃ solution and saturated sodium chloride solution, dried over sodium sulphate, filtered and concentrated, and the residue is dried in a high vacuum.

Yield: 27.7 g (45% of theory).
TLC system I: Rf=0.59.
MS-EI: m/e 162 (M+).

EXAMPLE VI (4R)-4-(2-Propyl)oxazolidin-2-one

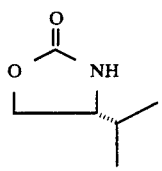

27.2 g (168.7 mmol) of the compound from Example V are dissolved in 400 ml of toluene and stirred under reflux in an oil bath at 150° C. while passing in nitrogen.

100 ml of damp toluene are separated off using a water separator. The mixture is cooled to 100° C. and 1.5 g of finely ground and vacuum-dried potassium carbonate are added. The temperature is increased to 120° C. After about 15 minutes, the mixture foams spontaneously, methanol (b.p. 64° C.) being removed by distillation (7.5 ml, calc. amount 6.8 ml). A further 70 ml of toluene are then removed by distillation at a bath temperature of 140° C. The mixture is filtered off hot from K$_2$CO$_3$ and concentrated in vacuo. The crystalline residue is triturated with 50 ml of n-hexane, filtered off with suction and dried in a high vacuum.

Yield: 19.8 g (91% of theory).
m.p.: 71° C. (lit. 71°–72° C.).
TLC system IX: Rf>0.40.
MS-EI: m/e 129 (M+).
GC system I: Rt=28.389 min., isomerically pure; compare S-enantiomer (Fluka): Rr=28.884 min.

EXAMPLE VII (4R)-3-(3-Phenylpropionyl)-4-(2-propyl)oxazolidin-2-one

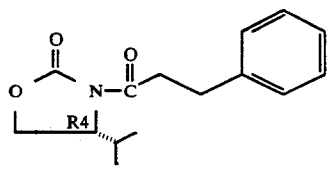

The title compound is prepared according to the process described for the S-enantiomer (J.J. Plattner et al., J. Med. Chem. 1988, 31 (12), 2277–2288), starting from 19.4 g of the compound of Example VI and 25.3 ml (170 mmol) of 3-phenylpropionyl chloride.

Yield: 34 g (87.4% of theory).
m.p.: 62° C. (lit. 86.5°–87.5° C.; the S-enantiomer was prepared analogously and also had a melting point of 62° C.).
TLC system XI: Rf=0.63.
HPLC system II: Rt=7.16 min.
MS-EI: m/e 261 (M+).

EXAMPLE VIII (4R,5S)-3-(3-Phenylpropionyl)-4-methyl-5-phenyl-oxazolidin-2-one

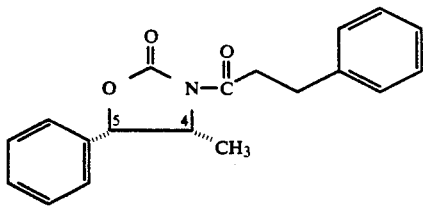

The title compound is obtained analogously to Example VII from 25.1 g (141.6 mmol) of 4R,5S-4-methyl-5-phenyl-oxazolidin-2-one (Fluka) and 23.8 ml (142.4 mmol) of phenylpropionyl chloride.

Yield: 40.3 g (92% of theory).
m.p.: 96° C. (from ether/n-hexane).
TLC system XI: Rf=0.70.
HPLC system II: Rt=12.72 min.
MS-DCI: m/e 310 (M+H).

EXAMPLE IX (4S)-3-(3-Phenylpropionyl)-4-phenyloxazolidin-2-one

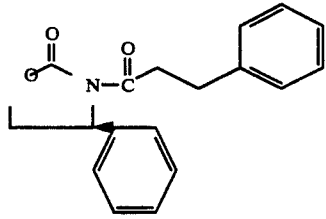

The title compound is obtained analogously to Example VII from 19.75 g (121 mmol) of (4S)-4-phenyloxazolidin-2-one (Fluka) and 19.8 ml (133 mmol) of phenylpropionyl chloride.

Yield: 34.6 g (97% of theory).
m.p.: 130°–131° C. (from ether/n-hexane).
TLC system XI: Rf=0.57.
HPLC system II: Rt=7.26 min.
MS-EI: m/e 295 (M+).

EXAMPLE X (4R)-3-(3-Phenylpropionyl)-4-benzyloxazolidin-2-one

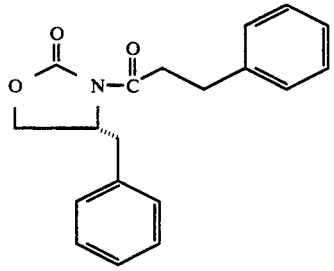

The title compound is obtained analogously to Example VII from 25.45 g (143.6 mmol) of (4R)-benzyloxazolidin-2-one (Fluka) and 23.5 ml (158 mmol) of phenylpropionyl chloride.

Yield: 40.2 g (95% of theory).
m.p.: 107°108° C. (from ether/n-hexane).
TLC System XI: Rf=0.81.
HPLC system II: Rt=9.55 min.
MS-EI: m/e 309 (M+).

EXAMPLE XI AND EXAMPLE XII (4S)-3-[(2R)-2-Benzyl-(3S)-3-hydroxy-3-phenylpropionyl]-4-(2-propyl)-oxazolidin-2-one (Example XI)

(4S)-3-[(2R)-2-Benzyl-(3R)-3-hydroxy-3-phenylpropionyl]-4-(2-propyl)-oxazolidin-2-one (Example XII)

Example XI

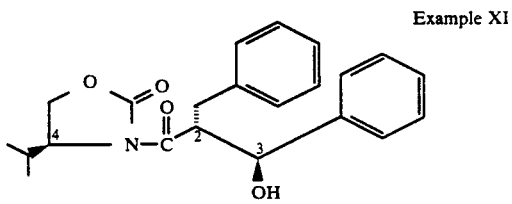

Example XII

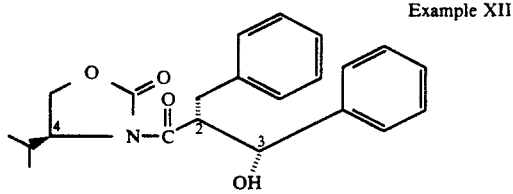

1.55 ml (11 mmol) of diisopropylamine is dissolved in 20 ml of absolute THF under argon and 7.75 ml (12 mmol) of n-butyllithium solution (1.55M in n-hexane, Aldrich) are added at −20° C. with stirring. The mixture is stirred at this temperature for 10 minutes and the freshly prepared solution of lithium diisopropylamide prepared in this way is then added dropwise to a solution of 2.61 g (10 mmol) of (4S)-3-(3-phenylpropionyl)-4-(2-propyl)-oxazolidin-2-one (J.J. Plattner et al., J. Med. Chem. 1988, 31 (12), 2277-2288) cooled to −70° C. in 30 ml of absolute THF. The mixture is subsequently stirred at −70° C. for 30 minutes and 1.32 ml (13 mmol) of benzaldehyde are injected into the mixture via a septum. After one hour at this temperature, the mixture is hydrolyzed by adding 100 ml of saturated ammonium chloride solution and allowed to come to room temperature, and 100 ml of diethyl ether are added. The organic phase is separated off and the aqueous phase is extracted with 100 ml of diethyl ether.

The combined organic phase is washed with 1N HCl, saturated sodium hydrogen carbonate solution and saturated sodium chloride solution, dried over Na$_2$SO$_4$ and concentrated.

The crude product (34 g) is chromatographed on 150 g of silica gel 60 (Merck) 40 to 63 nm using dichloromethane as the eluent. The product-containing eluates are collected and concentrated. The crystalline fractions are triturated with n-hexane, filtered off with suction and dried.

Yield: 1.46 g of Example XI. 0.13 g of mixed fraction. 0.53 g of Example XII.

Total yield: 2.12 g (57% of theory).

Structure Assignment Example XI

Single crystals of Example XI were obtained from ether/n-hexane and subjected to an X-ray structural analysis. Accordingly, the indicated 4S, 2R, 3S-configuration belongs to Example XI:

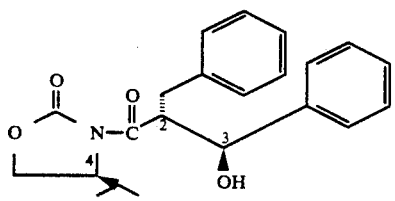

Structure Assignment Example XII

The compound was assigned the 4S, 2R, 3R-configuration by X-ray structural analysis of the mirror image isomer (Example XIV).

Analytical data (Example XI, 4S, 2R, 3S-isomer)
m.p.: 82° C.
TLC system XI: Rf=0.28.
HPLC system II: Rt=8.97 min.
HPLC system III: Rt=7.287 min.; retention index 895.
(+)FAB-MS; m/e 368 (M+H); m/e 390 (M+Na).
Analytical data (Example XII, 4S, 2R, 3R-isomer)
m.p.: 160° C.
TLC system XI: Rf=0.16.
HPLC system II: Rt=6.61 min.
HPLC system III: Rt=6.948 min.; retention index 847.
(+)FAB-MS: m/e 368 (M+H); m/e 390 M+Na).

EXAMPLE XIII AND EXAMPLE XIV (4R)-3-[(2S)-2-Benzyl-(3R)-3-hydroxy-3-phenylpropionyl]-4-(2-propyl)-oxazolidin-2-one (Example XIII)

(4R)-3-[(2S)-2-Benzyl-(3S)-3-hydroxy-3-phenylpropionyl]-4-(2-propyl)-oxazolidin-2-one (Example XIV)

Example XIII

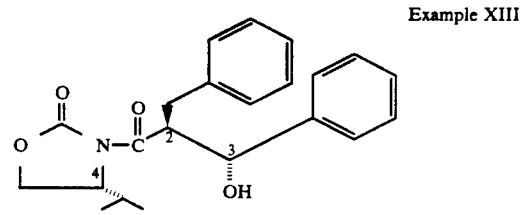

Example XIV

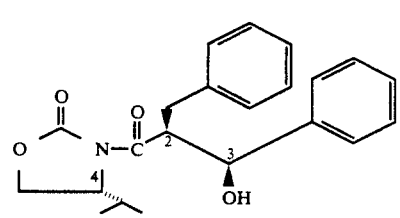

The title compounds are obtained isomerically pure analogously to Example XI and XII by reaction of the lithium anion of (4R)-3-(3-phenylpropionyl)-4-(2-propyl)-oxazolidin-2-one (Example (VII)) with benzaldehyde and chromatography of the crude product.

Structure Assignment a) Example XIII

The compound was assigned the 4R, 2S, 3R-configuration by X-ray structural analysis of the mirror image isomer of Example XI.

b) Example XIV

Single crystals of Example XIV were obtained from ether/n-hexane and subjected to an X-ray structural analysis. Accordingly, the 4R, 2S, 3S-configuration indicated belongs to the compound.

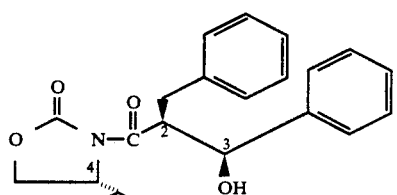

The analyzed data (TLC, HPLC and FAB) of Example (XIII) are identical to those of Example XI. The analyzed data (TLC, HPLC and FAB) of Example XIV are identical to those of Example XII.

EXAMPLE XV (4R)-3-(3-Cyclohexylpropionyl)-4-benzyloxazolidin-2-one

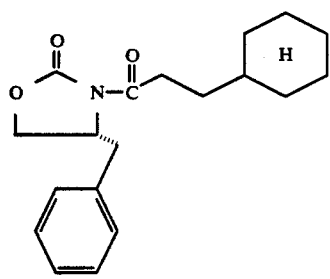

The title compound is obtained analogously to Example X from 21.09 g (119 mmol) of (4R)-benzyloxazolidin-2-one (Fluka) and 22.8 g (22 ml, 130.6 mmol) of cyclohexylpropionyl chloride (3-cyclohexylpropionyl chloride (3-cyclohexylpropionic acid, SOCl₂, Δ; distillation; b.p. 0.3 mbar; 44° C.)).

Yield: 33.2 g (88.4% of theory).
m.p.: 88° C.
TLC system XI: Rf=0.63.
HPLC system II: Rt=28.96 min.
MS-DIC: m/e 316 (M+H).

EXAMPLE XVI (1-L-Carbethoxy)ethyl 3-phenylpropionate

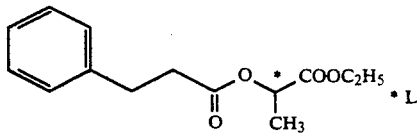

The title compound is obtained analogously to Example I by reacting 37.24 g (0.25 mol) of 3-phenylpropionic acid and 26.4 g (0.22 mol) of ethyl L-(−)-lactate in 600 ml of CH₂Cl₂ with 41.26 g of DCC and 0.25 g of DMAP. The precipitated dicyclohexylurea (DCU) is filtered off with suction, and the organic phase is shaken with saturated sodium bicarbonate solution, dilute hydrochloric acid and saturated sodium chloride solution, dried over sodium sulphate and concentrated.

Yield: 47.5 g (77% of theory).
TLC system XI: Rf=0.71.
MS-EI: m/e 240 (M+).

¹H-NMR (300 MHz, CDCl₃): δ=7.22 (m, 5H); 5.06 (q, 1H); 4.81 (q, 2H); 2.98 (m, 2H); 2.71 (m, 2H); 1.45 (d, 3H); 1.25 (t, 3H).

EXAMPLE XVII (1-S-Carbethoxy)benzyl 3-phenylpropionate

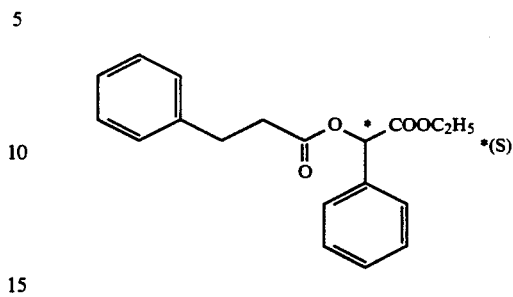

The title compound is obtained analogously to Example XVI from 30 g (0.2 mol) of phenylpropionic acid and 32.4 g (0.18 mol) of ethyl (S)-(+)-mandelate by DCC/DMAP coupling and standard working up.

Yield: 53 g (95% of theory).
TLC system XI: Rf=0.70.
MS-DCI: m/e 313 (M+H); m/e 330 (M+NH₄).

¹H-NMR (250 MHz, DMSO): δ=7.41 (m, 5H); 7.18 (m, 5H); 5.95 (s, 1H); 4.09 (m, 2H); 2.79 (m, 2H); 2.75 (m, 2H); 1.09 (t, 3H).

EXAMPLE XVIII (4S)-3-(3-Cyclohexylpropionyl)-4-benzyloxazolidin-2-one

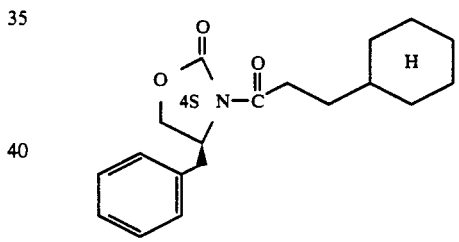

The title compound is obtained analogously to Example XV. (4S)-benzyloxazolidin-2-one (Fluka) is employed in modification.

Analytical data: as under Example XV.

EXAMPLE XIX

N-tert.-Butoxycarbonyl-L-prolinal

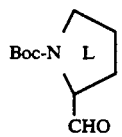

The title compound is obtained starting from N-tert.-butoxycarbonyl-L-proline methyl ester analogously to Example IV, variant B (reduction with DIBAl). Chromatography is dispensed with.

Yield: 52 g (81% of theory).
(+)FAB-MS: m/e 200 (M+H).

PREPARATION EXAMPLES (GENERAL FORMULA I, II AND III)

EXAMPLE I

Benzyl 4-(N-phthalyl)amino-2-R,S-benzyl-3-R,S-hydroxybutyrate

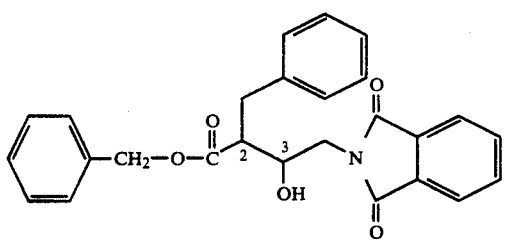

2R,S,3R,S 66.7 ml (0.477 mol) f diisopropylamine are initially introduced into 300 ml of absolute tetrahydrofuran under argon. The solution is cooled to −20° C. and stirred, 330 ml (0.528 mol) of a 1.6 molar solution of n-butyllithium in n-hexane (Aldrich) are added dropwise, and the mixture is subsequently stirred at −20° C. for 30 minutes and then cooled to −70° C. A solution of 114.6 g (0.477 mol) of the compound from Example I is added dropwise at this temperature and the mixture is subsequently stirred for 30 minutes. The clear yellow solution thus obtained is added at −70° C. and under argon in the course of 60 hours to a solution of 82.2 g (0.434 mol) of N-phthalylglycine aldehyde (CA 2913-97-5) in 300 ml of absolute tetrahydrofuran. The mixture is subsequently stirred for 60 minutes, the temperature is allowed to come to 0° C. and the mixture is hydrolyzed with 0.62 l of 1N HCl.

The mixture is poured into a separating funnel and allowed to come to room temperature overnight. The organic phase is separated off. The aqueous phase is adjusted to pH 3 and extracted twice and 7 l of diethyl ether each time. The combined organic phases are each washed once with saturated sodium hydrogen carbonate solution, 0.1N hydrocloric acid and saturated sodium chloride solution, dried over sodium sulphate, filtered and concentrated in a rotary evaporator.

The crude product (113 g of yellow oil) is filtered through silica gel 60 (Merck, article No. 9385), 0.040-0.063 mm (230-400 mesh) using a step gradient of 2.5 l each of dichloromethane, dichloromethane/methanol 98:2 and dichloromethane/methanol 96:4. The product-containing fractions are combined and concentrated.

Yield: 44 g (23.6% of theory); isomer mixture: according to $^1$H-NMR=4:1.

TLC system I: Rf=0.89.
TLC system XI: Rf=0.14.
TLC system XII: Rt=0.44.
HPCL system II: Rt=10.36 min.
(+)FAB-MS: m/e (M+H); m/e 452 (M+Na).

EXAMPLE 2 AND EXAMPLE 3

Benzyl 4-(N-phthalyl)amino-2S- or 2R-benzyl-3S or 3R-hydroxy-butyrate (Example 2, enantiomer pair of diastereomer A) and benzyl 4-(N-phthalyl)amino-2S- or 2R-benzyl-3R or 3S-hydroxy-butyrate (Example 3, enantiomer pair of diastereomer B)

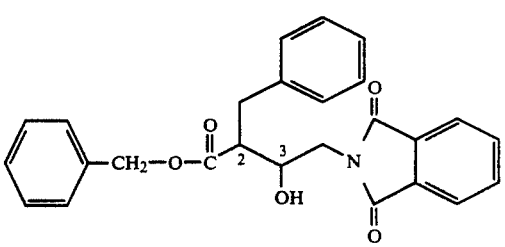

Example 2: 2S, 3S and 2R, 3R;
Enantiomer pair of diastereomer A.
Example 3: 2S, 3R and 2R, 3S;
Enantiomer pair of diastereomer B.

The isomer mixture from Example 1 is separated by column chromatography on 600 g of silica gel 60 (Merck, article No. 9385), 0.040-0.063 mm (230-400 mesh) using a step gradient of 8 l of dichloromethane/n-hexane 4:1, 5 l of dichlormethane/methanol 98:2, 5 l of dichloromethane/methanol 95:5 and 2.5 l of dichloromethane/methanol 9:1. 1 l fractions were taken and the isomer purity was determined by means of the $^1$H-NMR spectra.

The fractions eluted first contain only Example 2 (diastereomer A, $^1$H signal at δ=5.45 ppm in DMSO, Dublett), followed by mixed fractions of Example 2 and Example 3 (diastereomer B, $^1$H signal at δ=5.39 ppm in DMSO, doublet). The mixed fractions eluting last, which predominantly contained Example 3 (diastereomer B) with proportions of Example 2 (diastereomer A) up to a maximum of 30%, were combined and rechromatographed on silica gel 60. After carrying out the procedure described above, diastereomer B (Example 3) is also obtained in this way. Analytical data: as described under Example 1.

The assignment of the 2S,3S/2R,3R-configuration of Example 2 or the 2S,3R/2R,3S configuration of Example 3 takes place by means of the chemical shift of the hydroxyl doublets on C-3 in the $^1$H-NMR spectrum (DMSO) in comparison to the model compounds of Examples XI/XIII (2R,3S/2S,3R; doublet in each case at δ=5.48 ppm) or of Examples XII/XIV (2R,3R/2S,3S; doublet in each case at δ=5.64 ppm).

EXAMPLE 4

Benzyl 4-(N-tert.-butoxycarbonyl-N-benzyl)amino-2R,S-benzyl-3R,S-hydroxy-butyrate

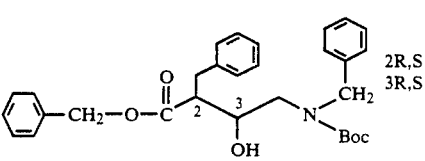

2R,S
3R,S 10.8 ml (77 mmol) of diisopropylamine are initially introduced into 100 ml of absolute THF under argon, the mixture is cooled to −20° C. and 53 ml (85 mmol) of a 15% strength solution of n-butyllithium in hexane are added dropwise with stirring. The mixture is subsequently stirred at this temperature for 30 minutes. It is then cooled to −70° C. and a solution of 18.5 g (77 mmol) of benzyl 3-phenyl-propionate (Example I) in 50 ml of absolute THF is added dropwise. After subsequently stirring at this temperature for 30 minutes, a solution of 17.2 g (69 mmol) of the compound from Example IV in 50 ml of absolute THF is added dropwise into the mixture in the course of 20 minutes. With increasing temperature (removal of the cold bath), the mixture is subsequently stirred for a further hour and then hydrolyzed by adding 170 ml of 1N HCl with cooling in an ice bath.

The mixture is diluted at room temperature with 150 ml of ethyl acetate and the organic phase is separated off. The aqueous phase is extracted twice with 100 ml of ethyl acetate. The combined organic phases are washed with saturated sodium bicarbonate solution and sodium chloride solution, dried over sodium sulphate, filtered and concentrated to dryness.

The crude product (35 g) is chromatographed on 1.7 kg of silica gel 60 (Merck, article No. 9385) 0.040–0.063 mm (230–400 mesh) using a step gradient of 1 l of petroleum ether (PE), 2 l of PE/ethyl acetate (EtOAc) 95:5, 2 l of PE/EtOAc 9:1, 2 l of PE/EtOAc 85:15 and 7 l of PE/EtOAc 8:2. The product-containing fractions are combined, eluent is removed in a rotary evaporator and, to remove residual traces of ethyl acetate, the residue is dissolved and concentrated several times using dichloromethane and finally dried in a high vacuum.

Yield: 11.53 g (34% of theory).
TLC system VII: Rf=0.42.
TLC system IX: Rf=0.79.
TLC system XV: Rf=0.26.
Stereoisomers not clearly distinguishable.
HPLC system II: Rt=50.44 min.
(+)FAB-MS: m/e 490 (M+H).
MS-DCI: m/e 490 (M+H).

A distinction or assignment of the diastereomers cannot be carried out clearly as the $^1$-NMR spectra are complicated by rotational isomers (see $^1$H-NMR spectra of Examples II, III and IV).

EXAMPLE 5

4-(N-Phthalyl)amino-2R,S-benzyl-3R,S-hydroxybutyric acid

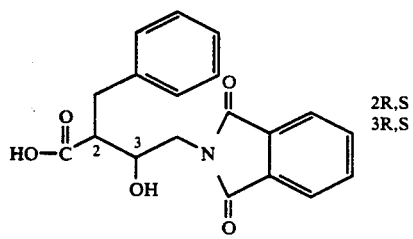

5 g (11.6 mmol) of benzyl 4-(N-phthalyl)amino-2R,S-benzyl-3R,S-hydroxybutyrate (diastereomer mixture from Example 2 and 3 in the ratio 1:1) are dissolved in 100 ml of MeOH and, after adding 0.5 g of 10% Pd/C (Aldrich), hydrogenated at 2 bar until reaction is complete. The catalyst is filtered off, the methanol is removed in a rotary evaporator at a bath temperature of 30° C. and the residue is taken up in dilute sodium bicarbonate solution (pH 8.5). The solution is washed three times with ether. The basic aqueous phase is acidified to pH 2 with 1N HCl and the product is extracted into diethyl ether. The extract is dried over sodium sulphate, filtered and concentrated in a rotary evaporator.

Yield: 2.75 g (70% of theory)
TLC system I: Rf=0.50.
TLC system III: Rf=0.11.
TLC system IV: Rf=0.55.
(Stereoisomers not clearly distinguishable)
HPLC system VII: Rt=3.88 min., 5.06 min., 5.61 min., 7.34 min. (chiral).
MS-DCI: m/e 340 (M+H), m/e 357 (M+NH$_4$).

EXAMPLE 6

4-(N-Phthalyl)amino-2S- or 2R-benzyl-3S- or 3R-hydroxybutyric acid (enantiomer pair of diastereomer A)

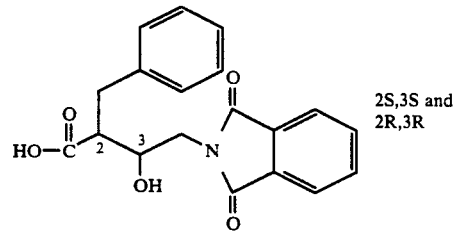

The title compound is prepared analogously to Example 5 by catalytic hydrogenation of 3.9 g (9 mmol) of 4-(N-phthalyl)amino-2S- or 2R-benzyl-3S- or 3R-hydroxy-butyric acid (Example 2, enantiomer pair of diastereomer A).

Yield: 2.6 g (85% of theory).
TLC system III: Rf=0.12.
HPLC system VII: Rt=3.88 min. and 5.06 min. (chiral).
MS-DCI: m/e 340 (M+H) m/e 357 (M+NH$_4$).

EXAMPLE 7 AND EXAMPLE 8

4-(N-phthalyl)amino-2S-benzyl-3S-hydroxybutyric acid 4-(N-phthalyl)amino-2R-benzyl-3R-hydroxybutyric acid

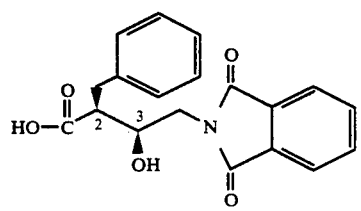

2S,3S: Example 7

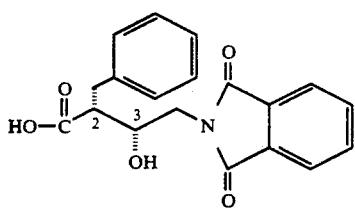

2R,3R: Example 8

The title compounds are obtained by chromatography of the enantiomer pair from Example 6 on a chiral phase (bead polymer from L-menthylacrylamide, EP 218,089, eluent toluene/THF) in optically pure form. The assignment of the configuration is carried out using comparison compounds.

Analytical data

Example 7: $[\alpha]_D = +13.2$ (c=0.7, CHCl$_3$).

Example 8: $[\alpha]_D = -11.0$ (c=0.6, CHCl$_3$).

HPLC system VII: Example 7: Rt=3.88 min. (chiral Example 8: Rt=5.06 min.

All other data (TLC Rf values $^1$H-NMR, MS-DCI) correspond to that already shown in Example 6.

EXAMPLE 9

4-(N-tert.-Butoxycarbonyl-N-benzyl)amino-2R,S-benzyl-3R,S-hydroxybutyric acid

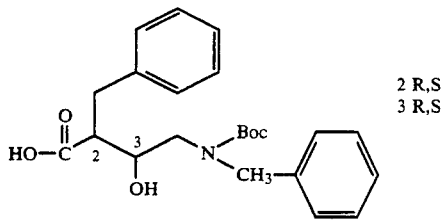

2 R,S
3 R,S 11.1 g (22.7 mmol) of benzyl 4-(N-tert.-butoxycarbonyl-N-benzyl)amino-2-R,S-benzyl-3-R,S-hydroxybutyrate (Example 4) are dissolved in 120 ml of methanol. After adding 1 ml of 1N HCl and 2 g of Pd/C (10%, Aldrich) the mixture is hydrogenated at a hydrogen pressure of 3.5 bar until reaction is complete. The catalyst is filtered off and washed with methanol, the solvent is stripped off in a rotary evaporator (bath temperature 30° C.) and the residue is dried in a high vacuum.

Yield: 7.7 g (85% of theory).

TLC system I: Rf=0.58 (diastereomer A). Rf=0.49 (diastereomer B).

HPLC system III: Rt=6.866 min., retention index 836 (diastereomer A). Rt=6.959 min., retention index 849 (diastereomer B).

HPLC system IV: Rt=12.30 min. 15.50 min. (diastereomer A). Rt=24.13 min. 32.57 min. (diastereomer B).

MS-DCI: m/z 400 (M+H); m/e 344; m/e 300.

EXAMPLE 10 AND EXAMPLE 11

4-(N-tert.-Butoxycarbonyl-N-benzyl)amino-2R- or 2S-benzyl-3R- or 3S-hydroxybutyric acid (diastereomer A)

4-(N-tert.-Butoxycarbonyl-N-benzyl)amino-2R- or 2S-benzyl-3S- or 3R-hydroxybutyric acid (diastereomer B)

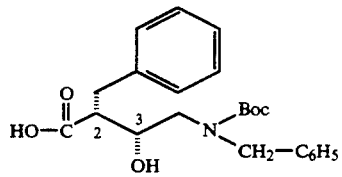

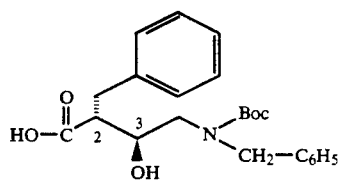

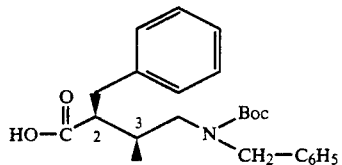

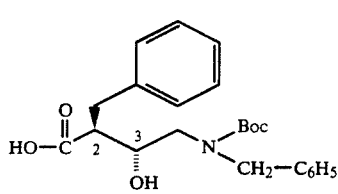

| Example 10 | Example 11 |
|---|---|
| 2R, 3R | 2R, 3S |
| 2S, 3S | 2S, 3R |
| diastereomer A | diastereomer B |

7.6 g of 4-(N-tert.-butoxycarbonyl-N-benzyl)amino-2-R,S-benzyl-3-R,S-hydroxybutyric acid (Example 9) are chromatographed on 500 g of silica gel 60 (Merck, article No. 9385), 0.040-0.063 mm using a step gradient of 1 l of CH$_2$Cl$_2$, 1 l of CH$_2$Cl$_2$/MeOH 99:1, 1 l of CH$_2$Cl$_2$/MeOH 98:2, 1 l of CH$_2$Cl$_2$/MeOH 97:3, 1 l of CH$_2$Cl$_2$/MeOH 96:4 and 3 l of CH$_2$Cl$_2$/MeOH 95:5. The product-containing fractions are combined and concentrated, and the residue is dried in a high vacuum.

Yield: 3.55 g of diastereomer A (Example 10). 1.14 g of mixed fraction of Example 10 and 11. 0.89 g of diastereomer B (Example 11).

The assignment of the absolute configurations is carried out by comparison with the enantiomerically pure compounds of Examples 34 to 37 by HPLC comparison to the chiral system IV.

Analytical data

Diastereomer A (Example 10)

TLC system I: Rf=0.58.

HPLC system III: Rt=6.866 min., retention index 836.
HPLC system IV: Rt=12.30 min. and Rt=15.50 min.
MS-DCI: m/e 400 (M+H); m/e 356; m/e 300.
Diastereomer B (Example 11)
TLC system I: Rf=0.49.
HPLC system III: Rt=6.959 min., retention index 849.
HPLC system IV: Rt=24.13 in. and Rt=32.57 min.
MS-DCI: m/e 400 (M+H); m/e 356; m/e 300.

EXAMPLE 12

(4R)-3-[4-(N-tert.-Butoxycarbonyl-N-benzyl)amino-(2S)-2-cyclohexylmethyl-(3R,S)-3-hydroxybutyryl]-4-benzyloxazolidin-2-one

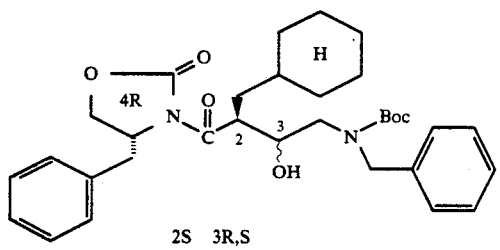

The title compound is obtained pure by chromatography analogously to Example 22 starting from the compound of Example XV and the aldehyde of Example IV.

TLC system IX: Rf=0.82 (4R,2S,3R-isomer). Rf=0.78 (4R,2S,3A-isomer).
HPLC system II: Rt=91.73 min. (4R,2S,3S-isomer). Rt=117.52 min. (4R,2S,3R-isomer).
(+)FAB-MS: m/e 565 (M+H); m/e 587 (M+Na).

EXAMPLE 13

4-(N-tert.-Butoxycarbonyl-N-benzyl)amino-(2S)-2-cyclohexylmethyl-(3R,S)-3-hydroxybutyric acid

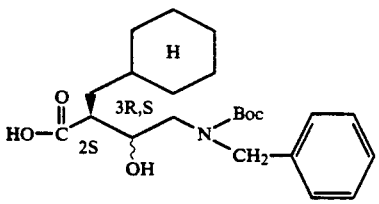

The title compound is obtained from the compound of Example 12 by removal of the chiral auxiliary reagent and subsequent chromatography (as described in Example 34).

TLC system II: Rf=0.42; 2S,3S-isomer. 0.38; 2S,3R-isomer.
HPLC system III: Rt=7.605 min. (ret. index 956), 2S,3S-isomer. Rt=7.754 min. (ret. index 979) 2S,3R-isomer.
(+)FAB-MS: m/e 444 (M+K), m/e 482 (M+2K-H); m/e 520 (M+3K-2H).

EXAMPLE 14

(4R)-3-[4-(N-tert.-Butoxycarbonyl-N-benzyl)amino-(2S)-2-benzyl-(3R,S)-3-hydroxybutyryl)-4-(2-propyl-)oxazolidin-2-one

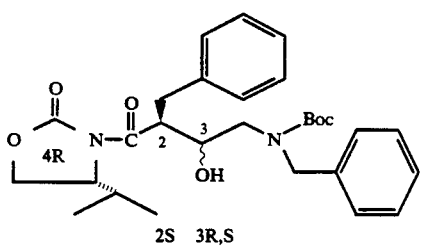

3.32 ml (23.6 mmol) of diisopropylamine are dissolved in 40 ml of absolute THF under nitrogen and cooled to −20° C., and 16.1 ml (25.8 mmol) of a 1.6N solution of n-butyllithium (n-hexane) are added with stirring. The mixture is subsequently stirred for 10 minutes and cooled to −70° C. A solution of 5.61 g (21.5 mmol) of (4R)-3-(3-phenylpropionyl)-4-(2-propyl)oxazolidin-2-one (Example VII) in 60 ml of dry HF is added at this temperature and the mixture is subsequently stirred for 30 minutes. A solution of 5.9 g (23.65 mmol) of N-tert.-butoxycarbonyl-N-benzyl-glycinal (Example IV) is added dropwise to the mixture at −70° C. and it is subsequently stirred for 2 hours.

The mixture is hydrolyzed using 250 ml of saturated NH4Cl solution and brought to room temperature, and 300 ml of diethyl ether are added. The organic phase is separated off and the aqueous phase is extracted once with 300 ml of diethyl ether. The combined ether phases are washed with saturated NaCl solution, dried over sodium sulphate and concentrated.

The crude yield (11.75 g) is chromatographed on 580 g of silica gel 60 (Merck, article No. 9385) 40–63 μm (230–400 mesh) using a gradient of 1 l each of petroleum ether/ethyl acetate of 95:5 to 84:16 (12 increasing steps in 1% stages) and finally 6 l of petroleum ether/ethyl acetate 83:17.

The product-containing fractions are collected, the stereoisomers being detected and appropriately purified by means of HPLC. The 4R, 2R, 3R-isomer is also obtained as a secondary component. The 4R, 2S, 3R-isomer elutes first, then the 4R, 2R, 3R-isomer (secondary component) and finally the 4R, 2S, 3S-isomer (conversely to the elution sequence in the reversed phase HPLC systems II and V).

Total yield: 5.88 g (53% of theory).
Analytical data of the crude mixture
TLC system XI: Rf=0.36.
HPLC system II:
Rt=22.80 min. 4R, 2S, 3S isomer.
Rt=26.87 min. 4R, 2S, 3S isomer (secondary component).
Rt=27.01 min. 4R, 2S, 3S isomer.
HPLC system V:
Rt=12.07 min. 4R, 2S, 3S isomer.
Rt=13.65 min. 4R, 2R, 3R isomer (secondary component).
Rt=14.07 min. 4R, 2S, 3S isomer.

The assignment of the configurations is carried out using the corresponding pure substances. For this, 1H-NMR or HPLC data comparisons with the model compounds of Examples XI–XIV are carried out for the two principal products. The essential criteria
1. the relative differences in the $^1$H absorption levels (in DMSO)
    a) of the hydroxyl protons,
    b) of the H$_4$ oxazolidinone protons and
2. the elution sequences on the reversed phase HPLC systems II and V.

The assignment of configuration of the secondary component is carried out by conversion into the free acid (removal of the optical auxiliary reagent) and HPLC comparison (chiral system IV) with the principal products of the corresponding S-series (see under Example 48).

EXAMPLES 15, 16 AND 17

(4R)-3-[4-(N-tert.-Butoxycarbonyl-N-benzyl)amino-(2S)-2-benzyl-(3R)-3-hydroxy-butyryl]-4-(2-propyl)oxazolidin-2-one (Example 15)

(15)

(4R)-3-[4-(N-tert.-Butoxycarbonyl-N-benzyl)amino-(2R)-2-benzyl-(3R)-3-hydroxy-butyryl]-4-(2-propyl)oxazolidin-2-one (Example 16)

(16)

secondary component (4R)-3-[4-(N-tert.-Butoxycarbonyl-N-benzyl)amino-(2S)-2-benzyl-(3S)-3-hydroxy-butyryl]-4-(2-propyl)oxazolidin-2-one (Example 17)

(17)

The title compounds are obtained pure by silica gel chromatography of Example 14. Mixed fractions can optionally be rechromatographed.

Analytical data of Example 15 (4R, 2S, 3R-isomer)
HPLC system II: Rt=27.01 min.
HPLC system III: Rt=8.381 min., retention index 1070.
HPCL system V: Rt=14.07 min.
[α]$_D$= −90.75 (c=1, methanol).
(+)FAB-MS=m/e  511  (M+H);  m/e=533 (M+Na).

Analytical data of Example 16 (4R, 2R, 3R-isomer)
HPLC system II: Rt=26.87 min.
HPLC system V: Rt=13.65 min.
[α]$_D$= −41.20 (c=1, methanol),
(+)FAB-MS=m/e  511  (M+H);  m/e=533 (M+Na).

Analytical data of Example 17 (4R, 2S, 3S-isomer)
HPLC system II: Rt=22.80 min.
HPLC system III: Rt=8.299 min., retention index 1045.
HPLC system V: Rt=12.07 min.
[α]$_D$= −58.88 (c=1, methanol).
(+)FAB-MS=m/e  511  (M+H);  m/e=533 (M+Na).

Single crystals of Example 17 were obtained from ether/n-hexane and subjected to an X-ray structural analysis. By means of this, the structure assignment described under Example 14 was confirmed. The 4R, 2S, 3S-configuration shown belongs to Example 17.

EXAMPLE 18

(4S)-3-[4-(N-tert.-Butoxycarbonyl-N-benzyl)amino-(2R)-2-benzyl-(3R,S)-3-hydroxy-butyryl]-4-(2-propyl)oxazolidin-2-one The title compound is obtained analogously to Example 14 by reacting the lithium anion of 21.2 g (81 mmol) of (4S)-3-(3-phenyl-propionyl)-4-(2-propyl)oxazolidin-2-one (J.J. Plattner et al., J. Med. Chem. 1988, 31 (12), 2277–2288) with 22.2 g (89 mmol) of the aldehyde from Example IV. The 4S, 2S, 3S-isomer is formed as a by-product (analogously to Example 14); the assignment is carried out as already described there.

TLC system IX: Rf=0.76. Rf=0.16
HPLC system II:
  Rt=22.80 in. 4S, 2R, 3R isomer.
  Rt=26.86 min. 4S, 2S, 3S isomer (by-product).
  Rt=27.00 min. 4S, 2R, 3S isomer.
(+)FAB-MS: m/e 511 (m+H); m/e 533 (M+Na).
Total yield: 25.68 g (62.1% of theory). (Examples 19, 20 and 21 after separation into the isomers).

EXAMPLES 19, 20 AND 21

(4S)-3-[4-(N-tert.-butoxycarbonyl-N-benzyl)amino-(2R)-2-benzyl-(3S)-3-hydroxy-butyryl]-4-(2-propyl)oxazolidin-2-one (Example 19)

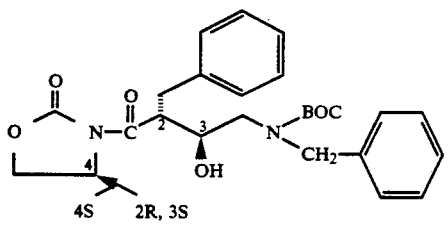

(4S)-3-[4-(N-tert.-butoxycarbonyl-N-benzyl)amino-(2S)-2-benzyl-(3S)-3-hydroxy-butyryl]-4-(2-propyl)oxazolidin-2-one (Example 20)

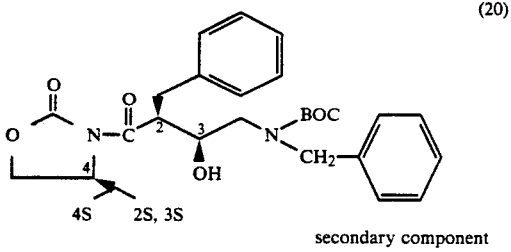

secondary component (4S)-3-[4-(N-tert.-butoxycarbonyl-N-benzyl)amino-(2R)-2-benzyl-(3R)-3-hydroxy-butyryl]-4-(2-propyl)oxazolidin-2-one (Example 21)

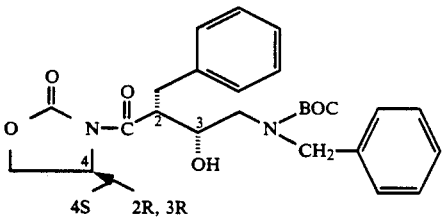

The title compounds are obtained pure by isomer separation of the mixture from Example 18 (analogously to Examples 15, 16 and 17).

Analytical data for Example 19 (4S, 2R, 3S-isomer)
HPLC system VI: Rt=12.53 min.
$[\alpha]_D = +89.42$ (c=1, methanol).
(+)FAB-MS=m/e 511 (M+H); m/e=533 (M+Na).

Analytical data for Example 20 (4S, 2S, 3S-isomer)
HPLC system VI: Rt=12.01 min. $[\alpha]_D = +41.67$ (c=1, methanol).

Analytical data for Example 21 (4S, 2R, 3R-isomer)
HPLC system VI: Rt=11.21 min.
$[\alpha]_D = +58.87$ (c=1, methanol).

All other data (HPLC systems II, IIIm, V, $^1$H-NMR in dimethyl sulphoxide, ((+)FAB-MS) corresponds to that of the mirror image isomeric compounds from Examples 15, 16 and 17.

EXAMPLE 22

(4R)-3-[4-(N-tert.-butoxycarbonyl-N-benzyl)amino-(2S)-2-benzyl-(3R,S)-3-hydroxy-butyryl]-4-benzyl-oxazolidin-2-one

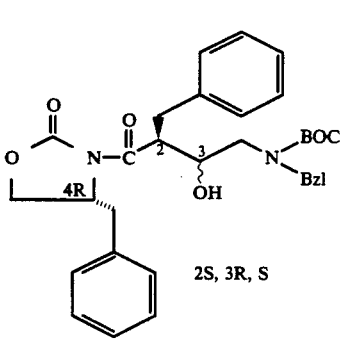

The title compound is obtained in analogy to the procedure of Example 14 by reacting the compound from Example X and the compound from Example IV. The 4R, 2R, 3R-isomer again occurs as a by-product.

TLC system IX:
Rf=0.90 4R, 2S, 3R-isomer.
Rf=0.82 4R, 2S, 3S-isomer.
Rf=0.66 4R, 2R, 3R-isomer (by-product).

HPLC system II:
Rt=33.56 min. 4R, 2S, 3S-isomer.
RT=37.48 min. 4R, 2R, 3R-isomer (by-product).
Rt=43.29 min. 4R, 2S, 3R-isomer.

(+)FAB-MS: m/e 529 (M+H); m/e/ 581 (M+Na).

EXAMPLES 23, 24 AND 25

(4R)-3-[4-(N-tert.-butoxycarbonyl-N-benzyl)amino-(2S)-2-benzyl-(3R)-3-hydroxy-butyryl]-4-benzyl-oxazolidin-2one (Example 23)

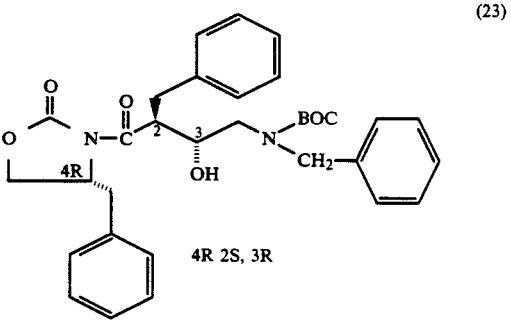

(4R)-3-[4-(N-tert.-butoxycarbonyl-N-benzyl)amino-(2R)-2-benzyl-(3R)-3-hydroxy-butyryl]4-benzyl-oxazolidin-2-one (Example 24)

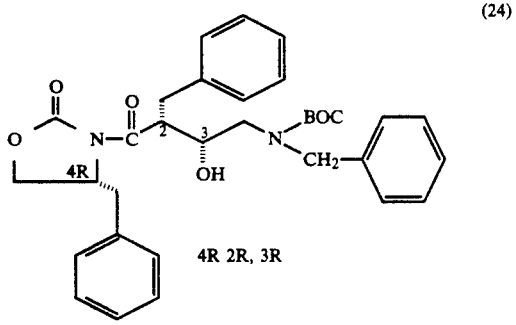

(24)

4R 2R, 3R

(4R)-3-[4-(N-tert.-butoxycarbonyl-N-benzyl)amino-(2S)-2-benzyl-(3S)-3-hydroxy-butyryl]-4-benzyl-oxazolidin-2-one (Example 25)

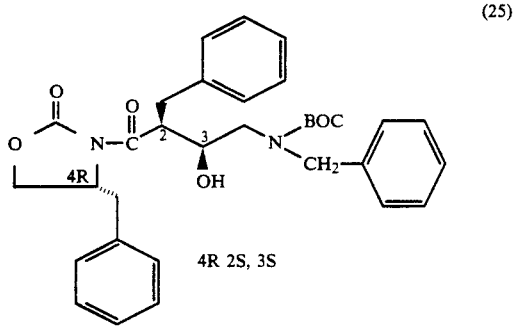

(25)

4R 2S, 3S

The title compounds are obtained pure by isomer separation of the mixture from Example 22 (analogously to Examples 15, 16 and 17 ).

Analytical data (Examples 23, 24 and 25)

The TLC and HPLC values have already been shown under Example 22.

Example 23: $[\alpha]_D = -110.84$ (c=1, methanol).
Example 25: $[\alpha]_D = -53.26$ (c=1, methanol),

EXAMPLE 26

(4R,5S)-3-[4-(N-tert.-butoxycarbonyl-N-benzyl)amino-(2S)-2-benzyl-(3R,S)-3-hydroxy-butyryl]-4-methyl-5-phenyloxazolidin-2one

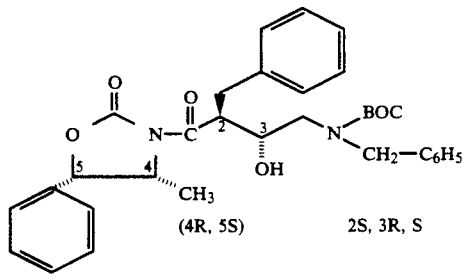

(4R, 5S)    2S, 3R, S

The title compound is obtained analogously to Example 14, starting form (4R,5S)-3-(3-phenylpropionyl)-4-methyl-5-phenyl oxazolidin-2-one (Example VIII) and the aldehyde from Example IV. the (4R,5S), 2R,3R-isomer again occurs as a by-product.

TLC system IX: Rf=0.83.
TLC system XV: Rf=0.20.
HPLC system II:
Rt=46.94 min. (4R,5S), 2S,3S-isomer.
Rt=49.85 min. (4R,2S), 2R,3R-isomer (by-product).
Rt=56.74 min. (4R,5S), 2S,3R-isomer. (+)FAB-MS: m/e 559 (M+H); m/e 581 (M+Na).

EXAMPLES 27, 28 and 29

(4R,5S)-3-[4-(N-tert.-butoxycarbonyl-N-benzyl)amino-(2S)-2-benzyl-(3R)-3-hydroxy-butyryl]-4-methyl-5-phenyloxazolidin-2-one (Example 27)

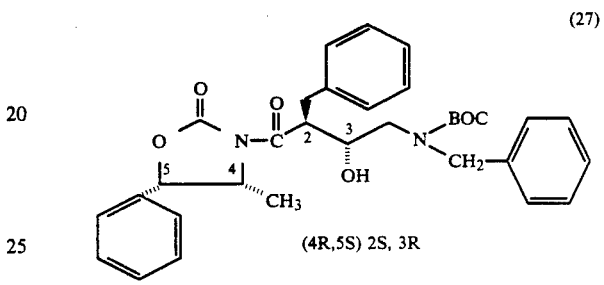

(27)

(4R,5S) 2S, 3R (4R,5S)-3-[4-(N-tert.-butoxycarbonyl-N-benzyl)amino-(2R)-2-benzyl-(3R)-3-hydroxy-butyryl]-4-methyl-5-phenyloxazolidin-2-one (Example 28)

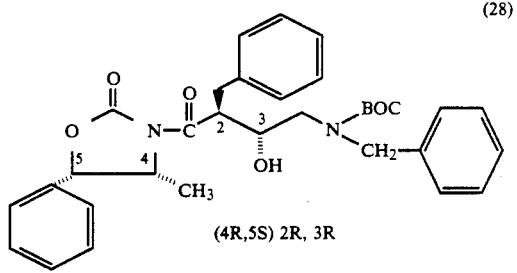

(28)

(4R,5S) 2R, 3R (4R,5S)-3-[4-(N-tert.-butoxycarbonyl-N-benzyl)amino-(2S)-2-benzyl-(3S)-3-hydroxy-butyryl]-4-methyl-5-phenyloxazolidin-2-one (Example 28)

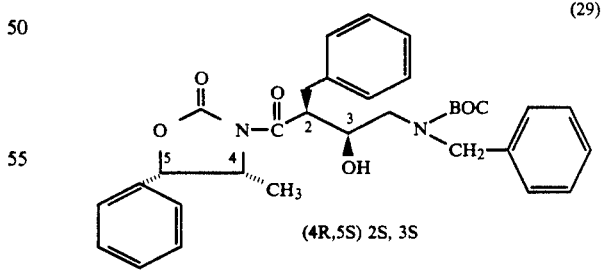

(29)

(4R,5S) 2S, 3S

The title compounds are obtained pure by isomer separation of the mixture from Example 26 (analogously to Examples 15, 16 and 17.

Analytical data for Example 27
(4R, 5S, 2S, 3R-isomer)
HPLC system V: Rt=25.59 min.
(+)FAB-MS: m/e/ 559 (M+H); m/e 581 (M+Na).
$[\alpha]_D = -50.60$ (c=1, methanol).

Analytical data for Example 28
(4R, 5S, 2R, 3R-isomer)
HPLC system V: Rt=23. 11 min.
(+)FAB-MS: m/e 559 (M+H); m/e/ 581 (M+Na).
Analytical data for Example 29
(4R, 5S, 2S, 3S-isomer).
HPLC system V: Rt=22.02 min.
(+)FAB-MS: m/e 559 (+H); m/e 581 (M+Na).

EXAMPLE 30

(4S)-3-[4-(N-tert.-butoxycarbonyl-N-benzyl)amino-(2R)-2-benzyl-(3R,S)-3-hydroxy-butyryl]-4-phenyl-oxazolidin-2-one

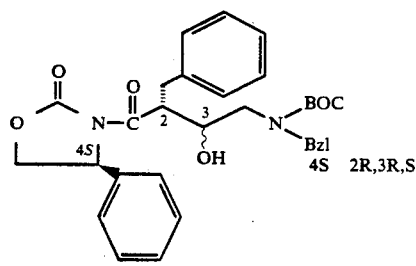

4S  2R,3R,S

The title compound is obtained analogously to Example 14, starting from (4S)-3-(3-phenylpropionyl)-4-phenyloxazolidin-2-one (Example IX) and the aldehyde from Example IV. The 4S, 2S, 3S-isomer occurs as a by-product. TLC system IX: Rf=0.77.

TLC system XV: Rf=0.21.
HPLC system II:
Rt=25.59 min. 4S, 2R, 3R-isomer.
Rt=27.74 min. 4S, 2S, 3S-isomer.
Rt=31.61 min. 4S, 2R, 3S-isomer.
(+)FAB-MS: m/e 545 (M+H); m/e 567 (M+Na).

EXAMPLES 31, 32 AND 33

(4S)-3-[4-(N-tert.-butoxycarbonyl-N-benzyl)amino-(2R)-2-benzyl-(3S)-3-hydroxy-butyryl]-4-phenyl-oxazolidin-2-one (Example 31)

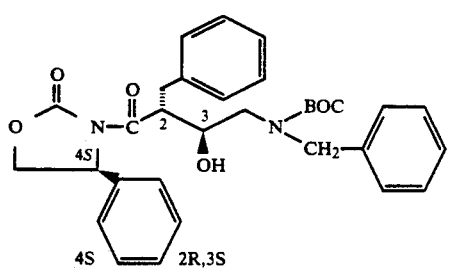

(31)

4S  2R,3S (4S)-3-[4-(N-tert.-butoxycarbonyl-N-benzyl)amino-(2S)-2-benzyl-(3S)-3-hydroxy-butyryl]-4-phenyl-oxazolidin-2-one (Example 32)

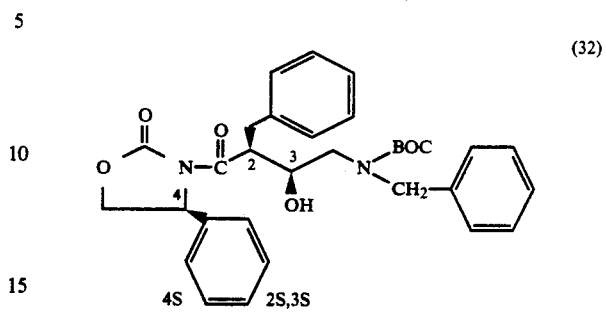

(32)

4S  2S,3S (4S)-3-[4-(N-tert.-butoxycarbonyl-N-benzyl)amino-(2R)-2-benzyl-(3R)-3-hydroxy-butyryl]-4-phenyl-oxazolidin-2-one (Example 33)

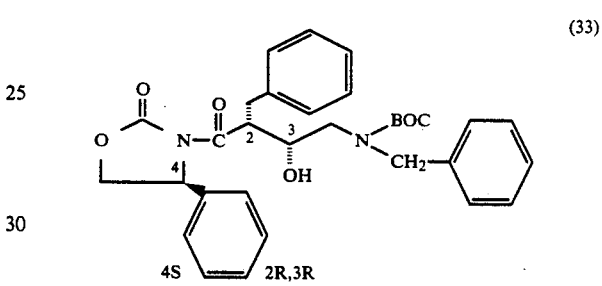

(33)

4S  2R,3R

The title compounds were obtained pure by isomer separation of the mixture from Example 30 (analogously to Examples 15, 16 and 17).
Analytical data for Example 31
(4S, 2R, 3S-isomer).
HPLC system II: Rt=25.73 1 min.
(+)FAB-MS: m/e 545 (M+H).
Analytical data for Example 32
(4S, 2S, 3S-isomer).
HPLC system II: Rt=28.74 min.
(+)FAB-MS: m/e 545 (M+H).
Analytical data for Example 33
(4S, 2R, 3R-isomer).
HPLC system II: Rt=31.61 min.
(+)FAB-MS: m/e 545 (M+H).

EXAMPLE 34

4-(N-tert.-Butoxycarbonyl-N-benzyl)amino-(2S)-2-benzyl-(3R)-3-hydroxybutyric acid

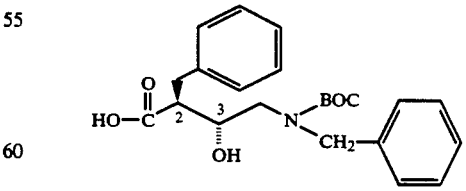

11.8 g (21.1 mol) of (4R,5S)-3-[4-(N-tert.-butoxycarbonyl-N-benzyl)amino-(2)-2-benzyl-(3R)-3-hydroxybutyryl]-4-methyl-5-phenyloxazolidin-2-one (Example 27) are dissolved in 840 ml of THF/H$_2$O 3:1. 28.4 ml (278.5 mmol) of H$_2$O$_2$ (30% strength, Aldrich) and 2.03 g (84.4 mmol) of lithium hydroxide are then added and the mixture is stirred overnight at 3° C. 84 ml of 1 N HCl is added to the mixture and the THF is stripped off in a rotary evaporator. The aqueous phase is adjusted to pH 3 and extracted twice with ethyl acetate. The combined organic phases are dried over sodium sulphate, filtered and concentrated in a rotary evaporator. The crude product is chromatographed on 600 g of silica gel 60 (Merck, article No. 9385) 40–63 μm (230–400 mesh) using a step gradient (as described in Examples 14 and 15). The product-containing fractions are combined and concentrated. The product is cyrstallized from ether/n-hexane, filtered off with suction and dried.

The title compound can also be obtained analogously, enantiomerically pure, by removal of the chiral auxiliary reagent from the following examples: Examples 15 and 23.

Yield: 3.68 g (43.7% theory).
TLC system I: Rf=0.49.
HPLC system IV: Rt=32.57 min.
(+)FAB-MS: m/e 438 (M+K); m/e 476 (M+2K−H).
[α]$_D$:−21.75 (c=1, MeOH).

EXAMPLE 35

4-(N-tert.-Butoxycarbonyl-N-benzyl)amino-(2R)-2-benzyl-(3S)-3-hydroxybutyric acid

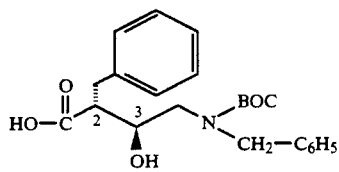

By removal of the chiral auxiliary reagent and subsequent chromatography (as described in Example 34), the title compound is obtained enantiomerically pure from the following examples Examples 19 and 31.

Analytical data
TLC system I: Rf=0.49.
HPLC system IV: Rt=24.13 min.
(+)FAB-MS: m/e 438 (M+K); m/e 476 (M+2K−H).
[α]$_D$:+20.36 (c−1, MeOH).
$^1$H-NMR (250 MHz, DMSO) identical with the data from Example 34.

EXAMPLE 36

4-(N-tert.-Butoxycarbonyl-N-benzyl)amino-(2R)-2-benzyl-(3R)-3hydroxybutyric acid

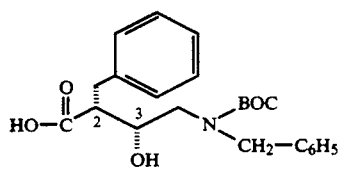

By removal of the auxiliary reagent and subsequent chromatography (as described in Example 34), the title compound is obtained enantiomerically pure from the following examples: Examples 16, 21, 24, 28 and 33.

Analytical data
TLC system I: Rf=0.58.
HPLC system IV: Rt=15.10 min.
(+)FAB-MS: m/e 438 (M+K); m/e 476 (M+2K−H).
[α]$_D$:−17.58 (c=1, MeOH).

EXAMPLE 37

4-(N-tert.-Butoxycarbonyl-N-benzyl)amino-(2S)-2-benzyl-(3S)-3-hydroxybutyric acid

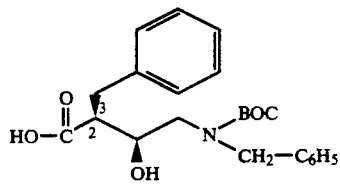

By removal of the chiral auxiliary reagent and subsequent chromatography (as described in Example 34), the title compound is obtained enantiomerically pure from the following examples: Examples 17, 20, 25, 29 and 32.

Analytical data
TLC system I: Rf=0.58.
HPLC system IV: Rt=12.30 min.
(+)FAB-MS: m/e 438 (M+K); m/e 476 (M+2K−H).
[α]$_D$:+17.96 (c=1, MeOH).
$^1$H-NMR (250 MHz, DMSO) identical with Example 36.

EXAMPLE 38

4-Amino-(2R,S)-benzyl-(3R,S)-hydroxybutyric acid

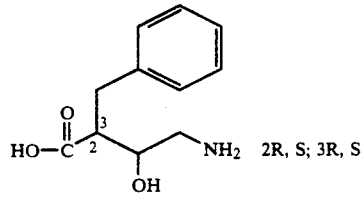

5.11 g (15 mmol) of 4-(N-phthalyl)amino-2-R,S-benzyl-3R,S-hydroxybutyric acid (Example 5) are dissolved in 10 ml of MeOH/H$_2$O 1:1 and 913.86 μl (18.8 mmol) of hydrazine hydrate (Bayer, LLB Lev C 703, 01-825) are added. The mixture is kept at 5° C. for 3 days and hydrazine hydrate (182 μl, 3.75 mmol) is added again. After one day at +5° C., the mixture is rendered neutral with 1 N HCl and cautiously concentrated in a rotary evaporator to semi-dryness.

The residue is taken up in 1 N NaOH (to pH 10), extracted three times with ether and then three times with ethyl acetate. The aqueous phase is adjusted to pH 2 with 1 N HCl and the residue is filtered off. The residue is stirred in 0.1 N HCl and filtered off with suction. The combined aqueous-acidic filtrates are concentrated to a half of their volume, frozen and lyophilized. The crude product is desalted by means of adsorption by Mitsubishi Diaion HP-20, washing with water and elution with a gradient of MeOH/H$_2$O 10:90–50:50. The product-containing filtrates are combined, MeOH is evaporated off in a rotary evaporator, an the residue is frozen and lyophilized.

Yield: 2.2 g (70.1% of theory).
TLC system IV: Rf=0.52.
TLC system V: Rf=0.73.

EXAMPLE 39

4-N-tert.-Butoxycarbonyl)-amino-(2R,S)-benzyl-(3R,S)-hydroxybutyric acid

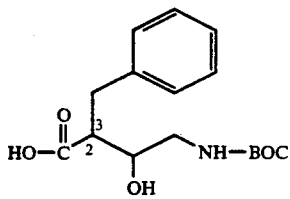

2.1 g (10 mmol) of 4-amino-2-R,S-benzyl-3R,S-hydroxybutyric acid (Example 38) are dissolved in 40 ml of dioxane and 20 ml of 1 N NaOH. 3.3 g (15 mmol) of di-tert.-butyl dicarbonate (Fluka) are added to the mixture with ice cooling and it is stirred overnight.

The mixture is rendered neutral by adding 1 N HCl and the dioxane is stripped off in a rotary evaporator. The aqueous phase is adjusted to pH 9 and washed three times with ether. The mixture is then adjusted to pH 3 with 1 N HCl and the product is extracted in ethyl acetate. The combined ethyl acetate phases are washed with saturated NaCl solution, dried over sodium sulphate, filtered and concentrated.

Yield: 2.6 g (84% of theory).
TLC system I: Rf=0.45.
(+)FAB-MS: m/e 310 (M+H), m/e (M+Na).

EXAMPLE 40

4-(N-Benzyl)amino-(2R) or (2S)-benzyl-(3S) or (3R)-3-hydroxybutyric acid hydrochloride

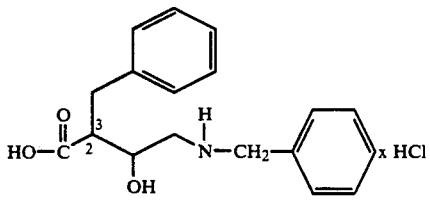

2R, 3S and 2S, 3R

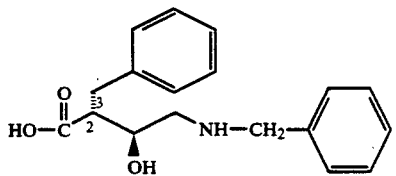

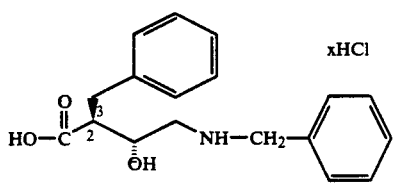

400 mg (1mmol) of the diastereomers B from Example 11 are stirred at room temperature for 1 hour in 10 ml of 4N HCl in dioxane to remove the N-tert.-butoxycarbonyl protecting group. The mixture is concentrated to dryness and coevaporated with ether several times. The residue is dried over KOH.

Yield: 320 mg (96% of theory).
TLC system III: Rf=0.04.
TLC system V: Rf=0.51.
TLC system XVI: Rf=0.82.
(+)FAB-MS: m/e 300 (M+H), m/e 322 (M+Na).

EXAMPLE 41

4-Amino-(2R)- or (2S)-benzyl-(3S) or (3R)-3-hydroxybutyric acid

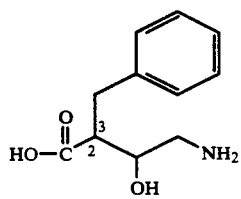

2R, 3S and 2S, 3R 280 mg (0.93 mmol) of the N-benzyl compound from Example 40, which has been converted into the free base by neutralizing with aqueous ammonia and lyophilizing several times, are catalytically N-debenzylated by boiling for 75 minutes in 15 ml of methanol, 1.1 g (18.6 mmol) of ammonium formate and 300 mg of 10% strength Pd/C. The catalyst is filtered off from the mixture, and the solution is taken up in water and freeze-dried several times.

Yield: 49 mg (25% of theory).
TLC system XVI: Rf=0.67.
(+)FAB-MS: m/e 210 (M+H), m/e 232 (M+Na).

EXAMPLE 42

4-(N-tart.-Butoxycarbonyl)-amino-(2R) or (2S)-benzyl-(3S)- or (3R)-3-hydroxybutyric acid

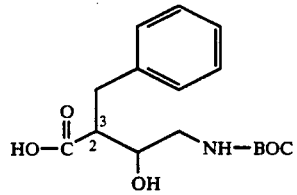

2R, 3S and 2S, 3R

The title compound is obtained as described in Example 39 by reacting 44 mg (0.22 mmol) of Example 41 with 96 mg of di-tert.-butyl dicarbonate . The crude product is chromatographed on silica gel using the eluent system CH₂Cl₂/MeOH 95:5.

Yield: 11.1 mg (17% of theory).
TLC system IV: Rf=0.49.
MS-DCI: m/e 310 (M+H).

EXAMPLE 43

4-(N-Isopropyl)amino-(2R) or (2S)-2-benzyl-(3S) or (3R)-3-hydroxybutyric acid

2R, 3S and 2S, 3R 400 mg (2 mmol) of the diastereomer B from Example 11 are stirred with 4 N HCl in dioxane as described in Example 40 to remove the BOC protecting group. The mixture is concentrated, diluted with 150 ml of water, adjusted to pH 8 with 25% strength ammonia and freeze-dried. The voluminous amorphous residue of the intermediate N-benzyl compound (Example 41) is co-evaporated with acetone and dried with an oil pump. The mixture is dissolved in 30 ml of methanol and, after adding 400 mg of 20% Pd(OH)$_2$ as a catalyst, hydrogenated at 3.5 bar. The catalyst is filtered off and the organic solvent is removed in a rotary evaporator. The residue is dissolved in 1 ml of acetonitrile. After adding 50 ml of H$_2$O, the mixture is frozen and freeze-dried.

Yield: 220 mg (87% of theory).
TLC system XVI: Rf=0.67.

EXAMPLE 44

4-(N-tert.-Butoxycarbonyl-N-iospropyl)amino-(2R) or (2S)-2-benzyl-(3S) or (3R)-3-hydroxybutyric acid

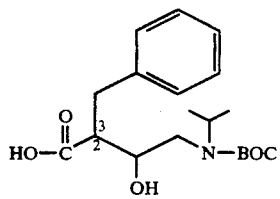

2R, 3S and 2S, 3R 220 mg (0.87 mmol) of the compound from Example 43 are reacted with 480 mg (2.2 mmol) of di-tert.-butyl dicarbonate as described in Example 39 and worked up analogously. The acidic organic phase is dried over sodium sulphate, the sodium sulphate is filtered off and the solution is concentrated to dryness.

Yield: 131.3 mg (50.5% of theory).
TLC system IV: Rf=0.49.
MS-DCI: m/e 352 (M+H).

EXAMPLE 45

4-(N-tert.-Butoxycarbonyl)amino-2R,S-cyclohexyl-methyl-3R,S-hydroxybutyric acid

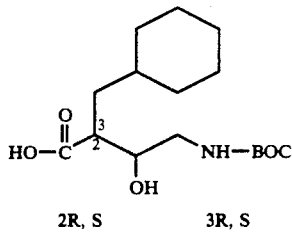

2R, S     3R, S 770 mg (2.5 mmol) of 4-(N-tert.-butoxycarbonyl-)amino-2R,S-benzyl-3R,S-hydroxybutyric acid (Example 39) are dissolved in 20 ml of MeOH. After adding 0.5 ml of glacial acetic acid and 1 g of 5 percent strength Rh/C*, the mixture is hydrogenated at room temperature and at a hydrogen pressure of 100 bar for 5 hours. The catalyst is filtered off and the filtrate is concentrated to dryness. 10 ml of water are added to the oily residue and the product is extracted from the acidic aqueous phase with 3×10 ml of ethyl acetate. The combined organic phase is dried over sodium sulphate, filtered and concentrated. The residue is taken up in acetonitrile/H$_2$O and freeze-dried.

* =Rhodium on carbon-catalyst

Yield: 600 mg (76% of theory).
TLC system IV: Rf=0.60.
(+)FAB-MS: m/e 338 (M+Na).

The examples shown in the following tables are characterized by $^1$H-NMR values and by mass spectroscopy.

EXAMPLES 46 TO 49

The compounds shown in Table 1 were prepared from the corresponding enantiomeric precursors of Examples 34-37 by removal of the BOC protecting group in analogy to Example 40.

TABLE 1

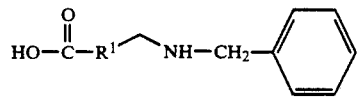

| Example No. | R$^1$ | Configuration | [α]$_D$ (c = 1 MeOH) Crude product |
|---|---|---|---|
| 46 | 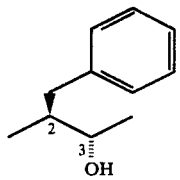 | 2S, 3R | −13.88 |
| 47 | 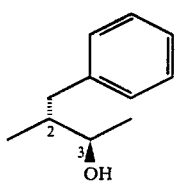 | 2R, 3S | +9.97 |

TABLE 1-continued

HO—C(=O)—R¹—NH—CH₂—C₆H₅

| Example No. | R¹ | Configuration | [α]_D (c = 1 MeOH) Crude product |
|---|---|---|---|
| 48 | (2,3-substituted; CH₃ at 2, OH at 3, benzyl) phenyl-CH₂–CH(CH₃)–CH(OH)–CH₃ | 2R, 3R | +13.95 |
| 49 | phenyl-CH₂–CH(CH₃)–CH(OH)–CH₃ | 2S, 3S | −12.75 |

EXAMPLES 50 TO 53

The compounds shown in Table 2 were prepared from the corresponding enantiomeric precursors of Examples 46–49 by removal of the N-benzyl protecting group in analogy to Example 41.

TABLE 2

HO—C(=O)—R¹—NH₂

| Example No. | R¹ | Configuration | [α]_D (c = 1) (Crude product) |
|---|---|---|---|
| 50 | phenyl-CH₂–CH(CH₃)–CH(OH)–CH₃ | 2S, 3R | −19.92 (MeOH) |
| 51 | phenyl-CH₂–CH(CH₃)–CH(OH)–CH₃ | 2R, 3S | +15.05 |
| 52 | phenyl-CH₂–CH(CH₃)–CH(OH)–CH₃ | 2R, 3R | +36.06 |

TABLE 2-continued

HO—C(=O)—R¹—NH₂

| Example No. | R¹ | Configuration | [α]_D (c = 1) (Crude product) |
|---|---|---|---|
| 53 | phenyl-CH₂–CH(CH₃)–CH(OH)–CH₃ | 2S, 3S | −37.41 |

EXAMPLES 54 TO 57

The compounds shown in Table 3 were prepared from the corresponding enantiomeric precursors of Examples 50–53 by reaction with di-tert.-butyl dicarbonate in analogy to Example 39.

TABLE 3

HO—C(=O)—R¹—NH—BOC

| Example No. | R¹ | Configuration | [α]_D (c = 1) (Crude product) |
|---|---|---|---|
| 54 | phenyl-CH₂–CH(CH₃)–CH(OH)–CH₃ | 2S, 3R | −7.47 |
| 55 | phenyl-CH₂–CH(CH₃)–CH(OH)–CH₃ | 2R, 3S | +14.26 |
| 56 | phenyl-CH₂–CH(CH₃)–CH(OH)–CH₃ | 2R, 3R | +10.75 |
| 57 | phenyl-CH₂–CH(CH₃)–CH(OH)–CH₃ | 2S, 3S | −11.62 |

EXAMPLES 58 TO 61

The compounds shown in Table 4 were prepared from the corresponding enantiomeric precursors of Examples 54–57 by catalytic high pressure hydrogenation in analogy to Example 45 or by reacting the corresponding enantiomeric precursors of Examples 62 to 65 with di-tert.-butyl dicarbonate in analogy to Examples 54–57.

TABLE 4

HO—C(=O)—R¹⌒NH—BOC

| Example No. | R¹ | Configuration |
|---|---|---|
| 58 | cyclohexyl-CH2-CH(3)-CH(2)(OH)- | 2S, 3R |
| 59 | cyclohexyl-CH2-CH(3)-CH(2)(OH)- | 2R, 3S |
| 60 | cyclohexyl-CH2-CH(3)-CH(2)(OH)- | 2R, 3R |
| 61 | cyclohexyl-CH2-CH(3)-CH(2)(OH)- | 2S, 3S |

EXAMPLES 62 TO 65

The compounds shown in Table 5 were prepared from the corresponding enantiomerically pure precursors of Examples 50–53 by catalytic high pressure hydrogenation in analogy to Example 45.

TABLE 4

HO—CO—R¹⌒NH2

| Example No. | R¹ | Configuration |
|---|---|---|
| 62 | cyclohexyl-CH2-CH(3)-CH(2)(OH)- | 2S, 3R |
| 63 | cyclohexyl-CH2-CH(3)-CH(2)(OH)- | 2R, 3S |
| 64 | cyclohexyl-CH2-CH(3)-CH(2)(OH)- | 2R, 3R |
| 65 | cyclohexyl-CH2-CH(3)-CH(2)(OH)- | 2S, 3S |

EXAMPLE 66

N-α-tert.-Butoxycarbonyl-N-im-tert.-butoxycarbonyl-D-histidyl-D-phenylalanine benzyl ester

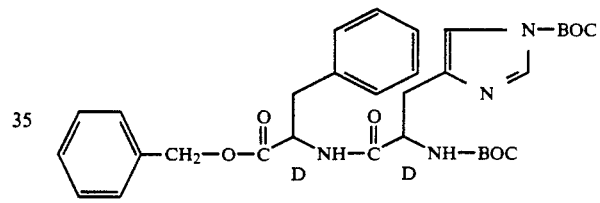

25 g (0.054 mol) of D-phenylalanine benzyl ester tosylate (Senn Chemicals) and 23.3 g (0.065 g) of N-α-tert.-butoxycarbonyl-N-im-tert.-butoxycarbonyl-D-histidine (Bissendorf Biochemicals) are dissolved in 200 ml of $CH_2Cl_2$ and 100 ml of DMF. 11.1 g (0.081 mol) of N-ethylmorpholine and then 14.6 g (0.070 mol) of dicyclohexylcarbodiimide are added to the mixture with stirring.

The mixture is stirred overnight at room temperature and concentrated in a rotary evaporator under a high vacuum, and the residue is taken up in 100 ml of ethyl acetate. The mixture is briefly stirred and kept in the refrigerator at 5° C. for 2 hours. The precipitated dicyclohexylurea is filtered off with suction and the filtrate is shaken with saturated sodium bicarbonate solution, hydrochloric acid pH 3 and saturated sodium chloride solution, dried over sodium sulphate and concentrated to dryness. The crude mixture (45.5 g) is chromatographed on silica gel using a gradient of $CH_2Cl_2$ and then $CH_2Cl_2$/MeOH 99:1.

The clean product-containing fractions are combined and concentrated.

Yield: 20.4 g (64% of theory).
TLC system I: Rf=0.79.
HPLC system I: Rt=25.76 min.
FAB-MS: m/e 593 (M+H); m/e 615 (M+Na).

EXAMPLE 67

D-Histidyl-D-phenylalanine benzyl ester dihydrochloride

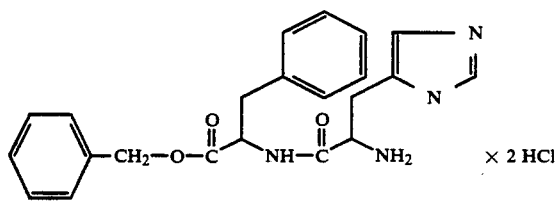 × 2 HCl 10.7 g (18 mmol) of N-2-tert.butoxycarbonyl-N-im-tert.-butoxycarbonyl-D-histidyl-D-phenylalanine benzyl ester (Example 66) are stirred overnight in 100 ml of 4 N HCl (gaseous) in dioxane. The mixture is concentrated almost to dryness, coevaporated with ether, stirred with ether, and the precipitate is filtered off with suction and dried over KOH.

Yield: 7.13 g (85% of theory).
TLC system III: Rf=0.21.
(+)FAB-MS: m/e 393 (M+H).

EXAMPLE 68

D-Histidyl-D-phenylalanine methyl ester dihydrochloride

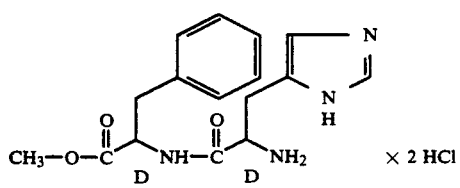 × 2 HCl

The title compound is obtainable analogously to Examples 66 and 67 by coupling D-phenylalanine methyl ester and di-BOC-D-His and subsequent removal of the BOC protecting group.

TLC system III: Rf=0.27.
(+)FAB-MS: m/e 317 (M+H).

EXAMPLE 69

D-Histidyl-D-phenylalanine tart.-butyl ester dihydrochloride

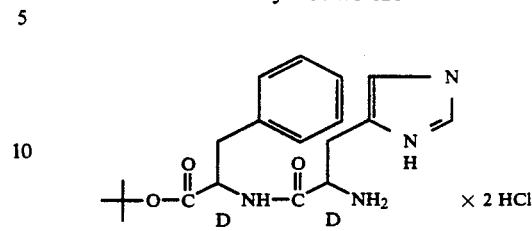 × 2 HCl 5.65 g (10 mmol) of N-α-tert.-butoxycarbonyl-N-im-tert.-butoxycarbonyl-D-histidyl-D-phenylalanine tert.-butyl ester (obtainable from di-BOC-D-His and D-phenyl-alanine tert.-butyl ester analogously to Example 66) are dissolved in 50 ml of CH$_2$Cl$_2$, cooled in an ice bath and 7.8 ml (101 mmol) of trifluoroacetic acid are added. The mixture is stirred for 45 min. and the same amount of trifluoroacetic acid is added once again. After a further 45 minutes in the ice bath, the mixture is concentrated to dryness and the residue is taken up in CH$_2$Cl$_2$. The organic phase is shaken with saturated NaHCO$_3$, washed with saturated sodium chloride solution until neutral, dried over Na$_2$SO$_4$, 5 ml of 4 N HCl in dioxane are added and the mixture is concentrated to dryness.

Yield: 2.36 g (54% of theory).
TLC system III: Rf=0.38.
TLC system IV: Rf=0.17.
(+)FAB-MS: m/e 359 (M+H).

EXAMPLE 70

4-(N-Phthalyl)amino-2-R,S-benzyl-3R,S-hydroxybutyryl-D-histidyl-D-phenylalanine benzyl ester

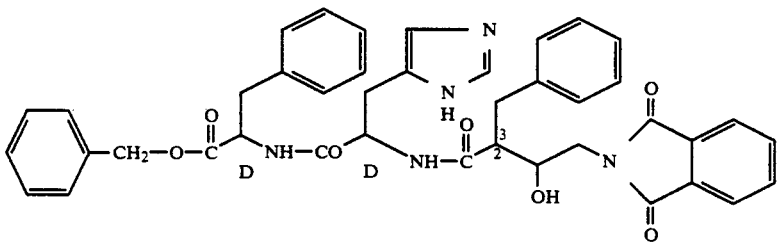

1.35 g (4 mmol) of the compound from Example 5 and 1.91 g (5 mmol) of the compound from Example 67 and dissolved in 40 ml of CH$_2$Cl$_2$ and 2.77 ml (16 mmol) of DIPEA, 703 mg (5.2 mmol) of HOBT and 990 mg (4.8 mmol) of DCC are successively added. The mixture is stirred overnight an d200 mg (1 mmol) of DCC are added once more. After 2 hours, 150 mg of glycine are added, the mixture is concentrated in a rotary evaporator and ethyl acetate is added. The precipitated urea is filtered off and the filtrate is washed with saturated NaHCO$_3$ solution, pH 7 buffer (Merck, article No. 9385) and saturated NaCl solution, dried over Na$_2$SO$_4$ and concentrated. The crude product is chromatographed on silica gel using a gradient of CH$_2$Cl$_2$/MeOH of 100:0 to 95:5.

Yield: 2.14 g (75% of theory).
TLC system I: Rf=0.51 (middle of the spot).
(+)FAB-MS: m/e 714 (M+H),

EXAMPLE 71

4-(N-Phthalyl)amino-2-R,S-benzyl-3R,S-hydroxybutyryl-D-histidyl-D-phenylalanine

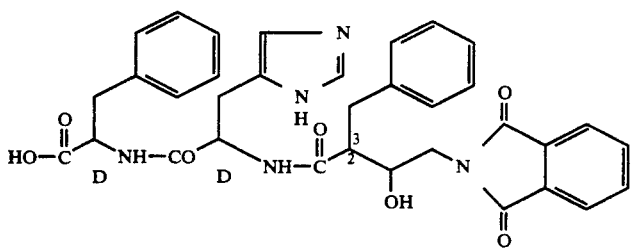

2.1 g (2.9 mmol) of the compound from Example 70 are dissolved in 40 ml of dioxane, 500 mg of Pd/C (10%) are added and, after adding 1 ml of 1 N HCl, the mixture is hydrogenated at 3 bar for 24 hours. The catalyst is filtered off, the filtrate is concentrated and coevaporated to dryness several times with ether. The residue is stirred with diethyl ether, filtered off with suction and dried.

Yield: 1.59 g (64% of theory).
TLC system I: Rf=0.21 =0.30.
TCL system III: Rf=0.06.
(+)FAB-MS: m/e 624 (M+H); m/e 630 (M+Li); m/e 636 (M+2Li−H).

EXAMPLE 27

4-(N-Phthalylamino-2-R,S-benzyl-3R,S-hydroxybutyryl-D-histidyl-D-phenylalanine(cyclopentyl)amide

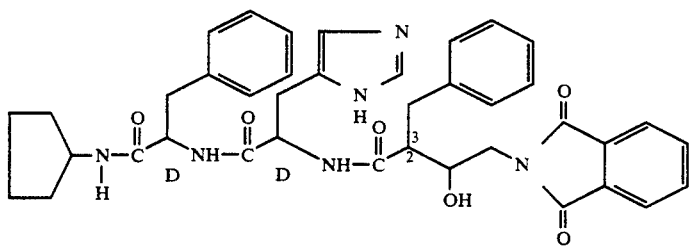

600 mg (0.96 mmol) of the compound from Example 71 are dissolved in 10 ml of CH$_2$Cl$_2$ and 0.2 ml of cyclopentylamine, 150 mg of HOBT and 280 mg of DCC are added successively. The mixture is stirred overnight, precipitated dicyclohexylurea is filtered off, the filtrate is extracted by shaking analogously to Example 70 and the crude product of chromatographed on silica gel.

Yield: 250 mg (38% of theory).
TCL system I: Rf=0.32-0.37.
(+)FAB-MS: m/e 691 (M+H).

EXAMPLE 73

4-(N-tert.-Butoxycarbonyl-N-benzyl)amino-2-R,S-benzyl-3-R,S-hydroxybutyryl-D-histidine methyl ester The title compound is obtained by DCC/HOBT coupling (analogously to Example 70 and 72) of 1.31 g (4.25 mmol) of the compound from Example 9 or a mixture of the compounds from Example 10 and 11 or a mixture of Examples 34–38 with D-histidine methyl ester dihydrochloride, working up and gradient chromatography on silica gel (analogously to Example 82 and 84).

Yield: 780 mg (31.4% of theory).
TLC system I: Rf=0.35-0.44.
(+)FAB-MS: m/e 551 (M+H).

EXAMPLE 74

4-(N-tert.-Butoxycarbonyl-N-benzyl)amino-2-R,S-benzyl-3-R,S-hydroxybutyryl-D-histidine

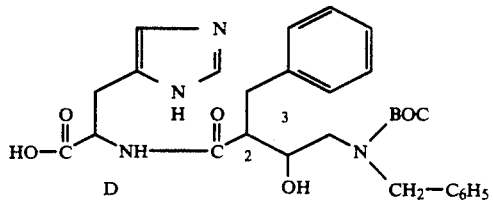

760 mg (1.4 mmol) of the compound from Example 73 are dissolved in 20 ml of dioxane, 1.8 ml of 1 N NaOH are added and the mixture is stirred overnight at room temperature. 10 ml of H$_2$O and 2 ml of 1 N NaOH are added to the mixture and it is stirred at room temperature for 2 hours. The mixture is rendered neutral (1 N HCl), dioxane is evaporated off in a rotary evaporator and the mixture is lyophilized. The crude product is desalted on Mitsubishi Diaion HP 20 using a gradient of H₂O/MeOH 100:0 to 30:70 and eluted. The product-containing fractions are combined, methanol is removed in a rotary evaporator and the solution is freeze-dried.

Yield: 590 mg (78% of theory).
TLC system III: Rf=0.06.
(+)FAB-MS: m/e 537 (M+H); m/e 559 (M+Na); m/e 581 (M+2Na−H).

EXAMPLE 75

4-(N-tert.-Butoxycarbonyl-N-benzyl)amino-2-R,S-benzyl-3-R,S-hydroxybutyryl-histidyl-D-phenylalanine methyl ester

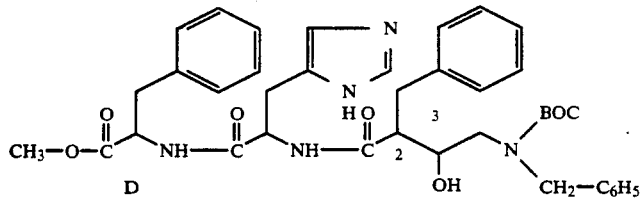

580 mg (1.1 mmol) of the compound from Example 74 and 403 mg (2 mmol) of D-phenylalanine methyl ester hydrochloride are dissolved in 10 ml of CH₂Cl₂ and 697 µl (4 mmol) of DIPEA, 270 mg (2 mmol) of HOBT and 412 mg (2 mol) of DCC are added successively. The mixture is stirred overnight and 200 mg (1 mmol) of D-phenylalanine methyl ester hydrochloride, 350 µl (2 mmol) of DIPEA and 600 mg (3 mmol) of DCC are added once again. After stirring at room temperature for six hours, 500 mg of glycine are added to the mixture and it is stirred overnight. The mixture is made up with 50 ml of CH₂Cl₂, undissolved material is filtered off and the filtrate is concentrated. The residue is taken up in ethyl acetate and washed with saturated NaHCO₃, pH 7 buffer and saturated NaCl solution. The organic phase is dried over Na₂SO₄, concentrated and coevaporated with CH₂Cl₂ once again.

The crude produce is chromatographed on silica gel using a gradient of CH₂Cl₂/MeOH (analogously to Examples 70–72).

The Pauli-positive (TLC spray reagents for histidine) fractions are pooled and, after concentrating, re-chromatographed in the same system, the product-containing eluates are combined, concentrated and dried in a high vacuum.

Yield: 510 mg (67% of theory).
TLC system I: Rf=0.81–0.90.
TLC system II: Rf=0.27–0.37.
(+)FAB-MS: m/e 698 (M+H).

EXAMPLE 76

4-(N-tert.-Butoxycarbonyl-N-benzyl)amino-2-R,S-benzyl-3-R,S-hydroxybutyryl-D-histidyl-D-phenylalanine

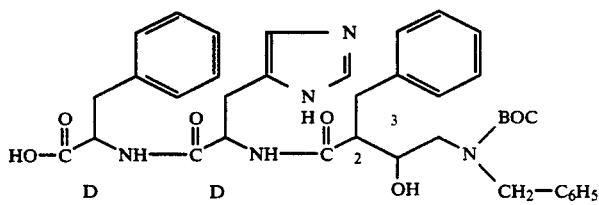

The title compound is obtained from 247 mg (0.354 mmol) of the compound from Example 75 by basic hydrolysis (analogous to Example 74) and desalting of the crude product.

Yield: 137 mg (57% of theory).
TLC system III: Rf=0.03.
(+)FAB-MS: m/e 684 (M+H); m/e 706 (M+Na).

EXAMPLE 77

4-(N-tert.-Butoxycarbonyl-N-benzyl)amino-2-R,S-benzyl-3-R, S-hydroxybutyryl-D-histidyl-D-phenylalanine-(N-morpholino)amide

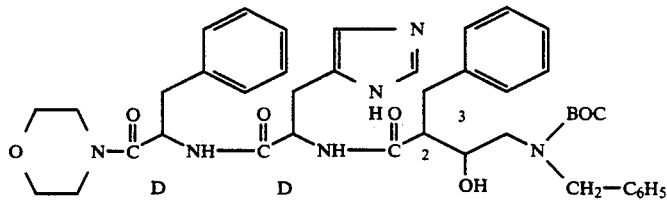

The title compound is obtained starting from 90 mg (146 µmol) of the compound from Example 76 by coupling with morpholine (analogously to Example 72 ) and chromatography of the crude product.

Yield: 77 ml (74% of theory).
TLC system III: Rf=0.26.
(+)FAB-MS: m/e 753 (M+H); m/e 775(M+Na).

EXAMPLE 78

(N-tert.-Butoxycarbonyl)amino-2-R,S-benzyl-3-R,S-hydroxybutyryl-D-histidyl-D-phenylalanine-(2-methylpropyl)amide

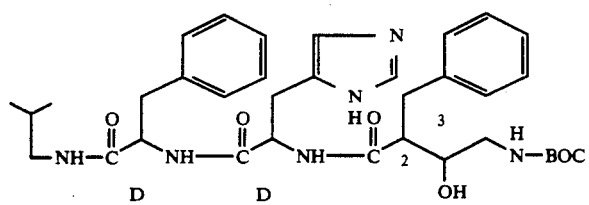

The title compound is obtained starting from the compound of Example 39 or a mixture of the compounds from examples 54–57 by DCC/HOBT coupling (analogously to Examples 70 an d72) or n-PPA coupling (analogously to Example 91 ) using D-histidyl-D-phenylalanine-(2-methylpropyl)amide dihydrochloride (obtainable by catalytic debenzylation of the compound from Example 66, coupling of the product with isobutylamine and reaction of the intermediate with 4 N HCl/dioxane).

Alternatively, the compound from Example 39 or the mixture of compounds from Examples 54–57 can first be reacted with D-histidine methyl ester dihydrochloride (analogously to Example 73). The ester obtained can then be hydrolyzed (analogously to Example 74) and then reacted with D-phenylalanine-(2-methyl)propylamide hydrochloride (analogously to Example 75). Alternatively, the title compound can be obtained by reaction of the compound from Example 39 or a mixture of the compounds from Examples 54–57 in the manner already described for Example 70 with the compound from Example 67, catalytic debenzylation of the intermediate (analogously to Example 71) and subsequent reaction of the resulting acid with isobutylamine (analogously to Example 72). The crude products obtained are extracted by shaking as already described several times and chromatographed on silica gel using $CH_2Cl_2$/MeOH gradients.

Analytical data for Example 78
TLC system I: Rf=0.28–0.37.
(+)FAB-MS: m/e=649 (M+H).

EXAMPLES 79–86 AND EXAMPLES 87–89

The examples shown in Table 6 are prepared by the methods mentioned in Examples 66–78.

Examples 87–89 shown in Table 7 are also prepared by the methods described above. The compound from Example 45 or the mixture of compounds from Examples 58–61 were employed as retrostatin coupling components.

TABLE 5

| Example No. | X | D | E | Z | TLC System Rf Values | (+)FAB-MS |
|---|---|---|---|---|---|---|
| 79 | $CH_3O$ | — | D-His | phthalimido | III: 0.50–0.54<br>IV: 0.13–0.20 | m/e 491 (M + H) |
| 80 | $CH_3O$ | D-Phe | D-His | phthalimido | I: 0.37–0.50 | m/e 638 (M + H) |
| 81 | $CH_3O$ | L-Phe | L-His | phthalimido | IV: 0.33–0.50 | m/e 638 (M + H) |

TABLE 6

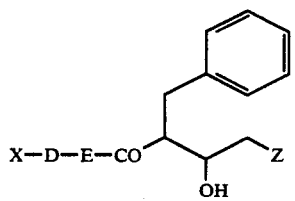

| Example No. | X | D | E | Z | TLC System Rf Values | (+)FAB-MS |
|---|---|---|---|---|---|---|
| 82 | ![isopropyl-NH-] | D-Phe | D-His | phthalimido-N- | I: 0.43–0.49 | m/e 679 (M + H) |
| 83 | ![t-butyl-NH-] | D-Phe | D-His | —N(BOC)CH₂-phenyl | III: 0.25 | m/e 753 (M + H)<br>m/e 775 (M + Na) |
| 84 | ![t-butyl-O-] | D-Phe | D-His | NH—BOC | III: 0.28–0.40<br>IV: 0.38–0.50 | m/e 650 (M + H)<br>m/e 672 (M + Na) |
| 85 | ![benzyl-O-] | D-Phe | D-His | NH—BOC | III: 0.34–0.37 | m/e 684 (M + H)<br>m/e 706 (M + Na) |
| 86 | OH | D-Phe | D-His | NH—BOC | III: 0.03–0.06 | m/e 759 (M + H) |

TABLE 7

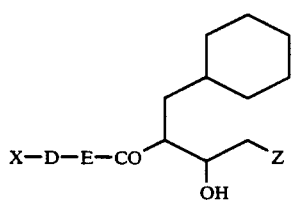

| Example No. | X | D | E | Z | TLC System Rf Values | (+)FAB — MS |
|---|---|---|---|---|---|---|
| 87 | ![benzyl-O-] | D-Phe | D-His | NH—BOC | I: 0.27–0.38 | m/e 690 (M + H)<br>m/e 712 (M + Na) |
| 88 | HO— | D-Phe | D-His | NH—BOC | IV: 0.54–0.60 | m/e 600 (M + H)<br>m/e 622 (M + Na) |
| 89 | ![isopropyl-NH-] | D-Phe | D-His | NH—BOC | III: 0.52–0.64 | m/e 655 (M + H)<br>m/e 677 (M + Na) |

EXAMPLE 90

4-[N-(2-Carboxy)benzoyl]amino-2-R,S-benzyl-3-R,S-hydroxybutyryl-D-histidyl-D-phenylalanine-(2-methyl)propylamide

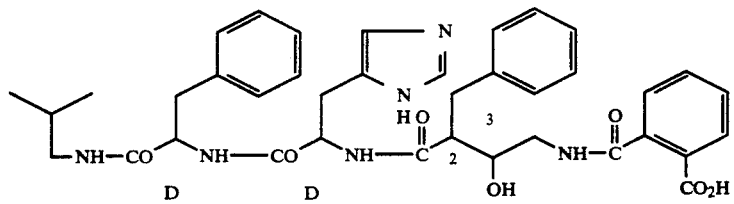

180 mg (250 μmol) of the compound from Example 82 are dissolved in 500 μl of dioxane and 350 μl of N NaOH are added. The mixture is stirred overnight at room temperature, dioxane is removed in a rotary evaporator and the mixture is adjusted to pH 7 with 1 N HCl. The product is extracted into diethyl ether. The organic phase is dried over $Na_2SO_4$ and concentrated.

Yield: 130 mg (35% of theory).
TLC system III: Rf=0.03-0.08.
(+)FAB-MS: m/e 697 (M+H); m/e 719 (M+Na).

EXAMPLE 91

4-[N-(2-Carb)picolyl]amid]-benzoyl)amino-2-R,S-benzyl-3-R,S-hydroxybutyryl-D-histidyl-D-phenylalanine-(2-methyl)propylamide

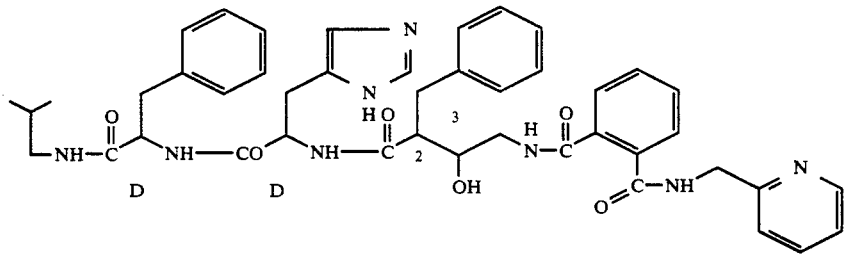

40 mg (57 μmol) of the compound from Example 90 and 7 μl (69 μmol) of 2-picolylamine are dissolved in 2 ml of $CH_2Cl_2$. 100 μl (574 μmol) of DIPEA and, finally, 55 μl (69 μmol) of a 50% strength solution of n-propylphosphonic anhydride in $CH_2Cl_2$ ("PPA", Hoechst AG, are added to the mixture with stirring, which is stirred overnight at room temperature. The mixture is made up to 10 ml using $CH_2Cl_2$ and washed with saturated $NaHCO_3$ solution, pH 7 buffer (Merck, article No. 9439) and saturated NaCl solution, dried over $Na_2SO_4$ and concentrated.

The crude mixture is chromatographed on silica gel 40-63 μm (Merck, article No. 9385) using a gradient of $CH_2Cl_2$/MeOH 100:0-95:5. The product-containing fractions are combined, concentrated and dried in a high vacuum.

Yield: 7 mg (16% of theory).
TLC system III: Rf=0.17-0.29.
(+)FAB-MS: m/e 787 (M+H); m/e 809 (M+Na).

EXAMPLES 92-95

The compounds shown in Table 8 were prepared from the compounds of Examples 72 and 90 in analogy to Examples 90 and 91.

TABLE 8

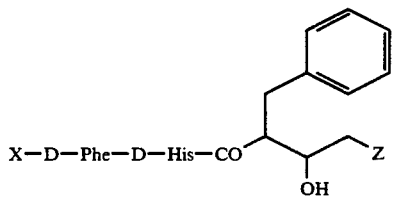

| Ex. No. | X | Z | TLC System Rf Value | (+)FAB − MS |
|---|---|---|---|---|
| 92 | cyclopentyl-NH | -NH-CO-(2-COOH-phenyl) | III: 0.03-0.07 | m/e 709 (M + H) m/e 731 (M + Na) |

TABLE 8-continued

X—D—Phe—D—His—CO—CH(CH₂C₆H₅)—CH(OH)—CH₂—Z

| Ex. No. | X | Z | TLC System Rf Value | (+)FAB — MS |
|---|---|---|---|---|
| 93 | cyclopentyl-NH | —NH—CO—C₆H₄(o)—CO—NH-cyclopentyl | I: 0.22 | m/e 776 (M + H)<br>m/e 798 (M + Na) |
| 94 | cyclopentyl-NH | —NH—CO—C₆H₄(o)—CO—NH—CH₂-(2-pyridyl) | III: 0.20–0.28 | m/e 799 (M + H) |
| 95 | isobutyl-NH | —NH—CO—C₆H₄(o)—CO—NH-isobutyl | III: 0.52–0.60 | m/e 752 (M + H)<br>m/e 774 (M + Na) |

EXAMPLES 96–102

The compounds shown in Table 9 were prepared from the corresponding precursors by removal of the N-tert.-butoxycarbonyl groups with 4 N HCl in dioxane in analogy to Example 40.

X—D—Phe—D—His—CO—CH(CH₂R¹)—CH(OH)—CH₂—Z × 2 HCl

| Ex. No. | X | R¹ | Z | TLC System Rf Value | (+)FAB — MS |
|---|---|---|---|---|---|
| 96 | CH₃O | C₆H₅ | —NH—C₆—H₅ | III: 0.18–0.12 | m/e 598 (M |
| 97 | morpholino | C₆H₅ | —NH—C₆H₅ | III: 0.15 | m/e 653 (M + H)<br>m/e 675 (M + Na) |
| 98 | piperazino-NH | C₆H₅ | —HN—C₆H₅ | III: 0.12 | m/e 653 (M + H)<br>m/e 675 (M + Na) |
| 99 | C₆H₅—CH₂O- | C₆H₅ | —NH₂ | III: 0.02–0.10 | m/e 684 (M + H) |
| 100 | isobutyl-NH | C₆H₅ | —NH₂ | IV: 0.30–0.36 | m/e 549 (M + H) |

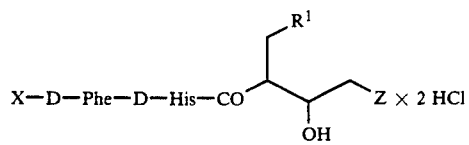

| Ex. No. | X | R¹ | Z | TLC System Rf Value | (+)FAB − MS |
|---|---|---|---|---|---|
| 101 | (benzyl-CH₂O−) | $C_6H_{11}$ | −NH₂ | III: 0.14−0.40 | m/e 590 (M + H) |
| 102 | (isopropyl-NH−) | $C_6H_{11}$ | −NH₂ | III: 0.16−0.20<br>IV: 0.18−0.30 | m/e 555 (M + H) |

EXAMPLE 103

4-[N-Benzyl-N-(3-pyridyl)acetyl]amino-2-R,S-benzyl-3-R,S-hydroxybutyryl-D-histidyl-D-phenylalanine methyl ester

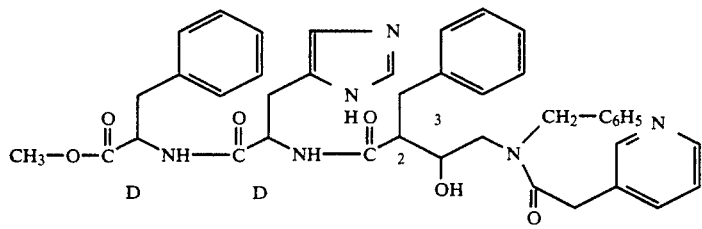

50 mg (84 μmol) of the compound from Example 90 and 17.4 mg (100 μmol) of 3-pyridylacetic acid are dissolved in 1 ml of CH₂Cl₂ and 146 μl (836 μmol) of DIPEA and 80 μl (100 μmol) of a 50% strength solution of n-propylphosphonic anhydride in CH₂Cl₂ ("n-PPA", Hoechst AG) in dichloromethane are added successively. The mixture is stirred overnight, made up to 10 ml and washed with saturated NaHCO₃ solution, pH 7 buffer (Merck, article No. 9439) and saturated NaCl solution, dried over Na₂SO₄ and concentrated.

The crude product is chromatographed on 3.5 g of silica gel 40–63 μm (Merck, article No. 9385) using a gradient of CH₂Cl₂/MeOH of 100:0–95:5. The product-containing, Pauli-positive fractions are combined and concentrated.

Yield: 18 mg (28.6% of theory).
TLC system III: Rf=0.32.

HPLC system II: Rf=1.73 min., 2.12 min., 2.80 min. and 3.53 min.

(+)FAB-MS: m/e 717 (M+H).

EXAMPLES 104–108

The compounds shown in Table 10 were prepared from the precursors indicated in Table 9 by n-PPA coupling with the corresponding acids or amino acid derivatives with standard working up and column chromatography in analogy to Example 103.

Alternatively, a DCC-HOBT coupling of the corresponding educts can also be carried out.

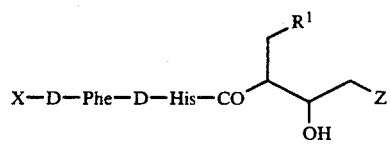

| Example No. | X | R¹ | Z | TLC System Rf Values | (+)FAB − MS |
|---|---|---|---|---|---|
| 104 | (benzyl-CH₂O−) | $C_6H_5$ | (−HN−CO−CH(iBu)−NHCO−CH₂−2-pyridyl) | III: 0.21−0.35 | m/e 816 (M + H) |

-continued

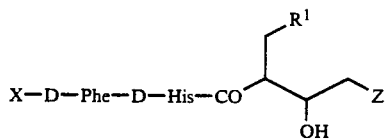

X—D—Phe—D—His—CO-CH(CH2R¹)-CH(OH)-CH2-Z

| Example No. | X | R¹ | Z | TLC System Rf Values | (+)FAB — MS |
|---|---|---|---|---|---|
| 105 | iPr-NH- | $C_6H_5$ | -HN-CO-CH(iBu)-morpholinyl (D) | IV: 0.44, 0.45, 0.49, 0.53 | m/e 732 (M + H)<br>m/e 675 (M + H) |
| 106 | C6H5-CH2O- | $C_6H_{11}$ | -HN-CO-CH(iBu)-NHCO-CH2-(2-pyridyl) (D) | III: 0.49, 0.54 0.57 0.63 | m/e 822 (M + H) |
| 107 | iPr-NH- | $C_6H_{11}$ | -HN-CO-CH(iBu)-NHCO-O-CH2CH3 (D) | III: 0.40–0.50 | m/e 740 (M + H)<br>m/e 762 (M + N) |
| 108 | iPr-NH- | $C_6H_{11}$ | -NH-CO-iBu | III: 0.43–0.50 | m/e 639 (M + H)<br>m/e 661 (M + Na) |

EXAMPLE 109

(4S)-3-[4-(N-tert.-Butoxycarbonyl-N-benzyl)amino-(2R)-2-cyclohexylmethyl-(3R,S)-3-hydroxybutyryl]-4-benzyloxazolidin-2-one

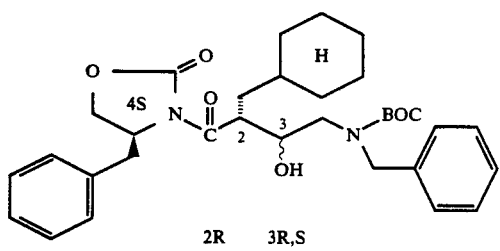

The title compound is obtained pure by chromatography analogously to Example 22 starting from the compound form Example XVIII and the aldehyde from Example IV.

HPLC system II: Rt=91.73 min. (4R,2R,3R-isomer). Rt=117.52 min. (4S,2R,3S-isomer.

(+)FAB-MS: m/e 565 (M+H); m/e 587 (M+Na).

EXAMPLE 110

4-(N-tert.-Butoxycarbonyl-N-benzyl)amino-(2R)-2-cyclohexylmethyl-(3R,S)-3-hydroxybutyric acid

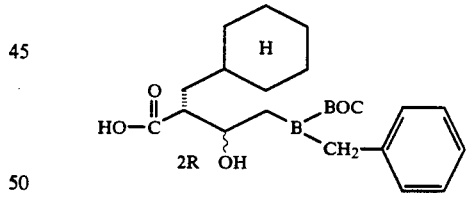

The title compound is obtained from the compound of Example 109 by removal of the chiral auxiliary reagent and subsequent chromatography (as described in Example 34).

TLC system II: Rf=0.42 (2R, 3R-isomer) 0.38 (2R, 3S-isomer).

HPLC system III: Rt=7.605 min. (ret. index 956), 2R, 3R-isomer. Rt=7.754 min. (ret. index 979), 2R, 3S-isomer.

(+)FAB-MS: m/e 444 (M+K); m/e 482 (M+2K'H) m/e 520 (M+3K−2H).

EXAMPLES 111–114

The compounds (Table 11) are obtained by chromatography of the corresponding diastereomer mixtures (Example 13 for Examples 111 and 114 and Example 110 for Examples 112 and 113) on silica gel using a CH₂Cl₂/MeOH gradient (analogously to Example 10 and Example 11). The 2R,3R or 2S,3S-isomers elute first, then the 2R,3S or 2S,3R-isomers. Alternatively, the preparation of Examples 111-114 can be carried out by removal of the optical auxiliary reagents form corresponding enantiomerically pure precursors (analogously to Examples 34-37).

TABLE 11

HO—C(=O)—R¹—N(BOC)—CH₂—C₆H₅

| Ex. No. | R¹ | Configuration | HPLC System II; R_t |
|---|---|---|---|
| 111 | (cyclohexyl-CH(CH₃)-CH(OH)-) | 2S, 3R | 7.754 min |
| 112 | (cyclohexyl-CH(CH₃)-CH(OH)-) | 2R, 3S | 7.754 min |
| 113 | (cyclohexyl-CH(CH₃)-CH(OH)-) | 2R, 3R | 7.605 min |
| 114 | (cyclohexyl-CH(CH₃)-CH(OH)-) | 2S, 3S | 7.605 min |

EXAMPLES 115-118

The compounds shown in Table 12 were prepared from the corresponding enantiomeric precursors of Examples 34-37 by removal of the BOC protecting group in analogy to Example 40.

TABLE 12

HO—C(=O)—R¹—NH—CH₂—C₆H₅ × HCl

| Ex. No. | R¹ | Configuration | MS — DCI |
|---|---|---|---|
| 115 | (cyclohexyl-CH(CH₃)-CH(OH)-) | 2S, 3R | m/e = 306 (M + H) |
| 116 | (cyclohexyl-CH(CH₃)-CH(OH)-) | 2R, 3S | |
| 117 | (cyclohexyl-CH(CH₃)-CH(OH)-) | 2R, 3R | |
| 118 | (cyclohexyl-CH(CH₃)-CH(OH)-) | 2S, 3S | m/e = 306 (M + H) |

The compounds shown in the following Tables 13-24 are obtained from the corresponding precursors according to methods which have already been described or known methods of peptide chemistry.

| Table | Examples | Precursor(s) |
|---|---|---|
| 13 | 119-123; 129 | Example 7 |
| 14 | 124-128; 130 | Example 8 |
| 15 | 131-135 | Examples 10-11 |
| 16 | 136-139 | Examples 34-37 |
| 17 | 140-143 | Examples 136-139 |
| 18 | 144-147 | Examples 140-143 |
| 19 | 148-151 | Examples 34-37 |
| 20 | 152-157 | Examples 111 + 114 |
| 21 | 158-161 | Examples 58-62 |
| 22 | 162-165 | Examples 158-161 |
| 23 | 166-169 | Examples 162-165 |
| 24 | 170-173 | Examples 111 + 114 |

TABLE 13

Structure: X—D—E—CO—CH(CH2Ph)—CH(OH)—CH2—N(phthalimide)

| Example No. | X | D | E | TLC System Rf Values | HPLC System Rt Values | (+)FAB − MS |
|---|---|---|---|---|---|---|
| 119 | Ph(H3C)CH—NH, R-(+)- | — | — | I: 0.89 | II: 5.37 min | m/e 433 (M + H) |
| 120 | 4-Cl-C6H4-NH | — | — | | II: 6.32 min | |
| 121 | (CH3)2CH—NH (isopropyl-NH) | D-Phe | D-His | | II: 4.34 min | m/e 679 (M + H) |
| 122 | (CH3)2CH—NH | L-Phe | L-His | | II: 4.65 min | m/e 701 (M + Na) |
| 123 | (CH3)2CH—NH | D-Phe | D-Val- | | II: 8.19 min | m/e 641 (M + H) |
| 129 | CH3O | D-Phe | thiazolidine-4-carbonyl (S—S ring with —C(O)—CH—NH, D,L) | | II: 7.78 min (both isomers) | m/e 662 (M + H); m/e 684 (M + Na) |

TABLE 14

Structure: X—D—E—CO—CH(CH2Ph)—CH(OH)—CH2—N(phthalimide)

| Example No. | X | D | E | TLC System Rf Values | HPLC System Rt Values | (+)FAB-MS |
|---|---|---|---|---|---|---|
| 124 | C6H5(CH3)CH—NH—, R-(+)- | — | — | I: 0.82 | II: 5.11 min | m/e 433 (M+H) |
| 125 | 4-Cl-C6H4-NH | — | — | | II: 6.32 min | |
| 126 | (CH3)2CH—NH | D—Phe | D—His | | II: 4.68 min | m/e 679 (M+H) |
| 127 | " | L—Phe | L—His | | II: 4.36 min | m/e 701 (M+Na) |

TABLE 14-continued

Structure: X—D—E—CO—O—CH(CH2Ph)—CH(OH)—CH2—N(phthalimide)

| Example No. | X | D | E | TLC System Rf Values | HPLC System Rt Values | (+)FAB-MS |
|---|---|---|---|---|---|---|
| 128 | iBu-NH | D—Phe | D—Val | | II: 7.52 min | m/e 641 (M+H) |
| 130 | CH3O | D—Phe | (S,S-dithiolane-CH(NH)—CO—) D, L | | II: 6.95 min / 8.76 min | m/e 662 (M+H); m/e 684 (M+Na) |

TABLE 15

Structure: X—CO—C(2)(CH2Ph)—C(3)(OH)—CH2—N(Bn)(Boc)

| Example No. | X | Configuration | TLC System Rf Values | HPLC System II Rt Values | (+)FAB-MS |
|---|---|---|---|---|---|
| 131 | PhCH(CH3)NH  R-(+) | 2R, 3R; 2S, 3S | IX: 0.40 / 0.36 | 17.45 min / 18.31 min | m/e = 503 (M+H) |
| 132 | PhCH(CH3)NH | 2R, 3S; 2S, 3R | IX: 0.29 / 0.24 | 23.50 min / 25.03 min | m/e = 503 (M+H) |
| 133 | Ph-CH(COOEt)-O  S-(+)- | 2R, 3S; 2S, 3S | VII: 0.38 / 0.33 | 63.1 min, broad | m/e = 562 (M+H) |
| 134 | Ph-CH(COOEt)-O  S-(+)- | 2R, 3S; 2S, 3R | VIII: 0.91 / 0.85 | 69.8 min, broad | |

TABLE 15-continued

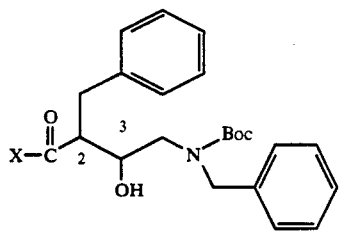

| Example No. | X | Configuration | TLC System Rf Values | HPLC System II Rt Values | (+)FAB-MS |
|---|---|---|---|---|---|
| 135 | 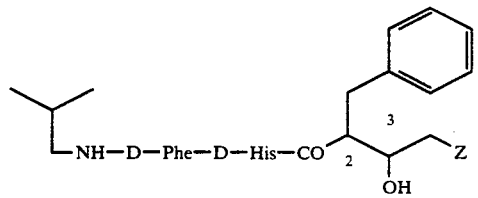 | 2R, 3R; 2S, 3S | | 37.87 min<br>38.17 min | m/e = 669 (M+H) |

TABLE 16

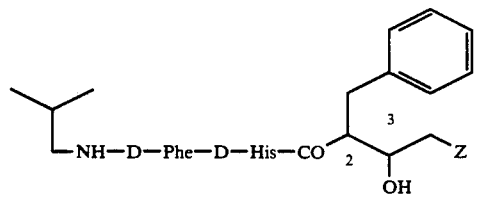

| Example No. | Configuration | Z | TLC System Rf Values | HPLC System II Rt Values | (+)FAB-MS |
|---|---|---|---|---|---|
| 136 | 2S, 3R | NH—BOC | | 4.37 min | m/e 655 (M+Li) |
| 137 | 2R, 3S | NH—BOC | | 4.25 min | m/e 655 (M+Li) |
| 138 | 2R, 3R | NH—BOC | | 3.89 min | m/e 655 (M+Li) |
| 139 | 2S, 3S | NH—BOC | | 3.69 min | m/e 655 (M+LI) |

TABLE 17

| Example No. | Configuration | Z | TLC System Rf Values | HPLC System Rt Values | (+)FAB-MS |
|---|---|---|---|---|---|
| 140 | 2S, 3R | NH$_2$ × HCl | III: 0.05 | | m/e 549 (M+H),<br>m/e 571 (M+Na) |
| 141 | 2R, 3S | NH$_2$ × HCl | III: 0.06 | | m/e 549 (M+H),<br>m/e 571 (M+Na) |
| 142 | 2R, 3R | NH$_2$ × HCl | III: 0.06 | | m/e 549 (M+H),<br>m/e 571 (M+Na) |
| 143 | 2S, 3S | NH$_2$ × HCl | III: 0.05 | | m/e 549 (M+H),<br>m/e 571 (M+Na) |

TABLE 18 iBu—NH—D—Phe—D—His—CO—CH(3-CH2C6H5)—CH(OH)—CH2—Z (positions 2,3 indicated)

| Example No. | Configuration | Z | TLC System Rf Values | HPLC System II Rt Values | (+)FAB-MS |
|---|---|---|---|---|---|
| 144 | 2S, 3R | NH—D—Leu—NHCOOC$_2$H$_5$ | I: 0.31 | 4.73 min | m/e 734 (M+H), m/e 756 (M+Na) |
| 145 | 2R, 3S | —NH—C(=O)—CH(D)(CH$_2$CH(CH$_3$)$_2$)—NHCOO—C$_2$H$_5$ | I: 0.37 | 4.29 min | m/e 734 (M+H), m/e 756 (M+Na) |
| 146 | 2R, 3R | —NH—C(=O)—CH(D)(CH$_2$CH(CH$_3$)$_2$)—NHCO—O—C$_2$H$_5$ | I: 0.41 | 4.68 min | m/e 734 (M+H), m/e 756 (M+Na) |
| 147 | 2S, 3S | —NH—C(=O)—CH(D)(CH$_2$CH(CH$_3$)$_2$)—NHCOO—C$_2$H$_5$ | I: 0.35 | 4.14 min | m/e 734 (M+H), m/e 756 (M+Na) |

TABLE 19

CH$_3$O—D—Phe—D—His—CO—CH(3-CH$_2$C$_6$H$_5$)—CH(OH)—CH$_2$—Z

| Example No. | Configuration | Z | TLC System Rf Values | HPLC System II Rt Values | (+)FAB-MS |
|---|---|---|---|---|---|
| 148 | 2S, 3R | —N(BOC)(C$_6$H$_5$) | | 14.64 min | m/e 698 (M+H), m/e 720 (M+Na) |
| 149 | 2R, 3S | —N(BOC)(C$_6$H$_5$) | | | m/e 698 (M+H), m/e 720 (M+Na) |
| 150 | 2R, 3R | —N(BOC)(C$_6$H$_5$) | | | m/e 698 (M+H), m/e 720 (M+Na) |
| 151 | 2S, 3S | —N(BOC)(C$_6$H$_5$) | | 11.25 min | m/e 698 (M+H), m/e 720 (M+Na) |

TABLE 20 iBu-NH—D—Phe—D—His—CO-CH(CH₂-Cyclohexyl)-CH(OH)-CH₂-Z
(positions 2, 3 indicated)

| Example No. | Configuration | Z | TLC System Rf Values | HPLC System II Rt Values | (+)FAB-MS |
|---|---|---|---|---|---|
| 152 | 2S, 3S | N(BOC)-CH₂-phenyl | I: 0.56 | 24.06 min | m/e 745 (M+H) |
| 153 | 2S, 3R | N(BOC)-CH₂-phenyl | I: 0.56 | 29.96 min | m/e 745 (M+H) |
| 154 | 2S, 3S | NH-CH₂-phenyl × HCl | IV: 0.16 | | m/e 645 (M+H) |
| 155 | 2S, 3R | NH-CH₂-phenyl × HCl | IV: 0.16 | | m/e 645 (M+H) |
| 156 | 2S, 3S | N(CH₂-phenyl)-CO-CH(CH₂CH(CH₃)₂)-NHCO-O-CH₂CH₃ (D) | I: 0.56 | 19.15 min | m/e 830 (M+H), m/e 836 (M+Li), m/e 852 (M+Na) |
| 157 | 2S, 3R | N(CH₂-phenyl)-CO-CH(CH₂CH(CH₃)₂)-NHCO-O-CH₂CH₃ (D) | III: 0.56 | 24.03 min | m/e 830 (M+H), m/e 836 (M+Li), m/e 852 (M+Na) |

TABLE 21 iBu-NH—D—Phe—D—His—CO-CH(CH₂-Cyclohexyl)-CH(OH)-CH₂-Z

| Example No. | Configuration | Z | TLC System Rf Values | HPLC System II Rt Values | (+)FAB-MS |
|---|---|---|---|---|---|
| 158 | 2S, 3R | —NH—BOC | III: 0.47 | 7.37 min | m/e 655 (M+H) |
| 159 | 2R, 3S | —NH—BOC | | | |
| 160 | 2R, 3R | —NH—BOC | | | |

TABLE 21-continued

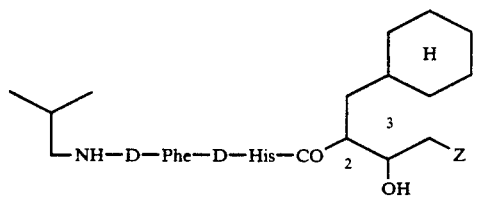

| Example No. | Configuration | Z | TLC System Rf Values | HPLC System II Rt Values | (+)FAB-MS |
|---|---|---|---|---|---|
| 161 | 2S, 3R | —NH—BOC | III: 0.43 | 6.03 min | m/e 655 (M+H) |

TABLE 22

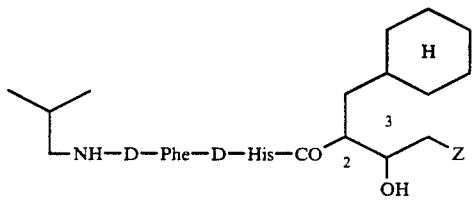

| Example No. | Configuration | Z | TLC System Rf Values | HPLC System II Rt Values | (+)FAB-MS |
|---|---|---|---|---|---|
| 162 | 2S, 3R | NH$_2$ × HCl | | | m/e 555 (M+H) m/e 561 (M+Li) |
| 163 | 2R, 3S | NH$_2$ × HCl | | | m/e 555 (M+H) m/e 561 (M+Li) |
| 164 | 2R, 3R | NH$_2$ × HCl | | | m/e 555 (M+H) m/e 561 (M+Li) |
| 165 | 2S, 3S | NH$_2$ × HCl | | | m/e 555 (M+H), m/e 561 (M+Li) |

TABLE 23

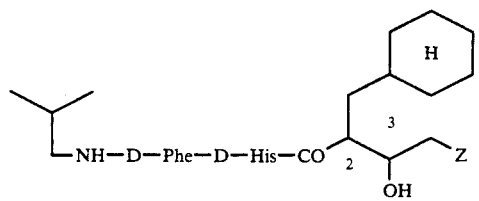

| Example No. | Configuration | Z | TLC System Rf Values | HPLC System II Rt Values | (+)FAB-MS |
|---|---|---|---|---|---|
| 166 | 2S, 3R | ![structure with -NHCO-D-NHCO-O-CH3 and isobutyl] | | | m/e 740 (M+H) |
| 167 | 2R, 3S | ![structure with -NHCO-NHCOO-CH3 and isobutyl] | | | m/e 740 (M+H) |
| 168 | 2R, 3R | ![structure with -NHCO-NHCOO-CH3 and isobutyl] | | | m/e 740 (M+H) |

TABLE 23-continued iBu—NH—D—Phe—D—His—CO—C(3)H(CH₂-cyclohexyl)—C(2)H(OH)—CH₂—Z

| Example No. | Configuration | Z | TLC System Rf Values | HPLC System II Rt Values | (+)FAB-MS |
|---|---|---|---|---|---|
| 169 | 2S, 3S | —NHCO—CH(iBu)—NHCOO—CH₂CH₃ | III: 0.39 | 5.59 min | m/e 740 (M+H) m/e 746 (M+Li) |

TABLE 24

X—(D—Phe)—E—CO—C(3)H(CH₂-cyclohexyl)—C(2)H(OH)—CH₂—N(Boc)(CH₂-phenyl)

| Example No. | X | E | Configuration | TLC System Rf Values | HPLC System II Rt Values | (+)FAB-MS |
|---|---|---|---|---|---|---|
| 170 | iPr—NH— | D—Val | 2S, 3S | I: 0.79 | Rt = 63.82 min | m/e 713 (M+Li) |
| 171 | iPr—NH— | D—Val | 2S, 3R |  | Rt = 82.71 | m/e 713 (M+Li) |
| 172 | CH₃O— | —CO—CH(NH—)—CH(S—S) cyclic R, S | 2S, 3S |  |  |  |
| 173 | CH₃O— | —CO—CH(NH—)—CH(S—S) cyclic R, S | 2S, 3R |  |  |  |

EXAMPLE 174

(4s)-3-[4-(N-Benzyl)amino-2RS)-2-benzyl-(3S)-3-hydroxybutyryl]-4-(2-propyl)oxazolidin-2-one hydrochloride

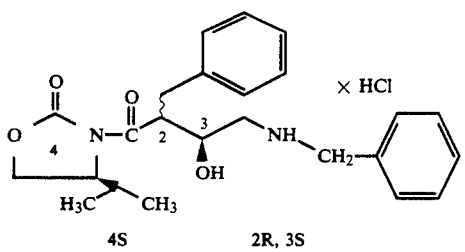

The title compound is obtained by removal of the BOC protecting group (analogously to Example 40) from 4.19 g (8.2 mmol) of a mixture of Examples 19 and 20.

Yield: 3.38 g (92% of theory).
TLC system IV: 0.46 and 0.41.
(+)FAB-MS: m/e 411 (M+H).

EXAMPLE 175

(4R,5S)-3-[4-(N-Benzyl)amino-(2S)-2-benzyl-(3R,S)-3-hydroxy-butyryl]-4-methyl-5-phenyloxazolidin-2-one hydrochloride

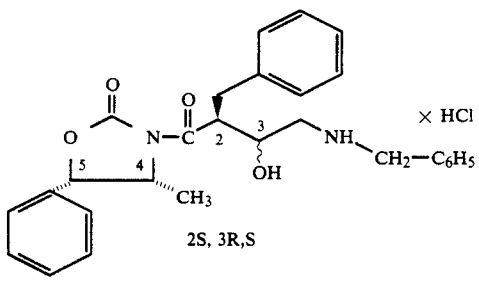

The title compound is obtained from 6.96 g (12.4 mmol) of Example 26 analogously to Example 174.

Yield: 4.68 g (76% of theory).
TLC system III: Rf=0.56 and 0.48.
(+)FAB-MS: m/e 459 (M+H).

EXAMPLE 176

(4R)-3-[4-(N-Benzyl)amino-(2-S)-2-benzyl-(3R,S)-3-hydroxybutyryl]-4-benzyl-oxazolidin-2-one hydrochloride

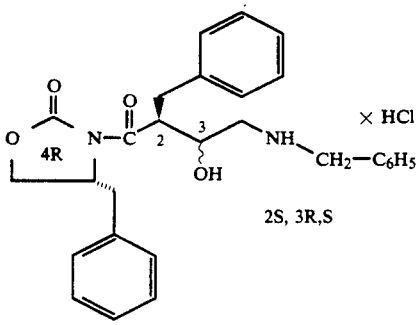

The title compound is obtained from 14.57 g (27.5 mol) of Example 22 analogously to Example 174.

Yield: 10 g (83.4% of theory).
TLC system III: Rf=0.58 and 0.52.
(+)-FAB-MS: m/e 465 (M+H).

EXAMPLE 177

(4S)-3-[4-Amino-(2R,S)-2-benzyl-(3S)-3-hydroxy-butyryl]-4-(2-propyl)oxazolidin-2-one hydrochloride (Example 19)

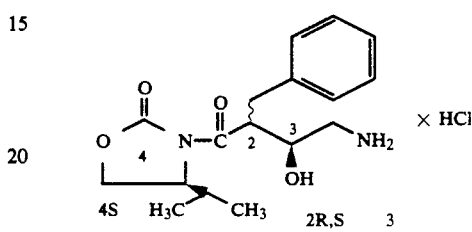

300 mg (0.67 mmol) of the compound of Example 174 are dissolved in about 120 ml of dioxane/methanol/water 60/40/20 and, after addition of 150 mg of Pd (OH)$_2$, hydrogenated at 3.5 bar. After 6 hours, catalyst is filtered off, dioxane/methanol is removed in a rotary evaporator, and the residue is diluted with water and lyophilized.

Yield: 240 mg (100% of theory).
TLC system V: Rf=0.63.
(+)FAB-MS m/e 321 (M+H); m/e 327 (M+Li); M/e 343 (M+Na).

EXAMPLE 178

(4R,5S)-3-[4-(N-Acetyl-N-benzyl)amino-(2S)-2-benzyl-(3R)-3-hydroxy-butyryl]-4-methyl-5-phenyl-oxazolidin-2-one

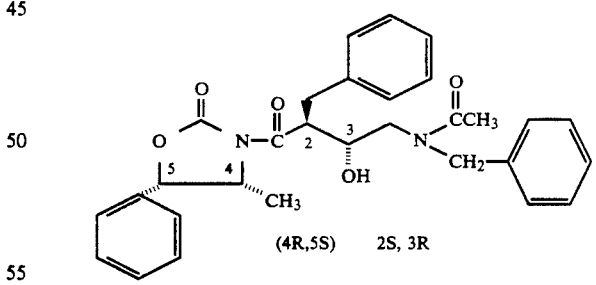

The title compound is obtained starting from (4R,5S)-3-[4-(N-benzyl)amino-(2S)-2-benzyl-(3R)-3-hydroxy-butyryl]-4-methyl-5-phenyl-oxazolidin-2-one hydrochloride (obtainable from Example 27 by removal of the BOC protecting group analogously to Example 175) by PPA coupling with acetic acid (analogously to Example 91) and silica gel chromatography.

TLC system II: Rf=0.56.
HPLC system II: Rt=10.75 min.
(+)FAB-MS m/e 501 (M+H): m/e 507 (M+Li.

EXAMPLE 179

(4R,5S)-3-[4-(N-Benzyl)-N-({N-ethoxycarbonyl}-D-leucyl)amino-(2S)-2-benzyl-(3R,S)-3-hydroxy-butyryl]-4-methyl-5-phenyl-oxazolidin-2-one

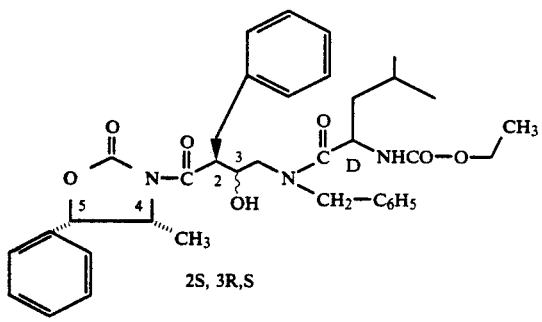

The title compound is obtained starting from the compound of Example 175 by PPA coupling (analogously to Example 91) with N-ethoxycarbonyl-D-leucine and chromatography of the crude product.

TLC system II: Rf=0.68 and 0.57.
HPLC system II: Rt=38.77 min. and 46.17 min.
(+)FAB-MS m/e 644 (M+H); m/e 650 (M+Li).

EXAMPLE 180

(4R)-3-[4-N-Benzyl-N-({N-ethoxycarbonyl}-D-leucyl-amino-(2S)-2-benzyl-(3R,S)-3-hydroxy-butyryl]-4-benzyl-oxazolidin-2-one

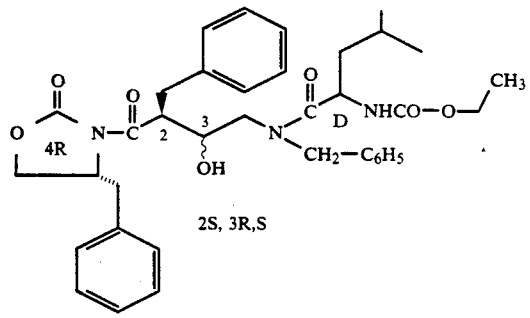

The title compound is obtained analogously to Example 179 starting from the compound from Example 176.
TLC system II: Rf=0.66 and 0.61.
HPLC system II: Rt=68.50 min. and 85.68 min.
(+)FAB-MS m/e 650 (M+H); m/e 672 (M+Na).

EXAMPLE 181

Benzyl (2R,S)-2-benzyl-(3R,S)-3-hydroxy-3-[N-tert.-butoxycarbonyl-(2'S)-pyrrolidyl-(2)]propionate

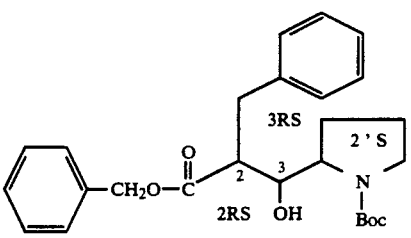

The title compound is obtained analogously to Example 4 from 40.9 g (170.5 mmol) of Example I and 30.9 g (155 mmol) of Example XIX. The crude product (74g) is chromatographed analogously.
Yield: 18.89 g (27.6% of theory).
TLC system XV: Rf=0.10-0.20 (stereoisomer mixture).
(+)FAB-MS m/e 440 (M+H); m/e 462 (M+Na).

EXAMPLE 182

(2R,S)-2-Benzyl-(3R,S)-3-hydroxy-3-[N-tert.-butoxycarbonyl-(2'S)-pyrolidyl-(2)]propionic acid

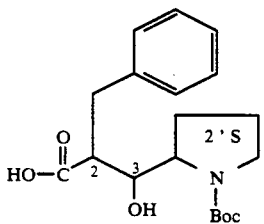

The title compound is obtained analogously to Example 9 from 3.64 g (8.28 mmol) of the compound from Example 181.
Yield: 1.65 g (57% of theory).
TLC system I: Rf=0.58.
(+)FAB-MS m/e 388 (M+K); m/e 426 (M+2K-H).

EXAMPLE 183

(2R,S)-2-Benzyl-(3R,S)-3-hydroxy-3-[N-tert.-butoxycarbonyl-(2'S)-pyrrolidyl-(2)]propionyl-D-asparaginyl-D-phenylalanine benzyl ester

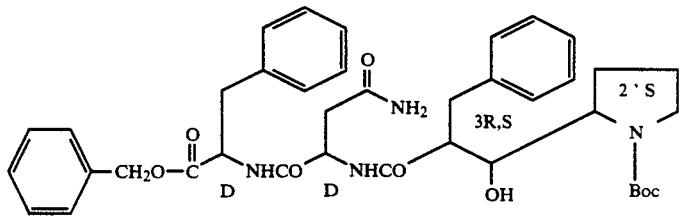

The title compound is obtained analogously to Example 70 from the compound of Example 182 and D-asparaginyl-D-phenylalanine benzyl ester hydrochloride (obtainable from D-phenylalanine benzyl ester and Boc-D-asparagine analogously to Examples 66 and 67).

TLC system I; Rf=0.48–0.58.
(+)FAB-MS m/e 701 (M+H); m/e 723 (M+Na).

EXAMPLE 184

(2R,S)-2-Benzyl-(3R,S)-3-hydroxy-3-[N-tert.-butoxycarbonyl-(2'S)-pyrrolidyl-(2)]propionyl-D-asparaginyl-D-phenylalanine

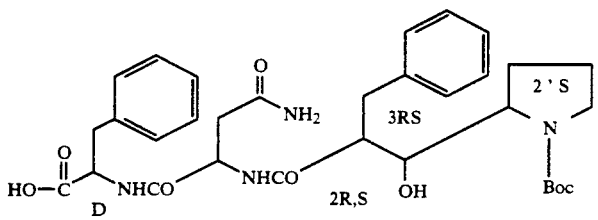

The title compound is obtained analogously to Example 71 from the compound of Example 183.
TLC system IV: Rf:=).26.
(+)FAB-MS m/e 611 (M+H) m/e 633 (M+Na).

EXAMPLE 185

(2R,S)-2-Benzyl-(3R,S)-3-hydroxy-[(2'S)-pyrrolidyl-(2)]propionyl-D-asparaginyl-D-phenylalanine benzyl ester hydrochloride

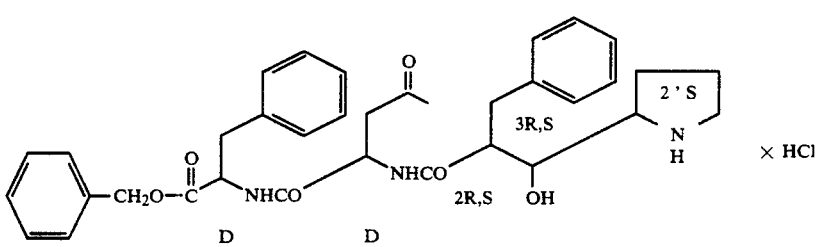

The title compound is obtained from the compound of Example 183 by removal of the Boc protecting group (analogously to Example 67).
TLC system III: 0.17.
(+)FAB-MS: m/e 601 (M+H).

EXAMPLE 186

(2R,S)-2-Benzyl-(3R,S)-3-hydroxy-[N-{tert.-butoxycarbonyl-D-leucyl}-(2'S)-pyrrolidyl-(2)]propionyl-D-asparaginyl-D-phenylalanine benzyl ester

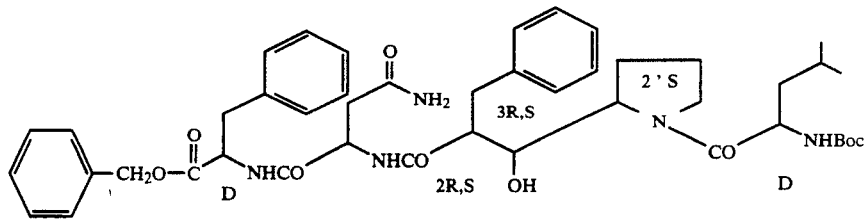

The title compound is obtained analogously to Example 107 from the compound of Example 185 and Boc-D-Lue.
TLC system I: Rf=0.61.
(+)FAB-MS: m/e 814 (M+H), m/e 836 (M+Na).

EXAMPLE 187

(2R,S)-2-Benzyl-(3R,S)-3-hydroxy-[N-{D-leucyl}-(2'S)-pyrrolidyl-(2)]propionyl-D-asparaginyl-D-phenylalanine benzyl ester hydrochloride

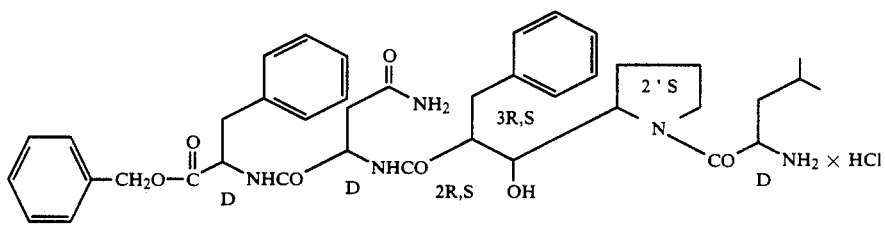

The title compound is obtained analogously to Example 185 from the compound of Example 186.
TLC system IV: Rf=0.20,
(+)FAB-MS: m/e 714 (M+H); m/e 736 (M+Na)

EXAMPLE 188

(2R,S)-2-Benzyl-(3R,S)-3-hydroxy-[N-{tert.-butoxycarbonyl-D-valyl-D-leucyl}-(2'S)-pyrrolidyl-(2)]propionyl-D-asparaginyl-D-phenylalanine benzyl ester

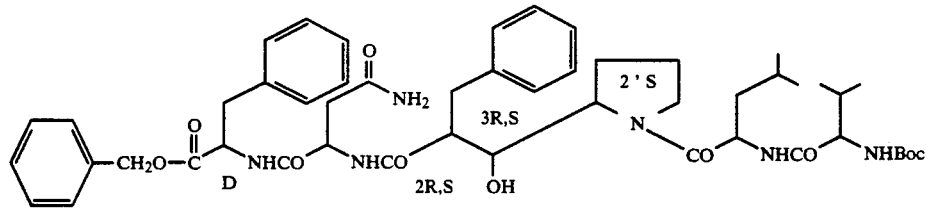

The title compound is obtained analogously to Example 168 from the compound of Example 187 and Boc-D-Val.

TLC system IV: Rf=0.59.
(+)FAB-MS: m/e 913 (M+H).
HPLC system II: Rf=16.50 min.

It will be understood that the specification and examples are illustrative but not limitative of the present invention and that other embodiments within the spirit and scope of the invention will suggest themselves to those skilled in the art.

We claim:

1. A compound of the formula

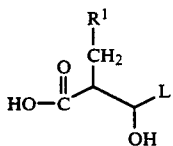

(11a)

in which

R¹ represents straight-chain or branched alkyl having up to 4 carbon atoms, cyclohexyl or phenyl, L represents a group of the formula —CH₂—NR²R³ in which

R² and R³ are identical or different and in each case represent hydrogen, phenyl or represent straight-chain or branched alkyl having up to 4 carbon atoms, which is optionally substituted by phenyl pr pyridyl, or represent a group of the formula —COR⁹ in which R⁹ denotes straight-chain or branched alkyl having up to 4 carbon atoms, which may be substituted by phenyl or pyridyl, or denotes phenyl which, in turn, may be substituted by carboxyl, alkoxycarbonyl having up to 4 carbon atoms or by a group of the formula —CONR¹⁰R¹¹ in which R¹⁰ and R¹¹ are identical or different and in each case denote cyclopentyl, hydrogen or straight-chain or branched alkyl having up to 4 carbon atoms, which, in turn, may be substituted by phenyl or pyridyl, or one of the substituents R² and R³ represents an amino protecting group or R² and R³ together represent phthalimido or morpholino or represents a group pf the formula

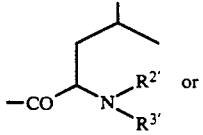

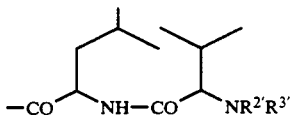

in which

R²' represents hydrogen and

R³' represents hydrogen Boc, ethoxycarbonyl or pyridylacetyl, or

R²' and R³' together represent a morpholino group, or

L represents a group of the formula

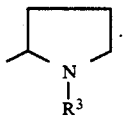

* * * * *

UNITED STATES PATENT AND TRADEMARK OFFICE
CERTIFICATE OF CORRECTION

PATENT NO. : 5,242,903

DATED : September 7, 1993

INVENTOR(S) : Bender, et al.

It is certified that error appears in the above-identified patent and that said Letters Patent is hereby corrected as shown below:

Col. 101, line 46    After " phenyl " delete " pr " and substitute -- or --

Col. 102, line 22    After " group " delete " pf " and substitute -- of --

Signed and Sealed this

Third Day of January, 1995

Attest:

BRUCE LEHMAN

*Attesting Officer*    *Commissioner of Patents and Trademarks*